US007462447B2

(12) United States Patent
Tiziani et al.

(10) Patent No.: US 7,462,447 B2
(45) Date of Patent: Dec. 9, 2008

(54) METHODS FOR EVALUATING SUSCEPTIBILITY TO A BONE HOMEOSTASIS DISORDER

(75) Inventors: Valdenize Tiziani, Fortaleza CE (BR); Ernst Reichenberger, West Hartford, CT (US); Yasuyoshi Ueki, Needham, MA (US); Bjorn R. Olsen, Milton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 36 days.

(21) Appl. No.: 10/467,033

(22) PCT Filed: Feb. 1, 2002

(86) PCT No.: PCT/US02/19164

§ 371 (c)(1),
(2), (4) Date: Jun. 24, 2005

(87) PCT Pub. No.: WO03/025197

PCT Pub. Date: Mar. 27, 2003

(65) Prior Publication Data

US 2006/0019248 A1  Jan. 26, 2006

(51) Int. Cl.
*C12P 1/68* (2006.01)
*C12P 19/34* (2006.01)
*C12N 9/00* (2006.01)
*C07H 21/04* (2006.01)
*C07K 1/00* (2006.01)

(52) U.S. Cl. .............................. 435/6; 435/6; 435/91.2; 435/183; 536/23.1; 536/24.31; 536/24.33; 530/350

(58) Field of Classification Search .................... 435/6, 435/91.2, 183; 536/23.1, 24.31, 24.33; 530/350
See application file for complete search history.

(56) References Cited

FOREIGN PATENT DOCUMENTS

WO    WO 03025197 A2    3/2003

OTHER PUBLICATIONS

New England BioLabs, Inc., Jan. 2001 Catalog and Technical Reference, 2000, p. 125.*
Baxendale, S. et al., A cosmid contig and high resolution restriction map of the 2 megabase region containing the Huntington's disease gene. Nature Genetics 4: 181-186, 1993.
Bell, S.M. et al., Identification and characterization of the human homologue of SH3BP2, an SH3 binding domain protein within a common region of deletion at 4p16.3 involved in bladder cancer. Genomics 44: 163-170, 1997.
Bianco, P. et al., Mutations of the GNAS1 gene, stromal cell dysfunction, and osteomalacic changes in non-McCune-Albright fibrous dysplasia of bone. Bone Miner Res. 15: 120-128, 2000.
Deckert, M. et al., Adaptor function for the Syk kinases-interacting protein 3BP2 in IL-2 gene activation. Immunity 9: 595-605, 1998.
Gibco BRL Products and References Guide, Radon Primers, 1997, 17-19.
Hadano, S. et al., The primary structure and genomic organization of five novel transcripts located close to the Huntington's disease gene on human chromosome 4p16.3. DNA Research 5: 177-186, 1998.
Hirschhorn, K. et al., Deletion of short arms of chromosome 4-5 in a child with defects of midline fusion. Humangenetik 1: 479-482, 1965.
Jones, W.A., Familial multilocular cystic disease of the jaws. Amer. J. of Cancer 17: 946-950, 1933.
Lewis, J.M. et al., Integrin regulation of c-Abl tyrosine kinase activity and cytoplasmic-nuclear transport. Proc. Natl. Acad. Sci. USA 93: 15174-15179, 1996.
Li, B. et al., Mice deficient in Abl are osteoporotic and have defects in osteoblast maturation. Nat. Genet. 24: 304-308, 2000.
Mangion, J. et al., The gene for cherubism maps to chromosome 4p16.3. Amer. J. of Human Genetics 65: 151-157, 1999.
Pawson, T. et al., SH2 and SH3 domains: from structure to function. Cell 71: 359-362, 1992.
Pribill, I. et al., Exon trapping and sequence-based methods of gene finding in transcript mapping of human 4p16.3. Somatic Cell & Molecular Genetics 23: 413-427, 1997.
Ren, R. et al., Identification of a ten-amino acid proline-rich SH3 binding site. Science 259: 1157-1161, 1993.
Songyang, Z. et al., Specific motifs recognized by the SH2 domains of Csk, 3BP2, fps/fes, GRB-2, HCP, SHC, Syk, and Vav. Mol. Cell. Biol. 14: 2777-2785, 1994.
Sparks, A.B. et al., Distinct ligand preferences of Src homology 3 domains from Src, Yes, Abl, Cortactin, p53bp2, PLCgamma, Crk, and Grb2. Proc. Natl. Acad. Sci USA 93: 1540-1544, 1996.
Tiziani, V. et al., The gene for cherubism maps to chromosome 4p16. Amer. J. of Human Genetics 65: 158-166, 1999.
Ueki, Y. et al., Mutations in the gene encoding c-Abl-binding protein SH3BP2 cause cherubism. Nat Genet. Jun. 2001;28(2):125-6.
Weinstein, L.S. et al., Activating mutations of the stimulatory G protein in the McCune-Albright syndrome. N. Engl. J. Med. 325: 1688-1695, 1991.
Welch, P.J. et al., A C-terminal protein-binding domain in the retinoblastoma protein regulates nuclear c-Abl tyrosine kinase in the cell cycle. Cell 75: 779-790, 1993.
Zohar, Y. Fibrous dysplasia and cherubism as an hereditary familial disease. Follow-up of four generations. J Craniomaxillofac Surg. Nov. 1989;17(8):340-4.
Zollino, M. et al., Genotype-phenotype correlations and clinical diagnostic criteria in Wolf-Hirschhorn syndrome. Am. J. Med. Genet. 18: 254-261, 2000.

* cited by examiner

*Primary Examiner*—Bradley L Sisson
(74) *Attorney, Agent, or Firm*—Wolf, Greenfield & Sacks, P.C.

(57) ABSTRACT

The invention provides mutant SH3-binding protein (SH3BP2) nucleic acids, polypeptides, and agents which selectively bind to the mutant SH3BP2 molecules and which do not bind to the wild type SH3BP2 molecules. Methods for selecting agents which inhibit mutant SH3BP2 expression, as well as diagnostic and therapeutic methods which utilize the mutant SH3BP2 molecules for diagnosing and treating disorders of bone homeostasis, also are provided.

3 Claims, 3 Drawing Sheets

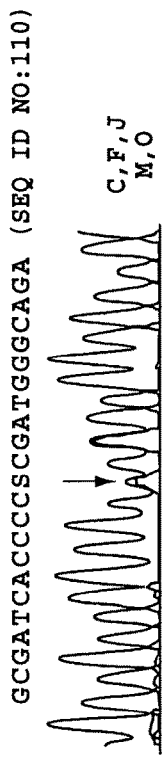
GCGATCACCCCCGATGGGCAGA (SEQ ID NO:106)
WT
Fig. 3A
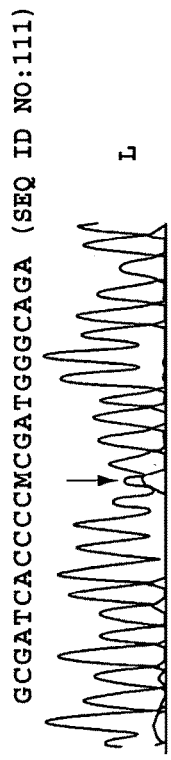
GCSATCACCCCCGATGGGCAGA (SEQ ID NO:107)
H
Fig. 3B
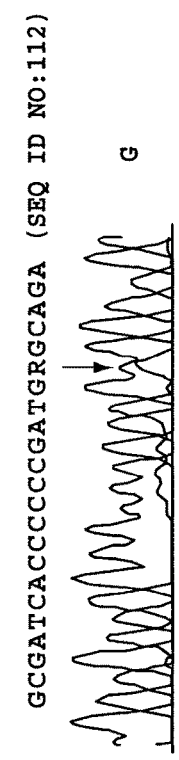
GCRATCACCCCCGATGGGCAGA (SEQ ID NO:108)
K
Fig. 3C
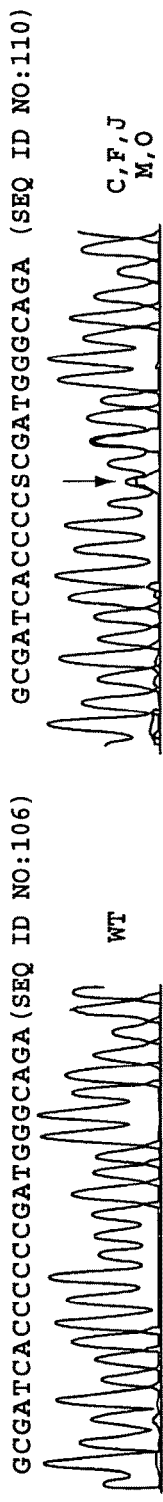
GCGATCACCCCYCGATGGGCAGA (SEQ ID NO:109)
A,B
Fig. 3D
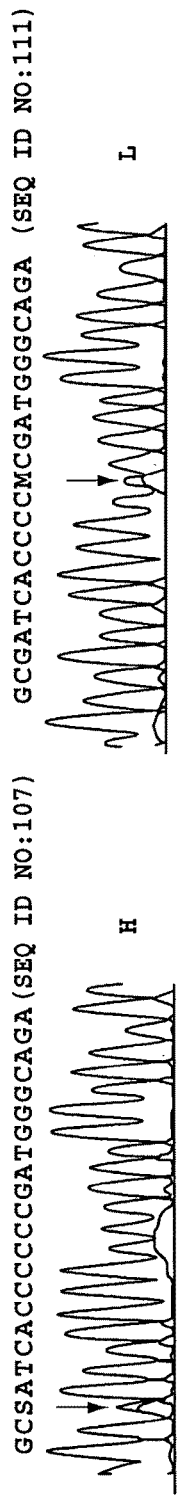
GCGATCACCCCCSGATGGGCAGA (SEQ ID NO:110)
C,F,J
M,O
Fig. 3E
GCGATCACCCCMCGATGGGCAGA (SEQ ID NO:111)
L
Fig. 3F
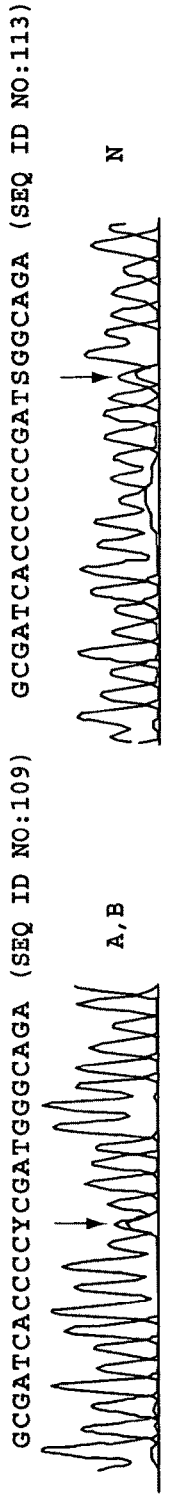
GCGATCACCCCCGATGRGCAGA (SEQ ID NO:112)
G
Fig. 3G
GCGATCACCCCCGATSGGCAGA (SEQ ID NO:113)
N
Fig. 3H

SEQUENCE LISTING

```
<160> NUMBER OF SEQ ID NOS: 113

<210> SEQ ID NO 1
<211> LENGTH: 2347
<212> TYPE: DNA
<213> ORGANISM: homo sapiens

<400> SEQUENCE: 1
ggggaggagc cggcggctgc caggccaggg ccggcgggca tggcgggctc cgggccggcc      60
gcggagctgg ggccggcggg aggcgggcgc ccgggacgag gcggcggcgg ccggggacg      120 cggcccgggg ccgtgccggt gctcgcaggg gaggcgggcg tggatcgccc cggggaagcc     180
ggccatgccc gccgcgtgga cgcccttcat ggcggctgaa gagatgcatt ggcctgtccc     240
tatgaaggcc attggtgccc agaacctgct aaccatgcct gggggcgtgg ccaaggctgg     300
ctacctgcac aagaagggcg gtaccagct gcagctgctg aaatggcccc tgcgctttgt      360
catcatccac aaacgctgcg tctactactt caagagtagc acctctgcct ccccgcaggg      420
cgccttctcc ctgagtggct ataacgggt gatgcgggcg gctgaggaga ccacgtccaa      480
caacgttttc cccttcaaga tcatccacat cagcaagaag caccgcacgt ggttcttctc      540
ggcctcctct gaggaggagc gcaagagctg gatggccttg ctgcgcaggg agattggcca      600
cttccacgaa aagaaagacc tgcccttgga caccagcgac tccagctcgg acacagacag      660
cttctacggc gcagttgagc ggcctgtgga tatcagcctt tccccgtacc ccacgacaa      720
```

```
tgaagactat gagcacgacg atgaggatga ctcctacctg gagcctgact ccccggagcc      780
cggaaggctt gaggatgccc tgatgcaccc accggcttac ccaccacccc cagtgcccac      840
gcccaggaag ccagccttct ctgacatgcc cgggcccac tcctttacct caagggccc        900 cggtcccta ctgccacccc cgcccccta agcacggcctc ccagatgttg gcctggcggc      960
tgaggactcc aagagggacc cactgtgccc gaggcgggct gagccttgcc ccagggtacc    1020 tgctacccccc gaaggatga gcgatccccc tctgagcacc atgcccaccg cacccggcct     1080
ccggaaaccc ccttgcttcc gggagagtgc cagccccagc ccggagccct ggaccctgg      1140 ccacggggcc tgctccactt ccagtgctgc catcatggcc actgccacct ccagaaactg    1200
tgacaaactc aagtccttcc acctgtcccc ccgaggacca cccacatctg agccccccacc  1260 tgtgccagcc aacaagccca agttcctgaa gatagctgaa gaggaccccc caagggaggc     1320
agccatgccc ggactctttg tgcccccccgt ggctccccgg cctcctgcgc tgaagctgcc   1380
agtgcctgag gccatggcgc ggcccgcagt cctgcccagg ccagagaagc gcagctccc    1440 gcacctccag cgatcacccc ccgatgggca gagtttcagg agcttctcct ttgaaaagcc   1500
ccggcaaccc tcacaggctg acactggcgg ggacgactcg gacgaggact atgagaaggt   1560
gccactgccc aactcggtct tcgtcaacac cacggagtcc tgcgaagtgg aaaggttgtt    1620
caaggctaca agccccgggg agagccccca ggatggactc tactgcatcc ggaactcctc    1680
taccaagtcg gggaaggtcc tggttgtgtg ggacgaaacc tctaacaaag tgaggaacta   1740
tcgcattttt gagaaggact ctaagttcta cctggagggc gaggtcctgt ttgtgagtgt    1800
gggcagcatg gtggagcact accacaccca cgtgctgccc agccaccaga gcctgctgct   1860
gcggcacccc tacggctaca ctgggcctag gtgatggcag tccatgtggc tgccaggcca    1920
aggcagtcac aggggccctg accccaggcc acacagacgg acatgggccc acatggagg     1980 gtgagcagga gcaaggcggt gcttgcctag ggcctgtgat ggacatctcg taggacccag    2040
ccagtctcat ccagcaggtt gggttctagg gctgaaccag gcgccaggct ccagaggacg    2100
aagggactct gttgccccac actaacttgc cctgtcccaa tccagaaaac ccaggaccaa    2160
gctgtgcctg gctccaagg acaggaacac tggtcccccc atcacactca ccctaagtg      2220 ggctgggagc caggcaggc cagggcagct gggtgggggc cggggctggc cctgggaccc     2280
ccaggaacgc taagacacag gctccagtag gggctgttgc ctccaataaa gcagcagtga    2340
gctttgc                                                               2347
```

<210> SEQ ID NO 2
<211> LENGTH: 561
<212> TYPE: PRT
<213> ORGANISM: homo sapiens

<400> SEQUENCE: 2

```
Met Ala Ala Glu Glu Met His Trp Pro Val Pro Met Lys Ala Ile Gly
 1               5                  10                  15

Ala Gln Asn Leu Leu Thr Met Pro Gly Gly Val Ala Lys Ala Gly Tyr
            20                  25                  30

Leu His Lys Lys Gly Gly Thr Gln Leu Gln Leu Leu Lys Trp Pro Leu
        35                  40                  45

Arg Phe Val Ile Ile His Lys Arg Cys Val Tyr Phe Lys Ser Ser
    50                  55                  60

Thr Ser Ala Ser Pro Gln Gly Ala Phe Ser Leu Ser Gly Tyr Asn Arg
65                  70                  75                  80
```

-continued

```
Val Met Arg Ala Ala Glu Glu Thr Thr Ser Asn Asn Val Phe Pro Phe
                85                  90                  95

Lys Ile Ile His Ile Ser Lys Lys His Arg Thr Trp Phe Phe Ser Ala
            100                 105                 110

Ser Ser Glu Glu Glu Arg Lys Ser Trp Met Ala Leu Leu Arg Arg Glu
        115                 120                 125

Ile Gly His Phe His Glu Lys Lys Asp Leu Pro Leu Asp Thr Ser Asp
    130                 135                 140

Ser Ser Ser Asp Thr Asp Ser Phe Tyr Gly Ala Val Glu Arg Pro Val
145                 150                 155                 160

Asp Ile Ser Leu Ser Pro Tyr Pro Thr Asp Asn Glu Asp Tyr Glu His
                165                 170                 175

Asp Asp Glu Asp Asp Ser Tyr Leu Glu Pro Asp Ser Pro Glu Pro Gly
            180                 185                 190

Arg Leu Glu Asp Ala Leu Met His Pro Pro Ala Tyr Pro Pro Pro Pro
        195                 200                 205

Val Pro Thr Pro Arg Lys Pro Ala Phe Ser Asp Met Pro Arg Ala His
    210                 215                 220

Ser Phe Thr Ser Lys Gly Pro Gly Pro Leu Leu Pro Pro Pro Pro Pro
225                 230                 235                 240

Lys His Gly Leu Pro Asp Val Gly Leu Ala Ala Glu Asp Ser Lys Arg
                245                 250                 255

Asp Pro Leu Cys Pro Arg Arg Ala Glu Pro Cys Pro Arg Val Pro Ala
            260                 265                 270

Thr Pro Arg Arg Met Ser Asp Pro Pro Leu Ser Thr Met Pro Thr Ala
        275                 280                 285

Pro Gly Leu Arg Lys Pro Pro Cys Phe Arg Glu Ser Ala Ser Pro Ser
    290                 295                 300

Pro Glu Pro Trp Thr Pro Gly His Gly Ala Cys Ser Thr Ser Ser Ala
305                 310                 315                 320

Ala Ile Met Ala Thr Ala Thr Ser Arg Asn Cys Asp Lys Leu Lys Ser
                325                 330                 335

Phe His Leu Ser Pro Arg Gly Pro Pro Thr Ser Glu Pro Pro Pro Val
            340                 345                 350

Pro Ala Asn Lys Pro Lys Phe Leu Lys Ile Ala Glu Glu Asp Pro Pro
        355                 360                 365

Arg Glu Ala Ala Met Pro Gly Leu Phe Val Pro Val Ala Pro Arg
    370                 375                 380

Pro Pro Ala Leu Lys Leu Pro Val Pro Glu Ala Met Ala Arg Pro Ala
385                 390                 395                 400

Val Leu Pro Arg Pro Glu Lys Pro Gln Leu Pro His Leu Gln Arg Ser
                405                 410                 415

Pro Pro Asp Gly Gln Ser Phe Arg Ser Phe Ser Phe Glu Lys Pro Arg
            420                 425                 430

Gln Pro Ser Gln Ala Asp Thr Gly Gly Asp Asp Ser Asp Glu Asp Tyr
        435                 440                 445

Glu Lys Val Pro Leu Pro Asn Ser Val Phe Val Asn Thr Thr Glu Ser
    450                 455                 460

Cys Glu Val Glu Arg Leu Phe Lys Ala Thr Ser Pro Arg Gly Glu Pro
465                 470                 475                 480

Gln Asp Gly Leu Tyr Cys Ile Arg Asn Ser Ser Thr Lys Ser Gly Lys
                485                 490                 495
```

```
Val Leu Val Val Trp Asp Glu Thr Ser Asn Lys Val Arg Asn Tyr Arg
            500                 505                 510

Ile Phe Glu Lys Asp Ser Lys Phe Tyr Leu Glu Gly Glu Val Leu Phe
            515                 520                 525

Val Ser Val Gly Ser Met Val Glu His Tyr His Thr His Val Leu Pro
            530                 535                 540

Ser His Gln Ser Leu Leu Leu Arg His Pro Tyr Gly Tyr Thr Gly Pro
545                 550                 555                 560

Arg

<210> SEQ ID NO 3
<211> LENGTH: 21
<212> TYPE: DNA
<213> ORGANISM: homo sapiens

<400> SEQUENCE: 3
cgatcacccc ccgatgggca g                                              21

<210> SEQ ID NO 4
<211> LENGTH: 7
<212> TYPE: PRT
<213> ORGANISM: homo sapiens

<400> SEQUENCE: 4

Arg Ser Pro Pro Asp Gly Gln
1               5

<210> SEQ ID NO 5
<211> LENGTH: 2347
<212> TYPE: DNA
<213> ORGANISM: homo sapiens
<220> FEATURE:
<221> NAME/KEY: misc_feature
<222> LOCATION: (1452)..(1452)
<223> OTHER INFORMATION: n = C, T, G or A
      provided that the mutant domain is not wild type
<220> FEATURE:
<221> NAME/KEY: misc_feature
<222> LOCATION: (1461)..(1461)
<223> OTHER INFORMATION: n = C, T, G or A
      provided that the mutant domain is not wild type
<220> FEATURE:
<221> NAME/KEY: misc_feature
<222> LOCATION: (1466)..(1467)
<223> OTHER INFORMATION: n = C, T, G or A
      provided that the mutant domain is not wild type

<400> SEQUENCE: 5
ggggaggagc cggcggctgc caggccaggg ccggcgggca tggcgggctc cgggccggcc        60
gcggagctgg ggccggcggg aggcgggcgc ccggacgag gcggcggcgg ccggggacg         120 cggcccgggg ccgtgccggt gctcgcaggg gaggcgggcg tggatcgccc cggggaagcc       180
ggccatgccc gccgcgtgga cgcccttcat ggcggctgaa gagatgcatt ggcctgtccc       240
tatgaaggcc attggtgccc agaacctgct aaccatgcct gggggcgtgg ccaaggctgg       300
ctacctgcac aagaagggcg gtacccagct gcagctgctg aaatggcccc tgcgctttgt       360
catcatccac aaacgctgcg tctactactt caagagtagc acctctgcct ccccgcaggg       420
cgccttctcc ctgagtggct ataaccgggt gatgcgggcg gctgaggaga ccacgtccaa       480
caacgttttc cccttcaaga tcatccacat cagcaagaag caccgcacgt ggttcttctc       540
ggcctcctct gaggaggagc gcaagagctg gatggcttg ctgcgcaggg agattggcca        600
cttccacgaa aagaaagacc tgcccttgga caccagcgac tccagctcgg acacagacag       660
```

```
cttctacggc gcagttgagc ggcctgtgga tatcagcctt tccccgtacc ccacggacaa    720
tgaagactat gagcacgacg atgaggatga ctcctacctg gagcctgact ccccggagcc    780
cggaaggctt gaggatgccc tgatgcaccc accggcttac ccaccacccc cagtgcccac    840
gcccaggaag ccagccttct ctgacatgcc ccgggcccac tcctttacct ccaagggccc    900
cggtccccta ctgccacccc cgcccccctaa gcacggcctc ccagatgttg gcctggcggc    960
tgaggactcc aagagggacc cactgtgccc gaggcgggct gagccttgcc ccagggtacc   1020
tgctaccccc cgaaggatga gcgatccccc tctgagcacc atgccaccg cacccggcct   1080 ccggaaaccc ccttgcttcc gggagagtgc cagccccagc ccggagccct ggacccctgg   1140
ccacggggcc tgctccactt ccagtgctgc catcatggcc actgccacct ccagaaactg   1200
tgacaaactc aagtccttcc acctgtcccc ccgaggacca cccacatctg agcccccacc   1260
tgtgccagcc aacaagccca agttcctgaa gatagctgaa gaggaccccc caagggaggc   1320
agccatgccc ggactctttg tgccccccgt ggctccccgg cctcctgcgc tgaagctgcc   1380
agtgcctgag gccatggcgc ggcccgcagt cctgcccagg ccagagaagc cgcagctccc   1440
gcacctccag cnatcacccc ncgatnngca gagtttcagg agcttctcct ttgaaaagcc   1500
ccggcaaccc tcacaggctg acactggcgg ggacgactcg gacgaggact atgaaaggt   1560 gccactgccc aactcggtct tcgtcaacac cacggagtcc tgcgaagtgg aaaggttgtt   1620
caaggctaca agcccccggg gagagcccca ggatggactc tactgcatcc ggaactcctc   1680
taccaagtcg gggaaggtcc tggttgtgtg ggacgaaacc tctaacaaag tgaggaacta   1740
tcgcattttt gagaaggact ctaagttcta cctggagggc gaggtcctgt ttgtgagtgt   1800
gggcagcatg gtggagcact accacaccca cgtgctgccc agccaccaga gcctgctgct   1860
gcggcacccc tacggctaca ctgggcctag gtgatggcag tccatgtggc tgccaggcca   1920
aggcagtcac aggggccctg accccaggcc acacagacgg acatgggccc acatgggagg   1980
gtgagcagga gcaaggcggt gcttgcctag ggcctgtgat ggacatctcg taggacccag   2040
ccagtctcat ccagcaggtt gggttctagg gctgaaccag gcgccaggct ccagaggacg   2100
aagggactct gttgccccac actaacttgc cctgtcccaa tcccagaaac ccaggaccaa   2160
gctgtgcctg ggctccaagg acaggaacac tggtccccc atcacactca ccctaagtg   2220 ggctgggagc caggcagggc cagggcagct gggtgggggc cggggctggc cctgggaccc   2280
ccaggaacgc taagacacag gctccagtag gggctgttgc ctccaataaa gcagcagtga   2340
gctttgc                                                             2347
```

<210> SEQ ID NO 6
<211> LENGTH: 561
<212> TYPE: PRT
<213> ORGANISM: homo sapiens
<220> FEATURE:
<221> NAME/KEY: MISC_FEATURE
<222> LOCATION: (415)..(415)
<223> OTHER INFORMATION: Xaa = any amino acid
      provided that the mutant domain is not wild type
<220> FEATURE:
<221> NAME/KEY: MISC_FEATURE
<222> LOCATION: (418)..(418)
<223> OTHER INFORMATION: Xaa = any amino acid
      provided that the mutant domain is not wild type
<220> FEATURE:
<221> NAME/KEY: MISC_FEATURE
<222> LOCATION: (420)..(420)
<223> OTHER INFORMATION: Xaa = any amino acid
      provided that the mutant domain is not wild type

<400> SEQUENCE: 6

```
Met Ala Ala Glu Glu Met His Trp Pro Val Pro Met Lys Ala Ile Gly
1               5                   10                  15

Ala Gln Asn Leu Leu Thr Met Pro Gly Gly Val Ala Lys Ala Gly Tyr
            20                  25                  30

Leu His Lys Lys Gly Gly Thr Gln Leu Gln Leu Leu Lys Trp Pro Leu
        35                  40                  45

Arg Phe Val Ile Ile His Lys Arg Cys Val Tyr Tyr Phe Lys Ser Ser
    50                  55                  60

Thr Ser Ala Ser Pro Gln Gly Ala Phe Ser Leu Ser Gly Tyr Asn Arg
65                  70                  75                  80

Val Met Arg Ala Ala Glu Glu Thr Thr Ser Asn Asn Val Phe Pro Phe
                85                  90                  95

Lys Ile Ile His Ile Ser Lys Lys His Arg Thr Trp Phe Phe Ser Ala
            100                 105                 110

Ser Ser Glu Glu Glu Arg Lys Ser Trp Met Ala Leu Leu Arg Arg Glu
        115                 120                 125

Ile Gly His Phe His Glu Lys Lys Asp Leu Pro Leu Asp Thr Ser Asp
    130                 135                 140

Ser Ser Ser Asp Thr Asp Ser Phe Tyr Gly Ala Val Glu Arg Pro Val
145                 150                 155                 160

Asp Ile Ser Leu Ser Pro Tyr Pro Thr Asp Asn Glu Asp Tyr Glu His
            165                 170                 175

Asp Asp Glu Asp Asp Ser Tyr Leu Glu Pro Asp Ser Pro Glu Pro Gly
        180                 185                 190

Arg Leu Glu Asp Ala Leu Met His Pro Pro Ala Tyr Pro Pro Pro Pro
    195                 200                 205

Val Pro Thr Pro Arg Lys Pro Ala Phe Ser Asp Met Pro Arg Ala His
210                 215                 220

Ser Phe Thr Ser Lys Gly Pro Gly Pro Leu Leu Pro Pro Pro Pro Pro
225                 230                 235                 240

Lys His Gly Leu Pro Asp Val Gly Leu Ala Ala Glu Asp Ser Lys Arg
            245                 250                 255

Asp Pro Leu Cys Pro Arg Arg Ala Glu Pro Cys Pro Arg Val Pro Ala
        260                 265                 270

Thr Pro Arg Arg Met Ser Asp Pro Pro Leu Ser Thr Met Pro Thr Ala
    275                 280                 285

Pro Gly Leu Arg Lys Pro Pro Cys Phe Arg Glu Ser Ala Ser Pro Ser
290                 295                 300

Pro Glu Pro Trp Thr Pro Gly His Gly Ala Cys Ser Thr Ser Ser Ala
305                 310                 315                 320

Ala Ile Met Ala Thr Ala Thr Ser Arg Asn Cys Asp Lys Leu Lys Ser
            325                 330                 335

Phe His Leu Ser Pro Arg Gly Pro Pro Thr Ser Glu Pro Pro Pro Val
        340                 345                 350

Pro Ala Asn Lys Pro Lys Phe Leu Lys Ile Ala Glu Glu Asp Pro Pro
    355                 360                 365

Arg Glu Ala Ala Met Pro Gly Leu Phe Val Pro Val Ala Pro Arg Pro
370                 375                 380

Pro Pro Ala Leu Lys Leu Pro Val Pro Glu Ala Met Ala Arg Pro Ala
385                 390                 395                 400

Val Leu Pro Arg Pro Glu Lys Pro Gln Leu Pro His Leu Gln Xaa Ser
```

-continued

```
                        405                 410                 415

Pro Xaa Asp Xaa Gln Ser Phe Arg Ser Phe Ser Phe Glu Lys Pro Arg
            420                 425                 430

Gln Pro Ser Gln Ala Asp Thr Gly Gly Asp Asp Ser Asp Glu Asp Tyr
        435                 440                 445

Glu Lys Val Pro Leu Pro Asn Ser Val Phe Val Asn Thr Thr Glu Ser
    450                 455                 460

Cys Glu Val Glu Arg Leu Phe Lys Ala Thr Ser Pro Arg Gly Glu Pro
465                 470                 475                 480

Gln Asp Gly Leu Tyr Cys Ile Arg Asn Ser Ser Thr Lys Ser Gly Lys
                485                 490                 495

Val Leu Val Val Trp Asp Glu Thr Ser Asn Lys Val Arg Asn Tyr Arg
            500                 505                 510

Ile Phe Glu Lys Asp Ser Lys Phe Tyr Leu Glu Gly Glu Val Leu Phe
        515                 520                 525

Val Ser Val Gly Ser Met Val Glu His Tyr His Thr His Val Leu Pro
    530                 535                 540

Ser His Gln Ser Leu Leu Leu Arg His Pro Tyr Gly Tyr Thr Gly Pro
545                 550                 555                 560

Arg

<210> SEQ ID NO 7
<211> LENGTH: 21
<212> TYPE: DNA
<213> ORGANISM: homo sapiens
<220> FEATURE:
<221> NAME/KEY: misc_feature
<222> LOCATION: (2)..(2)
<223> OTHER INFORMATION: n = independently selected from S, R, Y or M
      i.e. n is C, T, G or A provided that the mutant domain is not wil
      d type
<220> FEATURE:
<221> NAME/KEY: misc_feature
<222> LOCATION: (11)..(11)
<223> OTHER INFORMATION: n = independently selected from S, R, Y or M
      i.e. n is C, T, G or A provided that the mutant domain is not wil
      d type
<220> FEATURE:
<221> NAME/KEY: misc_feature
<222> LOCATION: (16)..(17)
<223> OTHER INFORMATION: n = independently selected from S, R, Y or M
      i.e. n is C, T, G or A provided that the mutant domain is not wil
      d type

<400> SEQUENCE: 7
cnatcacccc ncgatnngca g                                             21

<210> SEQ ID NO 8
<211> LENGTH: 7
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: Xaa = any amino acid
      provided that the mutant domain is not wild type
<220> FEATURE:
<221> NAME/KEY: MISC_FEATURE
<222> LOCATION: (4)..(4)
<223> OTHER INFORMATION: Xaa = any amino acid
      provided that the mutant domain is not wild type
<220> FEATURE:
<221> NAME/KEY: MISC_FEATURE
<222> LOCATION: (6)..(6)
<223> OTHER INFORMATION: Xaa = any amino acid
      provided that the mutant domain is not wild type
```

-continued

```
<400> SEQUENCE: 8

Xaa Ser Pro Xaa Asp Xaa Gln
1               5

<210> SEQ ID NO 9
<211> LENGTH: 21
<212> TYPE: DNA
<213> ORGANISM: homo sapiens

<400> SEQUENCE: 9
csatcacccc ccgatgggca g                                              21

<210> SEQ ID NO 10
<211> LENGTH: 7
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: Xaa = Pro

<400> SEQUENCE: 10

Xaa Ser Pro Pro Asp Gly Gln
1               5

<210> SEQ ID NO 11
<211> LENGTH: 21
<212> TYPE: DNA
<213> ORGANISM: homo sapiens

<400> SEQUENCE: 11
cratcacccc ccgatgggca g                                              21

<210> SEQ ID NO 12
<211> LENGTH: 7
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: Xaa = Gln

<400> SEQUENCE: 12

Xaa Ser Pro Pro Asp Gly Gln
1               5

<210> SEQ ID NO 13
<211> LENGTH: 21
<212> TYPE: DNA
<213> ORGANISM: homo sapiens

<400> SEQUENCE: 13
cgatcacccc ycgatgggca g                                              21

<210> SEQ ID NO 14
<211> LENGTH: 7
<212> TYPE: PRT
<213> ORGANISM: homo sapiens
<220> FEATURE:
<221> NAME/KEY: MISC_FEATURE
<222> LOCATION: (4)..(4)
<223> OTHER INFORMATION: Xaa = Leu

<400> SEQUENCE: 14

Arg Ser Pro Xaa Asp Gly Gln
```

```
<210> SEQ ID NO 15
<211> LENGTH: 21
<212> TYPE: DNA
<213> ORGANISM: homo sapiens

<400> SEQUENCE: 15
cgatcacccc scgatgggca g                                              21

<210> SEQ ID NO 16
<211> LENGTH: 7
<212> TYPE: PRT
<213> ORGANISM: homo sapiens
<220> FEATURE:
<221> NAME/KEY: MISC_FEATURE
<222> LOCATION: (4)..(4)
<223> OTHER INFORMATION: Xaa = Arg

<400> SEQUENCE: 16

Arg Ser Pro Xaa Asp Gly Gln
1               5

<210> SEQ ID NO 17
<211> LENGTH: 21
<212> TYPE: DNA
<213> ORGANISM: homo sapiens

<400> SEQUENCE: 17
cgatcacccc mcgatgggca g                                              21

<210> SEQ ID NO 18
<211> LENGTH: 7
<212> TYPE: PRT
<213> ORGANISM: homo sapiens
<220> FEATURE:
<221> NAME/KEY: MISC_FEATURE
<222> LOCATION: (4)..(4)
<223> OTHER INFORMATION: Xaa = His

<400> SEQUENCE: 18

Arg Ser Pro Xaa Asp Gly Gln
1               5

<210> SEQ ID NO 19
<211> LENGTH: 21
<212> TYPE: DNA
<213> ORGANISM: homo sapiens

<400> SEQUENCE: 19
cgatcacccc ccgatgrgca g                                              21

<210> SEQ ID NO 20
<211> LENGTH: 7
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: Xaa = Glu

<400> SEQUENCE: 20

Arg Ser Pro Pro Asp Xaa Gln
1               5

<210> SEQ ID NO 21
```

```
<211> LENGTH: 21
<212> TYPE: DNA
<213> ORGANISM: homo sapiens

<400> SEQUENCE: 21
cgatcacccc ccgatsggca g                                              21

<210> SEQ ID NO 22
<211> LENGTH: 7
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: Xaa = Arg

<400> SEQUENCE: 22

Arg Ser Pro Pro Asp Xaa Gln
1               5

<210> SEQ ID NO 23
<211> LENGTH: 20
<212> TYPE: DNA
<213> ORGANISM: artificial sequence
<220> FEATURE:
<223> OTHER INFORMATION: primer

<400> SEQUENCE: 23
cttgccgtcc tcacacagag                                                20

<210> SEQ ID NO 24
<211> LENGTH: 20
<212> TYPE: DNA
<213> ORGANISM: artificial sequence
<220> FEATURE:
<223> OTHER INFORMATION: primer

<400> SEQUENCE: 24
ttaggaactg tggagtcctg                                                20

<210> SEQ ID NO 25
<211> LENGTH: 22970
<212> TYPE: DNA
<213> ORGANISM: homo sapiens

<400> SEQUENCE: 25
gatcttcata ccctagaacc caggagtcag actcctgagt acaaaccctagaaaatttg      60 tgcaccattt gcaaaaaaca cacgtgcatc agagacatgg acaaaactgt tgctagcagc    120
attgtgtgta gttaccccaa actagaaaca aaccaactgt ccatctacag caggcatgtc    180
caatcttttg gcttccatgg accataccgg aagaactgtc tcgggtcacg cataaaatac    240
actaccacta actatagctg atgagctaaa aaaaaaaaat cgcaaacaaa aatctttata    300
atgttttaag aaagtttaca aatttgtgtt gggccacatt caaaggcatc ctgggctgca    360
tgcattggac aagcttgact gacagtgaaa tgaatctgtg aactacgata cagccaaaca    420
atggaagttt ttagcaatga acatgcacaa actatactac gcacagcaac atgaataaat    480
ctcacagaca taataacgag ccaaagaagc cagctgccag aatttgcatc tgtatgattc    540
aaggggataa agcacagaaa caggaaaata ctgcaatgcc tgcataattg ggtgctgaag    600 acttttttaga aaacaagaa cacaagactc acataagcca gggcagagag gccggaagtg    660
acactgtgag gggagggcac ttgggtgctg gcaaaactat ttcctgatgg tggttgcaga    720
```

-continued

```
tcgttcactt cctaacagtg tgttaggttg tgcatttatg ttttattcac ttttctgtat    780
gttgttttat tctgcaggaa atgaatgaaa aagggattct gcctcagctc tgagcccctc    840
agagtgggcc cagggaagaa gcagacggca acgccagggc agctgtctgg cagcctggaa    900
ggcctgcgaa gcttcctagg ggtccgaagg agggtagaca ggtaggggtc tgctctgtac    960
ccatcaaatc tccctccagt gagaatggtt ggaagatggc ttaaaagggt tcaccactca   1020
cacacacttc tgaggtggtg ggggttgtct gtcaagcatc ttcacaggggt cactgcccct   1080 cttccccaag gacaggcaac ctcctggcac tgcccctca gcaggcagtc taggtggagg    1140
gaacagggcg tgcaggcaga gataaggcag ggggtgtgtg cgaggtgccc agcgaggggc   1200
ttgatgctgc tgggtcacag aaacagaggt tgtggccctt cccccattcc cctcgtctag   1260
agacaagcac ggccctccca tgttcctggt gtgaccctgg tgtcctaggc catccctcca   1320
gcgcctggat caccctcaaa agcctcttcc ctgctgagct tcaatctgcc tttctatgaa   1380
atggccccaa taagccctgc ctgcctcagg gaactaagcc gcaggtccca ggtccccctc   1440
tcccccaatg cccaccctcg cccatcctga ggtgcaggaa gcacctccct ggggctgcgc   1500
tgagccccaa ccagcagggg agctccgcac aacgtggccc agaaggatca gtgggaaccg   1560
aggtttcttc tggttctaaa aacatctttt caaggctggg cgccgtggct cgcgcctgta   1620
atcccagcac ttgggaggcc aaggtggggcg gatcagttga ggtcaggagt tcaagaccag   1680
cctggccaac atggtgaaac cccggttcca ctaaaaatac aaaaatttgg caggcagctg   1740
taatcccagc tacatgggag ggtgaggcag gagaatcgat tgaaccctgg agatttgcat   1800
tgagccgaga tcacgccaat ccactctagc ctgggcgaca gagtgagact gtgtcccaaa   1860
aaaaaaagaa aaaatctttt cacaatacaa atctttatta actgaaggca cggggctcac   1920
cacaatcctt cggatggaac cacaggaaga gaagaagcat gtttcaccct gggctggggg   1980
tgcttcccaa agccactggg gcccttttcc caagccccag aactgagccc acctgaactc   2040
atcttgaagg taggtatgtc agtgagtcct cccaaagcct cagtttccct atctataaaa   2100
tgaggaagca ggactgcccc tagggcaagg cctaggcctc ctgccagccc accctcacag   2160
acccagaggg caacacaggg tgaggcgggg cagtttcact ccccagtgct gtggccccct   2220
tggttgagtg aaagcacctc cagagcccta accctagccc tgggagccag gcaagagacc   2280
cccacaacga ccatcagagg tcgtgagggg tggcagggag cctggcaggg agccaggcag   2340
gggccagggt ctaggctcag agcagtgaag gatagatagg gtcacatgcc agttagtggc   2400
agaggtggga cttgaaccca ggcctctgtg agacttggtt ctctcacctg taaaatgggt   2460
ctactagcag ctgcttctcc aagcaaatga tgtcaagcac ccagctcggc acctcacaga   2520
tgtggtcagt aaatggtaat cccaacccta cccttatatg tggactagaa cacttatggc   2580
aagtctcggg aggtcatggg aactcctcat ggctccttct tcatgctgga ggaccacggc   2640
ctgccccatc ccaccccaac acactcttga aactgaggcc ctcggcctag agcagctcac   2700
acagacgtgg acagctgtgc tagcaggtgc agagtctggg aggcgaggct ggaccagggc   2760
cccagctggg cttcgggtaa ccacaggcct caactgtcca gttggccaga gggacctatc   2820
acctggctct gggccccagg atgctttagc cacttgagcc ggctccaggt gaccgtgtaa   2880
gtgagataaa gcaaaggtgt cctggactgc accactcact agctcagcac cccaggcacc   2940
aggctggaaa ccacatctcg cacccaattc tccattttaaa aattttacag gaaggggcca   3000
ggcacagtgg ctcatgcctg taatcccagc actttgggag gccaaggtgg gcagatcacc   3060
tgaggtcagg agttcgagac cagcctggcc aacatgataa aatcccgtct ctactaaaaa   3120
```

```
tacaaaaaat tagccaggcg tggtggcggg cgcctggaat cccagctact cgggaggctg    3180
aggcaggaaa atcgcttgaa ctagagaggc ggaggtggca gtgagcggag atcacggcat    3240
tgcactccag cctgggcgac agggtgagac tacatctcaa aaacaaaaaa ctaaaataat    3300
aaaattttac aggaagagaa actatggcca cagtggggag tggcatgact ccctaagcaa    3360
gttcaggtca gacagggcaa agaattctga ctgcagggag gaggaatggc tggttttcca    3420
gagatagatc agaacaacag aagctccctg tgctccagcc tcggctgtgg tgcactgacc    3480
tctcacccca ggcaggctga agaggaaacc cctgcagagg tggccttgga cacctggttc    3540
ctggaagcag ctggctgccg tcatctgcag ggcctgcagt tccaccgcac cctatggccc    3600
ctggggtcac agcctcccac atccgctaac cagcctcatc acttgtttcc gccagcaaac    3660
cacaggtccc cagaacacac ccaggggaag ggggctgcag gaccttctcc cccagtcagt    3720
cactgtcagt gggcccaagt gctgacctca gtttaggttt ccctgacata aggtgctaag    3780
aaaaatcaca aggattctag ggtccctgcc agcccctacc tccctgagtc tgtttcatta    3840
aaaatccagc ctggaaggtg tgccaggagg agtgacctgc tggaactcca tggcagaaag    3900
taaggggatg gattggggct gggcctgagc caggtattgc ctggaagact tgggcatctg    3960
ggtaccaccg tccctacgca cccttggcct gcttagggtc cactgttccc atcccatcat    4020
agctgttact tcctccaaaa aatcttccgg gagccccag tccctgcaca cccagctgcc    4080
ctggacactg tgccgtaagc acctcatacc cagctgtccc cagactgggc tgtgaactca    4140
gccaggccag aggcccctgt ctggaatggg accaggcatg caggaggtac ccaataactg    4200
ctcgctaatg cagggaatga agcagctgta gctgcagggc cttctagctc tgtagcccgc    4260
tcagtgtatg caagttctgg aacggggaca gccactcagg aggtacccag taaccaggca    4320
ctaatgcagg gaatgaagca gctgtagctg cagggccttc tagctctgca gcagcactgc    4380
cctggcctga cctgaggcag cagaactggt gagtggggtg tgggctccca gcccagactg    4440
cccaagtttg ggtcctgatc tgttactcgc tgtgcaccct ggggaagtca ctcagtgacc    4500
tgcaccctgg aagacaagac aaccaactgt tggggttccc gggtactgct gcggtcacca    4560
cttagacatc agcatgggca cccagtaagc tggtaatccc ctccttccca atcaagcccc    4620
agccaccaag gcaaagctca ctgctgcttt attggaggca acagccccta ctggagcctg    4680
tgtcttagcg ttcctggggg tcccagggcc agccccggcc cccacccagc tgccctggcc    4740
ctgcctggct cccagcccac ttaggggtga gtgtgatggg gggaccagtg ttcctgtcct    4800
tggagcccag gcacagcttg gtcctgggtt tctgggattg gacagggca agttagtgtg    4860 gggcaacaga gtcccttcgt cctctggagc ctggcgcctg gttcagccct agaacccaac    4920
ctgctggatg agactggctg ggtcctacga gatgtccatc acagaggccc taggcaagca    4980
cagccttgct cctgctcacc ctcccatgtg ggcccatgtc cgtctgtgtg gcctggggtc    5040
agggcccctg tgactgcctt ggcctggcag ccacatggac tgccatcacc taggcccagt    5100
gtagccgtag gggtgccgca gcagcaggct ctggtggctg gcagcacgt gggtgtggta    5160 gtgctcccac catgctgccc acactcacaa acaggacctc gccctccagg tagaacttag    5220
agtcctgtgg gggaagagaa gggggagcgt cagcagggcc aggccactct gcggctctag    5280
gcctcagtct cccgtctgt aaaacaaggc agcagcatca acagcggcat caccaggctg    5340
gcccctggct gtcggtggtg cccccaaggt ggcctccgca tcaggcctgt gctctccatg    5400
ttcccacctc acttcccctc cgtcctccat gtccaggagc ctgcacccag agcacttcag    5460
```

```
acaaggtcag gaaatgaacc taggccaggc acggtggccc acgcctgtaa tcccagcact    5520
gtgggaggcc gaggtgggag gattgcttga gccccagaat ttgaaaccag cctgagaaag    5580
acagtgagac ccctgtcccc gcaaaaagaa aaagacaaga caagcaaccc agggtctatg    5640
gctgaccgcc catccccact agggtcagtg gaggacaaag gtaggccacg agaggaggga    5700
ggctgagcag gaggggtggg gggtgagcga tggtggaggg gaaggggagg gcggtatcct    5760
ggaggtgcca gtctcagtct acccgctgcc tatgcctcat cagggagatt ctgccctgcc    5820
ccttgccagg ccatgcggcc agggtccccg tcccactcag agccctctca ccttctcaaa    5880
aatgcgatag ttcctcactt tgttagaggt ttcgtcccac acaaccagga cctacaggac    5940
ggaagcggga ggctgacggc tccctgagaa acagcgggac cagcctcggg agaccatggg    6000
ctggggatag gggggcagaa ccatcaaggc tgggtcctgt ggccctcggg gggcggggag    6060
ggactccaga ccacctgcac aaggacagcg ggggcgacac tggcagccct cagagagcct    6120
ctgatgagca acagctcata accaccaata accactccga cacacccggg agagcatggc    6180
tcagtgaggt cacaacttca cgctcggagg acacgggca gacctggcgt tccctgccc     6240 catgtggcct ccgccacccc agagcatgag ccctaccccca cccgagtcct ggcccccact   6300
gggaggtggc catcatggcc cccaatttgc agatggagat ctattaggga atagattggg    6360
gggtgctgct gggaagagaa ttcagctgag acaccaagta agagtccaca aggggagtgg    6420
tttaggaact gtggagtcct gggcccaccc acagcctggg tgtgtggaga gccagagggg    6480 ccctgggca tcttccctg gcgcctacct tccccgactt ggtagaggag ttccggatgc      6540
agtagagtcc atcctggggc tctccccggg ggcttgtagc cttgaacaac ctaaaataag    6600
acagtcatat tagcgggtga gtcctcctcg ggcagctttc acacggacct tcccgccccg    6660
ctcccaagcc tggctttctg ttctctcgct gttgtaggtc tcaggagctg agcacgtcgg    6720
gctgccgtga ggctgacaga agcagcccag cagagccctg ccagccagg gtgccagctg    6780 ggcatgggac agagcaggga ggtccactcc tctggtttct gctgcacgca gggccatgaa    6840
cttgtgccag caactcccca acacggaagc tagtgagagg gacacagaag caggaagccg    6900
ggcatggcgg aggacccagc acacacaggg ctttgtgctg acctttccac ttcgcaggac    6960
tccgtggtgt tgacgaagac cgagttgggc agtggcacct gcaagaggct gacggtgtca    7020
gtgccaacgt cggagtgatc caccgcacc accactcccc ggacggtggc cacccggtgc    7080
cgggatccgg ggctttacat ggtgctgtgt cccctaggc tcccgggttc tcgggggtc     7140 cttgctcagg acggtctgtg aggggccgcc ctggcctatg gctttcccac cacctgtcca    7200
cctactggcc actgggaccc aggcttgccg ctcagccttg ccttctcata gtcctcgtcc    7260
gagtcgtccc cgccagtgtc agcctgtgag ggttgccggg gcttttcaaa ggagaagctc    7320
ctgaaactct gcccatcggg gggtgatcgc ctggaggggc agggagagga aggcaggacc    7380
atttcactgt cagacacggg gcggccaccc tctgctcccc tccccactcc accctctgtg    7440
tgaggacggc aagctgcctg ctatggcccc tgtgacccta aaaagctcag gacaacagag    7500
atccgggtag ggctcgtgct gactgccctg ggacagcagg aatcgcccga caccggagtc    7560
aggggtcagg gctgccatgg atgctggcaa gggagtccag ggttcccaag ctcagtgtca    7620
tcacaccgtc aacaagtgct ctggatgctc gtggggaggg gaggtccggt catggccaaa    7680
tcacagccca ctcagagcca caggggagtg gacgtgaact ggatgaacaa tgcagtgtga    7740
ccccaaagga cgcccatggc gtccctgcac gcctccctgt gtggctagcc ggtcctgctc    7800
agcaaagcct caaaggctct agggaggatt aacgggccac gccagcatgg gaggccagcc    7860
```

```
tgtgggtgag gctgagccct ggaaccgcta tccccacagt catggaaaaa cgtgacttcc    7920
aaacatctgc atctctgcag cccttggtga actagaacca cgagtgtgac aagggctgct    7980
cagaggcact tccacacagg cagcaggcat ctcagaggtg ttcgcagagc cctgggagaa    8040
gggcaccgtg ggcaagggca ttcggggtg cgcgtgccgg ccagcacacc catgcgaaac     8100
ctgcccctcc agttcctgga ccctttgcct gccaggcaag gcaggaagcc cacctggggt    8160
cccagatgcc tttgaccaca gccattggcg taactctgtg ggagtggggg acaaactggt    8220
ctcctggcac ttcccagaaa taaagcagaa agcatttcag caggacgcgg tggctcacgc    8280
ccgtaatctc tacactttga gaggccgagg caggcggatc acttgagacc aggagttcaa    8340
gaccaacctg gccaacatag tgaaacccct gtctctacta aaatacaaa aattagccgg     8400 gcgtgttggc aggtgcctgt agtcccagct acttgggagg ctgaggcagg agaatcacct    8460
gaacccccga ggtggaggtt gcagtgagct gagatcgcac cactgcactc cagcttggtt    8520
gccagcgtga gaccctgtct caaaaagaaa aaaaaacaaa gcatttccag caagcttcag    8580
ggctgagtca tggacatgct ccacgttcca ccaaggcgga ctggaggcaa ccgggaacct    8640 tcctacccctt gcacctggta ccccgtcgtg ggctaagagt gccaggggag cgaggtgggc    8700
agagtgcccg tcagaggcca ggccagggtc cctgtagctg gaggcagggc ttgcagccgc    8760
cacacaaact cactggaggt gcgggagctg cggcttctct ggcctgggca ggactgcggg    8820
ccgcgccatg gcctcaggca ctggcagctt cagcgcagga ggccggggag ccacgggggg    8880
cacaaagagt ccgggcatgg ctgcctccct tgggggtcc tcttcagcta tcttcaggaa     8940
cttgggcttg ttggctggca caggtggggg ctcagatgtg ggtggtcctc gggggacag     9000 gtggaaggac ttgagtttgt cacagtttct ggaggtgcag tggccatgat ggcagcactg    9060
gaagtggagc aggccccgtg gccagggggtc cagggctccg ggctggggct ggcactctcc   9120
cggaagcaag ggggttttccg gaggccgggt gcggtgggca tggtgctcag agggggatcg    9180
ctcatccttc gggggtagc aggtaccctg gggcaaggct cagcccgcct cgggcacagt     9240
gggtccctct tggagtcctc agccgccagg ccaacatctg ggaggccgtg cttagggggc    9300
gggggtggca gtaggggacc ggggcccttg gaggtaaagg agtgggcccg gggcatgtca    9360
gagaaggctg gcttcctggg cgtgggcact ggggtggtg ggtaagccgg tgggtgcatc     9420
agggcatctg cagagcaaag agacccgggt tggaccctga cagagactgg gccaacacta    9480
tcctctgctg gcagtggtca gccaggccaa ccaggagtgc aacccatggt aggcccaccc    9540
cacagcctgc ccacccagca gcccagcacc cagcactccc atcctgcctt ccccagggtc    9600
ccagaccacc caccaccccc agccttcccc attcatcctc cctatggcag cctgtggacg    9660
cttcctgaag cctagaggac acctgaggag cccatcaggt tcccagaggt ggaaggaaga    9720
gaaaggaaga gaagtcaaga aggatctcag ggctcggctg gagcgagagg gaggacggaa    9780
ttcccaagga caggggaggg gagcagctgg gaggaaggtg aaggcccgtg tttgctcaga    9840
acatatccag aaagctggga gatgccaggg gatgcgggt cagggaatgt gtgcagagtt     9900
caaaaatcca ggctggacat gactcggagc gggcagcctg cagatgaccc aggctgtcac    9960
ccagggaatt cggagagga gtgaggtctg agtcccgggt atccctcatg ggccagcac     10020 aggagctgag gagaaagagg accctgggag cacggggcgc ctggaggacg ggctggcaag    10080
gaacagggca ggcgccaggc tggtgtggct caggactgag cgctggaact gggaatgggg    10140
aggccacagg cgtcctggac gagaaatgtc tcggggagag gatgaagggg gtacagaggg    10200
```

```
agggtgagtg gagcagtagc atgcaggagc actggtggct ccccaggccc atctctagcc   10260
tcactgggct gcagctcagg gctgggcaga cggagtctga gttcaccaag gcttggccag   10320
ccaggctaag acggaaggca gtagtgtgtg ggcgaaggga caggcatggt gaacactgtg   10380
agacaagagc tctgcatgga aggaaactga ggcaagcggc ccgcagaccc tggtgggctg   10440
aaggactgtt ggcactggga ccccagaggg aaggagggag ggagcggcag gagaagaggg   10500
gctggacccg ggagcctgaa ggtgggaggg gatgggaggc agagaggata cggggtcagg   10560
ggctggggtc agcagaggcc aagtcagtga gaacaggagg ctggaaaaca aggaggcagg   10620
gcggacgcag ggaaaatgga aggatcaagg atcagcccca gacatgagga aattgacaag   10680 atgaggggc tggagagaca atagggaggg aggaagggag ggaggggaca gaggaggaca   10740
gagacacgtc ctccccaccc agctcgtgct tccgtcatcc acgtgtgacc acctgtatca   10800
gcctgtctct ttgactaggc catgtgctgc aggaggtagg tggacactgg gatgggatgg   10860
ggtggggtgg gacaacgacc tggcctgcag cagtgtccac acaagctggc agccatgggg   10920
acatggacct gccctgagcc tgcgcgctcc tcagcgtcct tccttcccca tgcttaaccc   10980
ccagggccac cccggctcca cctgccactt atcgccatgt gcctgtccct cctcctggga   11040
ggtgggagga ggaaatgagc agaggtggca gcagctacac ctcttctgct ccaatcctca   11100
taatacttgg gacacagcag ggaagcggaa gccacccaga gcggtacctg ggccagcatc   11160
cccagcctgg gaggggctct gctcccggtc ccagcccctg cttcctacac acccagagct   11220
ccccgggccc acccgcccca cctaccctca agccttccgg gctccgggga gtcaggctcc   11280
aggtaggagt catcctcatc gtcgtgctca tagtctgcat ggggagaggg gggtggtgag   11340
agccaaaccg gcccaggccc agtctccgag caatgctcca tgcatggggc tgagtccagg   11400
aggcaagggg caagcacctg ctgggaggac tgtgagtcca gaccctgccg ctgaaggcca   11460
gagcccaggg atgctactgc gcactgccaa agggccagag caaggagcac agccgaacac   11520
acctccctct cctccacagc ggccaagagg aggccaggtg gggagaggcg aacgggcagt   11580
ggatgcggag aaagacctca ccttcattgt ccgtggggta cggggaaagg ctgatatcca   11640
caggccgctc aactgcgccg tagaagctgt ctgtgtccga gctggagtcg ctgcaatgca   11700
gggtgcgttg gggcggacgg tgagcaccag gcctgggagg tcccttgatg ctcacacaaa   11760
ggtacacaca ggcacacgcg gatacatgga cagatacaca gatgcacaca cggatacact   11820
gacaaacaca tgcacacatg gttaagctga cagacacaca catgcacaca cggatccgct   11880
gacagacaca cacatgcaca catggatacg ctgacagaca cacacatgca cacatactct   11940
gacaaacaca caaatgcaca cgtgcacaca caagcacacg caggaacaca ggcacacagg   12000
catggatata tatacacaaa gacacaggga cacgcgcaga catgtagaca cacagacaca   12060
aggactctgt cacacagaca tggaagtata cagataaaca cagatacagg acaagcacac   12120
atgttcacac acagacgagc gacacacgga cacgcacaca caaacacaag caacacgcgg   12180
acatgcacac acacagagca acatgcggac atgcacacac acacagagca acatgaggac   12240
atgcacacac acagagcaac acgtggacat gcacacacac acagagcaac acgcagacat   12300
gcacacacaa acacagagca acacacagac atgcacacac acacagagca acatgcagac   12360
atgcacacac acacacacag agcaaacacg ggacatgcac acacacacag agcaaacacg   12420
agacatgcac acacaaacag caacacgcgg acatgcacac acacagagca acacgcggac   12480
atgcacacac aaacacagag caacacgtgg acatgcacac acacagagca acacgcggac   12540
atgcacacac aaacacagag caacacgcag acatgcacac acaaacacag agcaacacgt   12600
```

```
ggacatgcac acacacacac acagagcaac acgcggacat gcacacacac agagcaacac   12660
gcggacatgc acacacagtt acaaggacag acagaagaac tggaggctgt ggtgcctcca   12720
ctaggtgccc cttctggccc acaaggatgg ccgccctgac tgtgcccacg tctccacctg   12780
ctcctgcctc aagagggctt gggcgactct gggctgggcc cgaggctgaa cagcttggac   12840
caggggacgg gagcccggag tcaggcaggg acctgcaggg cagccttggc tgtgcccagc   12900
cctccctggg cctcctgtcc ccacctgtga aaggacagga aggtttgttc cctccacatc   12960
gtctcgggcc agggagtccc aatccagaga gtatctgctg cacgtcgggc cagctcacgg   13020
gggaggctgc caaggctcag actgcccagt ggcgccccgc caggagaatc attctggtct   13080
cactctgagt gagccagggt gggcgtaggg ggctgggaac ccaaagtgcc cagctgctgc   13140
catgccaggc ctccctggtg gcaggcgtat aaacacacat gatcccctaa caggaactac   13200
ccatggcgga aacacagaaa cagatgtgac agatggggct ggaggtagac aggagcagag   13260
agatgcatgc acacctgtgc atgctctgtg tgtgtgtgca tgtctgtgtg ttgctctgtg   13320
tttgtgtgtg catgtctgcg tgttgctgtg tgtgtgtgca tgtccacgtg ttgctgtgtg   13380
tgtgtgcatg tccacgtgtt gctctgtgtg tgtgtgcatg tccacgtgtt gctctgtgtg   13440
tgtgcatgtc cgcgtgttgc ttgtgttttgt gtgtgcgtgt ccgcgtgtcg ctcgtctgtg   13500
tgtgaacatc tgtgcttgtc ctgtatctgt gtttatctgt agacaggagc agagagacgc   13560
agcccagctg gcacctccag gaaaccttta aggacggaat tctatgccaa gcccggggct   13620
gggaggcgga cacccgggtc aggcccaggc gccccaggga ccctcactgc ccggtatgcc   13680
ctgggcccgg gctcacctgg tgtccaaggg caggtctttc ttttcgtgga agtggccaat   13740
ctccctgcgc agcaaggcca tccagctctg caggtcagcg gggctgtggt gggcacggtg   13800
ccaccagggt gggccccacc gcacccctcc accttcactg ccctgcctgc tctgctgtga   13860
ctcccaaggt cagaggaggc gacccggctg gatacaacat ggctgtgtgg ctcccctcag   13920
cccacagggg cacctcccag gacagcatgt tccttgtgtg ggcgctggca ccaggctctg   13980
ggcatgggga tggagctggg gcagcaccca cccagctgcc tgtgtcccag ccacaccttc   14040
tctttgcccg gggctgagag gccagcgccc caggaccagc gagcccccaa ggcaggtcca   14100
gcctggtgcc tgcaggccca cacccccagt caccttgcac tcgtcctcgg acccccagtc   14160
accttgcgct cctcctcgga ggaggccgag aagaaccacg tgcggtgctt cttgctgatg   14220
tggatgatct tgaagggaa aacgttgttg gacgtggtct cctcagccgc ccgcatcacc   14280
ctgggggcac agcgccaggg gtcacggcct ggttcacagc tatagggatg gccttcccac   14340
agcaccccccc tgtgaacacg tctcggcacc agcaccacgc cccaacgaa ggggcagat   14400
ctgggtgggc cctggctgct gatgctccca gtagtgagct tcatgcccag gcaggcgtaa   14460
gggggcatgg aggggcatgg aagagggggtg ctgggtgggc ttcgtgggag cagcagtgca   14520
caggagacaa ggacaaaacct gcctcgatgc ccgccaatgc cactttacat ggacgccacc   14580
ctcccacctc tggccccatt tgccccaggc ctgcttggcc tccctgggt accсccacagg   14640
gctccgtgcc cctgaggccc agcagcagcc ctgagtgcat tcagggaat gactcgtgcc   14700
tgctctgcgg cccactcaca cagccaggat gtgggtttg cgctgagttt atcacgtggg   14760
gagccctgcc agcaggcac cggggcaggt gcacttatac ggcccataag agcctggcca   14820
aaactcctca ggcccagcat tccctgatgg gctagacaat tccctggggc atgattgcat   14880
ctgccactgg gcccagggtt catggcatgg ctggcacatg ctggaggccg gaaggcgctg   14940
```

```
tgtctgtctg cagaaaggga acgaccttcc ccagggacc ccggagctct gtgccagcat    15000
gggggcctgg caccaggctg ggtgctctgg caaggctgcc ctaccaggcc tgtggccagg    15060
gtgcaggccg gggcctagag tcactccaaa ggtcccagtt ccactactga taccatgtga    15120
cccttggttc ctcataggca ggaggggctg ggcccttaag gggtggtaag aggcatagat    15180
aaatgctgtg gggtgcaggg ctccgatggg atagcaacca gaaccagagc tgggtgccag    15240
cattaaccct ttgtgtgggc cccaggccat gggctgtgcc agtgcactcc cccacccaca    15300
tgccacctgg ccaccgccca cctgcctgtt agtgcagaag ccctccagg gcagctcatg    15360
gcccatcact ggatagagcc cagcccagga catgcgtgaa gctggaaact gatcccggcc    15420
tgggaggacc ctggagcagg gaatcctagg gcccagcctc tgtttgggac agggcctggg    15480
ctggctgggg tctgggctgc ctggaaagag gtcatggtgg gtgaagggc aaggtgggga    15540
gggaggagag atgcagaagt cactgggtgg tggccgagtg gagactctgg agagcaggct    15600
gtccaggcct ctgggacttg tgcacaaagc cacaggaaga ccctggcacc cccaaggtcc    15660
tgcgcctgag ggcaggacac gcggagaggg cgaggcactg tggaggctgg gcggggagga    15720
caggggatgg gcacgaaggc tgcttcggga aagcactttc cttgggcggg aataaggggc    15780
aggcccagct ggggctctgc tgggagggac ccgctggctg tgggggcccg aggtcagcag    15840
gcaggtcggg cacttaccgg ttatagccac tcagggagaa ggcgccctgc ggggaggcag    15900
aggtgctact cttgaagtag tagacgcagc gtttgtggat gatgacaaag cgcaggggcc    15960
ctgtgggagg tggcaagggc aggaaggtga gcctggaggg gcagctgcca agacccactg    16020
tgaggaccct ccacaggaca acttggggcc aggcctcctg cctctaagcc ttaccaaatg    16080
gaagagcagg gagcaaggct ggcatgctgc cccctcccca ggagcccact ctggggccaa    16140
atacggaaaa aattgtaggc acactggcta gccccagagt gccacccgag ggcaggcctg    16200
gctgcccaca aagaagaggt agatttgggg ggctgtgtgg agccagcatg aggcaaggca    16260
gagccaggac cagaggccca gggaggccac agctgacttg ctgggtgctg cagggctgtt    16320
ggaggctccc actaccccag agctaaaaga gggggactaa ggccgggtgc agtggctcac    16380
gcctgcgatc ccagctactc aggaggctga agcaggagaa ttgcttgaac ccgggagtca    16440
gaggttgcag tgagccaaga tcgtgctact gcactccagc ctgggtgaca agagtgagac    16500
tgtctctaaa aataaaagat ggggtgagcc tgagcaacat gtgaaacccc atctctacaa    16560
aaaatacaaa acttagccgg acacggtggc atacatctgt agttccagct acttgggagg    16620
ctgaggtggg aggatcattt gagcccagga ggtcgaggct gcagtgagct gtgttcgcac    16680
ccactgcact gcagtctggg tgacagagtg agacataaaa ataataaata ggccaggcgc    16740
ggtggctcat gcctgtaatc ccagaacttt aggaggccaa gacaggatca cttgaagtca    16800
ggagttcgag accaggctga ccaacatggt gaaacgctgt ctctactaaa aatacaaaaa    16860
ttagctgggc gtggtggcac actcctgtaa tcccagctac tcaggaggct gaggcaggag    16920
aattgctgga acccaggagg tggacgttac agtgagctga gatcaagtca ctgcactcca    16980
gcctgggcaa cagagcaaga ctccatctca aaaaataaaa taaataaaaa acaaaaataa    17040
ataaaaaata ggctggatgc ggtggctcac acctgtaatc ccagcacttt gggagaccaa    17100
ggcggatgga tcgcttgagc tcaggagctc caggccagcc tggcaacat aatgaaattc    17160
catctctaca agaaatttaa aaaaaaatta acagggcata gtggcatgcc tgtagtccca    17220
gctgagggga tcacctgagc ctgggaggtt gaggctgcag tgagccatga tcacgccact    17280
acactccagc ttgggcaaca gagcaagacc ctgtctcgaa aaataaaat aaaagaggga    17340
```

```
gactcaggag cccggagagt tgccagtga gagccactgg tgtggggcca cccctaggtg   17400
gaaagttaca ctgaaaccac cctagctcca ctgccccagc cctgtcccag gctgggggac   17460
aagccagtta cagctcctcc aaggaggctg tctgtgcaaa gaggagaaca gctcaaccag   17520
tgcccgtaca ggaaccaatc agtccagcct ggacatctca accaggcggc ccaggaccag   17580
ggagtccctg gcagagggca ctgctactgc aaaggcatgg agcacctgct gctcaggccc   17640
tgatgctctt ggccttcagt atctcagcat ttgggtatct ctcaagcctg agggctgctt   17700
cttcctccca gccagctgtc ctgggggcca gagcctgggt cttgtgcagc tccagaggtc   17760
cagcacccag ccaggacttg acacataggt tcactgtggg cgaagtgacc aactaactca   17820
ctgaacattc acggattcag tgagggcagc accagaggcc agacctacct ggccacctgt   17880
ggtccccagg tcctggctgc aggctgcagc tccccttgcc agctggccag cactgtgcac   17940
caccccggac cctgctacag tcctgggggc tagggaagtc aacctctgct tctccagggg   18000
tgccagccac cagagaggga atgggaaaat ccagagggca caccatgtga ggaagcagag   18060
gcttggagag gatgcttact tacatggcta gccctgcccc catgccctcc tactgtgcac   18120
cctaccaccc cagggactca catttcagca gctgaagctg gtaccgcccc ttcttgtgca   18180
ggtagccagc cttggccacg ccccaggca tggttagcag gttctgggca ccaatggcct   18240
tcatagggac aggccaatgc atctcttcag ccgccatgaa gctgcaataa aggacaaagg   18300
cacgtggctc agctacggtc aggcaggaga tgtctgagcc agggcgctca ggggacact   18360 gccaagatcc aggacacagc ttggagggta gggccatgac aggcaaggaa acccttttc   18420 tgagggcctt gggcttccag gtgggacccc agggagagac agagccacgg gctccactca   18480 gtcagccct ggtccactca gccacaaacc caacccagg atcctgagcg ctacgtgcag   18540 cccttctct ccactggttc attctgcaca cagccactga gcgcaaggcc cacgggggc   18600 tgggtagaga tgaacgaact cagaaaactg ccagcccagg taagtgagac ctcaggccat   18660
aactacttca gtcccagtg ccaggtgaac ctataagggg cctagacagg aagaaggcaa   18720 gtgagcagc aagagcaccc agctcaaacg acctgggctc ccatcctggt gtgactttct   18780
gggagatccc aagcctcaga tgctggagga cagagtggac acccagccca gcacacagca   18840
cactgttgtc agcagtggtc gtgaccacca tttggtgggt tggctgctat ccaccccacc   18900
agcccaggat atcactcccc ttccctctga gccaagcga ggaccacaca gtcagtggag   18960
gaccagtgac tgccttgggg ctaacccagg cccacaggac ccaacatcat gccctgcccc   19020
ctactccagc cccccttact catgctccag ctgctctcct tgagatacac catgctgttt   19080
aatgcttcct cctctgcctg aaatgacctc caccccttcc catgcagaga acttctactc   19140
atccatcaag acccaggtta agagcccctc ttctgctagg caccctcatt gcccacttaa   19200
atccagcatc ttcctcatct cttgtcccag tgaacagtac ccccgaccc tgcactgttt   19260 ggtctgtgcc tgccctcact ccatcctggg tagggtccct cctgtggccc cagtggagtt   19320
ggatgggagc aggcctgtgg ccagtgtcct gttaagccct tagtggagca gctaaggtca   19380
gacccagatg cccagtgggg ctgggactgg ttccactaca gctccaaccc caaaaaacat   19440
acataaagaa aactaagcca gggcaacata gcaagaccct atctctaaaa aaaaattttt   19500
ttttaattag tcaggcatgg tggggtgcat ctgtagtccc agctgctcta ggaggctgag   19560
gcaggaggat cacttgagcc caggagtttg aggctgcagt ggtctatgat cgtaccactg   19620
cactccagcc tgggcaacaa agtgagacac tgtctctata aataaataaa atagccggac   19680
```

```
gcagtggctc acgcctgtaa tcccagcact ttgggaggcc aaggcaggcg gatcacttga   19740
gctcaggcgt tcaaggcctg cctgggcaac atatagagac aaccatctct aaaaaataat   19800
tagctgagct tggtggtgca cacctatagt acccggagga ggcttatcca ggaggatcga   19860
ttgagccagg agttccagga ggcagtaagc tatgattggc cactgctctc cagtctgggc   19920
aactgagctg gagctaaaat taaaaaatta aaacaaaat aaataaaaag aaaaatactc   19980 tctgcttta gcaaaccagc accctccaac aaaagtgcaa gaggaagtct tcaaggcatc   20040
aggctgtctt ctgccggcct cggcctgggt cacccggctg accccacca gctccttctg   20100 cacccaaaga cagcccctct gggcaggag gggtcagggg cgggtcccag ccgcaggacc   20160
cccaaccaca ggccaaggtt tggaacaaag gcgccgccac accccgccgc ccgcccaacc   20220
gcgcccggcc cgaaggagcc ccgcagtggg gatggaggag ggagcccgt gcccagtccg   20280 cccgcgggga gctgcccgca gatcgacaag ccccgtgccg gcctgagtcc cccatccgcc   20340
cgccgggacg gtccacgccc gcctttgttc ccccaagaag cgcgtgggcg accagcagcg   20400
cccggggctc gcggcctggt ccaggggctc ggggtgcggg gtccagagcc ggaagctcgc   20460
ggcccgggtc ccggggctcg ggggccgggg ctcggtactc acgcgtcca cgcggcgggc   20520 atggccggct tccccggggc gatccacgcc cgcctcccct gcgagcaccg gcacggcccc   20580
gggccgcgtc cccggccgc cgccgcctcg tcccgggcgc ccgcctcccg ccggcccag   20640 ctccgcggcg cggccggag cccgccatgc ccgccggccc tggcctggca gccgccggct   20700
cctcccctct cggcggggga ctgggcggcc aggtgaggat cccggcgcgc ccctcccggc   20760 cccgcccct gccgcgtcac cgtgcgcggg aggcacgtga gccccctgcg ggcctcagtt   20820
tccccacgct gcaaggaggt tggtgggcgc ttgggacagg aggcccacat ctgttggtgc   20880
agcctggaat caagaagcct tcgatgcaaa cgaggcctcc cgctccactc ccccaacacc   20940
tgccagtcca cacagcttgg ttggaaatcc acgccggcg cgggagcctc ggctctgagg   21000
ccccgcccag gtcccatccc gccgggccct tgcaaccagc tccctcggga aagtggcctc   21060
tgcaaaacgg cacctgcatg gagggcggca acggggcaag ggatcgggca cgtgccccgc   21120
cctcaccttc tccactttcc tgcgggactc catgggcctc cagccccgga ttctccaagg   21180
agccaggggt ctggtccttg gcacctccca cctgcttgcc caaacgcagg cacctcaccc   21240
aggagagtcc cctggggtgg ccaaaggccg gcagaggccc ttgctggcct cccaggcatc   21300
ctgcctcctc catcttccac ctgcaaacaa gctgccacca agatgggcca gatgcaggtg   21360
tggctctaac agcctgggcc tgaccctacc tagctgtcca tcctgggcac ccaccctggt   21420
ttcaaggccc cacctcaggc ccgctatctg gacttcttcc cactgcaccc agccttcgag   21480
gctctgtccc atctctgtgc ctctgttctc agtgcccttg tctggcctgc ctcaaggatc   21540
ccacctcctt ccagctgccc tgccaggccc ctctccattg cctcttggca acccctcca   21600 cttcctctcc tcaggcttcc tctgcctcca gcccctcca cccagcacag aatcaacacg   21660
cacaccattc ccatcactgc tcagtgctaa acctctaggg cctcctcatg ccaacctggc   21720
ccttcctgat tcagccactc ctgccctcta ccttctgtgc tcttacgcca gccagaccct   21780
atggctccag ttacctgaat cgagcaagca cccacttgca ggcctcagcc cctgctgttg   21840
ccacagccta aagttgaaac tgaactaacc cagccatcaa gagttggctc aaaagaacat   21900
ggatccttca caaacttcca gaaaatagaa gaggagggaa ctcattctat gagagcagca   21960
ttatcccaat accaaaacca gacaaagaca tcacaataaa actacaaacc aatatccctt   22020
atgggtatag acataaacat cctcaacaaa atactggcca actgaatcct gcaacatata   22080
```

| | | | | | |
|---|---|---|---|---|---|
| aagggattc | tacaccaaga | ccatgtggga | tttatcccag | gaatacaagg | atggcttaat | 22140 |
| attcaaaaca | attaatgtaa | tacaccatat | caatagaata | aaggacaacc | acatgatttt | 22200 |
| gatagacgaa | gaacaagtgt | ttgacaaaat | tcaacactcc | tccatgataa | gaacagtcaa | 22260 |
| caaaccagga | atagaaggga | agttcctcaa | tctgataaag | ggttctatga | aaacccaca | 22320 |
| gctaacatac | ctagtggtaa | aagactgaaa | gtttttcccc | caagaacagg | aacaaggaaa | 22380 |
| ggatgtctgc | tctacttcta | ttcagcatag | tactggagat | tctcaccaga | gtaattaggc | 22440 |
| aataaaaaga | aataaaaggt | atccagaatg | gaaagaaaga | acaattattc | actgattaga | 22500 |
| ttattttaca | tacagaaaat | cccaaggaat | ccacttaaaa | attattagaa | tagccatgcg | 22560 |
| cagtggctca | cgcctgtaat | cccagcactt | tgggaggctg | aggcgggcag | atcacctgag | 22620 |
| gtcaggagtt | cgagaccagc | gtggccaaca | tggtgaaacc | cccatttcta | ctaaaaatac | 22680 |
| caggtggcag | gcacctgtaa | tcccagctat | ttgggaggct | gaggcaggag | aatcgcttga | 22740 |
| acccgggagg | tggaggtagc | agtgagccga | gattgcgcca | ttgcactcca | gcctgggaa | 22800 |
| caagaatgag | acttcatctc | aaaaaaaaaa | aattattaga | ataaatgagc | agcaaggtgg | 22860 |
| caggatataa | gatcaacata | caaaaatcaa | ttctatttct | atatactagc | aacaatccaa | 22920 |
| aaatgaaagg | aagagttagt | tcaagcgttc | ccttttccag | gcagtctccc | | 22970 |

<210> SEQ ID NO 26
<211> LENGTH: 22970
<212> TYPE: DNA
<213> ORGANISM: homo sapiens
<220> FEATURE:
<221> NAME/KEY: misc_feature
<222> LOCATION: (7332)..(7334)
<223> OTHER INFORMATION: n = C, T, G or A
    provided that the mutant domain is not wild type
<220> FEATURE:
<221> NAME/KEY: misc_feature
<222> LOCATION: (7338)..(7340)
<223> OTHER INFORMATION: n = C, T, G or A
    provided that the mutant domain is not wild type
<220> FEATURE:
<221> NAME/KEY: misc_feature
<222> LOCATION: (7347)..(7349)
<223> OTHER INFORMATION: n = C, T, G or A
    provided that the mutant domain is not wild type

<400> SEQUENCE: 26

| | | | | | |
|---|---|---|---|---|---|
| gatcttcata | ccctagaacc | caggagtcag | actcctgagt | acaaaccta | gaaaatttg | 60 |
| tgcaccattt | gcaaaaaaca | cacgtgcatc | agagacatgg | acaaaactgt | tgctagcagc | 120 |
| attgtgtgta | gttaccccaa | actagaaaca | aaccaactgt | ccatctacag | caggcatgtc | 180 |
| caatcttttg | gcttccatgg | accataccgg | aagaactgtc | tcgggtcacg | cataaaatac | 240 |
| actaccacta | actatagctg | atgagctaaa | aaaaaaaaat | cgcaaacaaa | aatctttata | 300 |
| atgtttaag | aaagtttaca | aatttgtgtt | gggccacatt | caaaggcatc | ctgggctgca | 360 |
| tgcattggac | aagcttgact | gacagtgaaa | tgaatctgtg | aactacgata | cagccaaaca | 420 |
| atggaagttt | ttagcaatga | acatgcacaa | actatactac | gcacagcaac | atgaataaat | 480 |
| ctcacagaca | taataacgag | ccaaagaagc | cagctgccag | aatttgcatc | tgtatgattc | 540 |
| aaggggataa | agcacagaaa | caggaaaata | ctgcaatgcc | tgcataattg | ggtgctgaag | 600 |
| acttttaga | aaaacaagaa | cacaagactc | acataagcca | gggcagagag | gccggaagtg | 660 |
| acactgtgag | gggagggcac | ttgggtgctg | gcaaaactat | ttcctgatgg | tggttgcaga | 720 |
| tcgttcactt | cctaacagtg | tgttaggttg | tgcatttatg | ttttattcac | ttttctgtat | 780 |

```
gttgttttat tctgcaggaa atgaatgaaa aagggattct gcctcagctc tgagcccctc    840
agagtggggc cagggaagaa gcagacggca acgccagggc agctgtctgg cagcctggaa    900
ggcctgcgaa gcttcctagg ggtccgaagg agggtagaca ggtaggggtc tgctctgtac    960
ccatcaaatc tccctccagt gagaatggtt ggaagatggc ttaaaagggt tcaccactca   1020
cacacacttc tgaggtggtg ggggttgtct gtcaagcatc ttcacaggg  cactgcccct   1080 cttcccaag dacaggcaac ctcctggcac tgccccctca gcaggcagtc taggtggagg    1140
gaacagggcg tgcaggcaga gataaggcag ggggtgtgtg cgaggtgccc agcgaggggc    1200
ttgatgctgc tgggtcacag aaacagaggt tgtggcccct cccccattcc cctcgtctag   1260
agacaagcac ggccctccca tgttcctggt gtgaccctgg tgtcctaggc catccctcca   1320
gcgcctggat caccctcaaa agcctcttcc ctgctgagct tcaatctgcc tttctatgaa   1380
atggccccaa taagccctgc ctgcctcagg gaactaagcc gcaggtccca ggtcccctc    1440 tcccccaatg cccacccteg cccatcctga ggtgcaggaa gcacctccct ggggctgcgc   1500
tgagccccaa ccagcagggg agctccgcac aacgtggccc agaaggatca gtgggaaccg   1560
aggtttcttc tggttctaaa aacatctttt caaggctggg cgccgtggct cgcgcctgta   1620
atcccagcac ttgggaggcc aaggtgggcg gatcagttga ggtcaggagt tcaagaccag   1680
cctggccaac atggtgaaac cccggttcca ctaaaaatac aaaaatttgg caggcagctg   1740
taatcccagc tacatgggag ggtgaggcag gagaatcgat tgaaccctgg agatttgcat   1800
tgagccgaga tcacgccaat ccactctagc ctgggcgaca gagtgagact gtgtcccaaa   1860 aaaaaagaa aaaatctttt cacaatacaa atctttatta actgaaggca cggggctcac   1920
cacaatcctt cggatggaac cacaggaaga gaagaagcat gtttcaccct gggctggggg   1980
tgcttcccaa agccactggg gccctttttcc caagcccag aactgagccc acctgaactc    2040
atcttgaagg taggtatgtc agtgagtcct cccaaagcct cagtttccct atctataaaa   2100
tgaggaagca ggactgcccc tagggcaagg cctaggcctc ctgccagccc accctcacag   2160
acccagaggg caacacaggg tgaggcgggg cagtttcact ccccagtgct gtggccccct   2220
tggttgagtg aaagcaccte cagagcccta accctagccc tgggagccag gcaagagacc   2280
cccacaacga ccatcagagg tcgtgagggg tggcagggag cctggcaggg agccaggcag   2340
gggccagggt ctaggctcag agcagtgaag gatagatagg gtcacatgcc agttagtggc   2400
agaggtggga cttgaaccca ggcctctgtg agacttggtt ctctcacctg taaaatgggt   2460
ctactagcag ctgcttctcc aagcaaatga tgtcaagcac ccagctcggc acctcacaga   2520
tgtggtcagt aaatggtaat cccaaccta cccttatatg tggactagaa cacttatggc    2580
aagtctcggg aggtcatggg aactcctcat ggctccttct tcatgctgga ggaccacggc   2640
ctgccccatc ccaccccaac acactcttga aactgaggcc ctcggcctag agcagctcac   2700
acagacgtgg acagctgtgc tagcaggtgc agagtctggg aggcgaggct ggaccagggc   2760
cccagctggg cttcgggtaa ccacaggcct caactgtcca gttggccaga gggacctatc   2820
acctggctct gggcccagg  atgctttagc cacttgagcc ggctccaggt gaccgtgtaa   2880
gtgagataaa gcaaaggtgt cctggactgc accactcact agctcagcac cccaggcacc   2940
aggctggaaa ccacatctcg cacccaattc tccatttaaa aattttacag gaaggggcca   3000
ggcacagtgg ctcatgcctg taatcccagc actttgggag gccaaggtgg gcagatcacc   3060
tgaggtcagg agttcgagac cagcctggcc aacatgataa aatcccgtct ctactaaaaa   3120
```

```
tacaaaaaat tagccaggcg tggtggcggg cgcctggaat cccagctact cggaggctg     3180 aggcaggaaa atcgcttgaa ctagagaggc ggaggtggca gtgagcggag atcacggcat     3240
tgcactccag cctgggcgac agggtgagac tacatctcaa aaacaaaaaa ctaaaataat     3300
aaaattttac aggaagagaa actatggcca cagtggggag tggcatgact ccctaagcaa     3360
gttcaggtca gacagggcaa agaattctga ctgcagggag gaggaatggc tggttttcca     3420
gagatagatc agaacaacag aagctccctg tgctccagcc tcggctgtgg tgcactgacc     3480
tctcacccca ggcaggctga agaggaaacc cctgcagagg tggccttgga cacctggttc     3540
ctggaagcag ctggctgccg tcatctgcag ggcctgcagt tccaccgcac cctatggccc     3600
ctggggtcac agcctcccac atccgctaac cagcctcatc acttgtttcc gccagcaaac     3660
cacaggtccc cagaacacac caggggaag ggggctgcag gaccttctcc cccagtcagt     3720
cactgtcagt gggcccaagt gctgacctca gtttaggttt ccctgacata aggtgctaag     3780
aaaaatcaca aggattctag ggtccctgcc agccctacc tccctgagtc tgtttcatta     3840
aaaatccagc ctggaaggtg tgccagggag agtgacctgc tggaactcca tggcagaaag     3900
taaggggatg gattggggct gggcctgagc caggtattgc ctggaagact tgggcatctg     3960
ggtaccaccg tccctacgca cccttggcct gcttagggtc cactgttccc atcccatcat     4020
agctgttact tcctccaaaa aatcttccgg gagcccccag tccctgcaca cccagctgcc     4080
ctggacactg tgccgtaagc acctcatacc cagctgtccc cagactgggc tgtgaactca     4140
gccaggccag aggcccctgt ctggaatggg accaggcatg caggaggtac caataactg     4200 ctcgctaatg cagggaatga agcagctgta gctgcagggc cttctagctc tgtagcccgc     4260
tcagtgtatg caagttctgg aacggggaca gccactcagg aggtacccag taaccaggca     4320
ctaatgcagg gaatgaagca gctgtagctg cagggccttc tagctctgca gcagcactgc     4380
cctggcctga cctgaggcag cagaactggt gagtggggtg tgggctccca gcccagactg     4440
cccaagtttg ggtcctgatc tgttactcgc tgtgcaccct ggggaagtca ctcagtgacc     4500
tgcaccctgg aagacaagac aaccaactgt tggggttccc gggtactgct gcggtcacca     4560
cttagacatc agcatgggca cccagtaagc tggtaatccc ctccttccca atcaagcccc     4620
agccaccaag gcaaagctca ctgctgcttt attggaggca acagccccta ctggagcctg     4680
tgtcttagcg ttcctggggg tcccagggcc agccccggcc cccacccagc tgccctggcc     4740
ctgcctggct cccagcccac ttaggggtga gtgtgatggg gggaccagtg ttcctgtcct     4800
tggagcccag gcacagcttg gtcctgggtt tctgggattg gacagggca agttagtgtg     4860 gggcaacaga gtcccttcgt cctctggagc ctggcgcctg gttcagccct agaacccaac     4920
ctgctggatg agactggctg gtcctacga gatgtccatc acagaggccc taggcaagca     4980
cagccttgct cctgctcacc ctcccatgtg ggcccatgtc cgtctgtgtg cctggggtc     5040 agggcccctg tgactgcctt ggcctggcag ccacatggac tgccatcacc taggcccagt     5100
gtagccgtag gggtgccgca gcagcaggct ctggtggctg gcagcacgt gggtgtggta     5160 gtgctcccac catgctgccc acactcacaa acaggacctc gccctccagg tagaacttag     5220
agtcctgtgg gggaagagaa gggggagcgt cagcagggcc aggccactct gcggctctag     5280
gcctcagtct cccgtctgt aaaacaaggc agcagcatca acagcggcat caccaggctg     5340
gcccctggct gtcggtggtg cccccaaggt ggcctccgca tcaggcctgt gctctccatg     5400
ttcccacctc acttccctc cgtcctccat gtccaggagc tgcacccag agcacttcag     5460 acaaggtcag gaaatgaacc taggccaggc acggtggccc acgcctgtaa tcccagcact     5520
```

```
gtgggaggcc gaggtgggag gattgcttga gccccagaat ttgaaaccag cctgagaaag    5580
acagtgagac ccctgtcccc gcaaaaagaa aaagacaaga caagcaaccc agggtctatg    5640
gctgaccgcc catccccact agggtcagtg gaggacaaag gtaggccacg agaggaggga    5700
ggctgagcag gaggggtggg gggtgagcga tggtggaggg aagggggagg gcggtatcct    5760
ggaggtgcca gtctcagtct acccgctgcc tatgcctcat cagggagatt ctgccctgcc    5820
ccttgccagg ccatgcggcc agggtccccg tcccactcag agccctctca ccttctcaaa    5880
aatgcgatag ttcctcactt tgttagaggt ttcgtcccac acaaccagga cctacaggac    5940
ggaagcggga ggctgacggc tccctgagaa acagcgggac cagcctcggg agaccatggg    6000
ctggggatag gggggcagaa ccatcaaggc tgggtcctgt ggcctcgggg ggcggggag     6060 ggactccaga ccacctgcac aaggacagcg ggggcgacac tggcagccct cagagagcct    6120
ctgatgagca acagctcata accaccaata accactccga cacacccggg agagcatggc    6180
tcagtgaggt cacaacttca cgctcggagg gacacgggca gacctggcgt tcccctgccc    6240
catgtggcct ccgccacccc agagcatgag ccctacccca cccgagtcct ggcccccact    6300
gggaggtggc catcatggcc cccaatttgc agatggagat ctattaggga atagattggg    6360
gggtgctgct gggaagagaa ttcagctgag acaccaagta agagtccaca aggggagtgg    6420
tttaggaact gtggagtcct gggcccaccc acagcctggg tgtgtggaga gccagagggg    6480
ccctggggca tcttcccctg gcgcctacct tccccgactt ggtagaggag ttccggatgc    6540
agtagagtcc atcctggggc tctccccggg ggcttgtagc cttgaacaac ctaaaataag    6600
acagtcatat tagcgggtga gtcctcctcg ggcagctttc acacggacct tcccgccccg    6660
ctcccaagcc tggcttttctg ttctctcgct gttgtaggtc tcaggagctg agcacgtcgg    6720
gctgccgtga ggctgacaga agcagcccag cagagccctg ccagccagg gtgccagctg     6780 ggcatgggac agagcaggga ggtccactcc tctggtttct gctgcacgca gggccatgaa    6840
cttgtgccag caactcccca acacggaagc tagtgagagg gacacagaag caggaagccg    6900
ggcatggcgg aggacccagc acacacaggg ctttgtgctg acctttccac ttcgcaggac    6960
tccgtggtgt tgacgaagac cgagttgggc agtggcacct gcaagaggct gacggtgtca    7020
gtgccaacgt cggagtgatc cacccgcacc accactcccc ggacggtggc cacccggtgc    7080
cgggatccgg ggctttacat ggtgctgtgt cccctaggc tcccgggttc tcgggggtc     7140 cttgctcagg acggtctgtg aggggccgcc ctggcctatg gctttccac cacctgtcca    7200 cctactggcc actgggaccc aggcttgccg ctcagccttg ccttctcata gtcctcgtcc    7260
gagtcgtccc cgccagtgtc agcctgtgag ggttgccggg gcttttcaaa ggagaagctc    7320
ctgaaactct gnnnatcnnn gggtgannnc ctggagggc agggagagga aggcaggacc    7380
atttcactgt cagacacggg gcggccaccc tctgctcccc tccccactcc accctctgtg    7440
tgaggacggc aagctgcctg ctatggcccc tgtgacccta aaaagctcag acaacagag     7500 atccgggtag ggctcgtgct gactgccctg ggacagcagg aatcgcccga caccggagtc    7560
aggggtcagg gctgccatgg atgctggcaa gggagtccag ggttcccaag ctcagtgtca    7620
tcacaccgtc aacaagtgct ctggatgctg gtggggaggg gaggtccggt catggccaaa    7680
tcacagccca ctcagagcca caggggagtg gacgtgaact ggatgaacaa tgcagtgtga    7740
ccccaaagga cgcccatggc gtccctgcac gcctccctgt gtggctagcc ggtcctgctc    7800
agcaaagcct caaaggctct agggaggatt aacgggccac gccagcatgg gaggccagcc    7860
```

```
tgtgggtgag gctgagccct ggaaccgcta tccccacagt catggaaaaa cgtgacttcc      7920
aaacatctgc atctctgcag cccttggtga actagaacca cgagtgtgac aagggctgct      7980
cagaggcact tccacacagg cagcaggcat ctcagaggtg ttcgcagagc cctgggagaa      8040
gggcaccgtg ggcaagggca ttcggggggtg cgcgtgccgg ccagcacacc catgcgaaac     8100
ctgcccctcc agttcctgga ccctttgcct gccaggcaag gcaggaagcc cacctgggt      8160
cccagatgcc tttgaccaca gccattggcg taactctgtg ggagtggggg acaaactggt     8220
ctcctggcac ttcccagaaa taaagcagaa agcatttcag caggacgcgg tggctcacgc     8280
ccgtaatctc tacactttga gaggccgagg caggcggatc acttgagacc aggagttcaa     8340
gaccaacctg gccaacatag tgaaaccct gtctctacta aaaatacaaa aattagccgg      8400
gcgtgttggc aggtgcctgt agtcccagct acttgggagg ctgaggcagg agaatcacct     8460
gaacccggga ggtggaggtt gcagtgagct gagatcgcac cactgcactc cagcttggtt     8520
gccagcgtga ccctgtctc caaaaagaaa aaaaacaaa gcatttccag caagcttcag       8580
ggctgagtca tggacatgct ccacgttcca ccaaggcgga ctggaggcaa ccgggaacct     8640
tcctacccctt gcacctggta ccccgtcgtg ggctaagagt gccaggggag cgaggtgggc    8700
agagtgcccg tcagaggcca ggccagggtc cctgtagctg gaggcagggc ttgcagccgc     8760
cacacaaact cactgaggt gcgggagctg cggcttctct ggcctgggca ggactgcggg      8820
ccgcgccatg gcctcaggca ctggcagctt cagcgcagga ggccggggag ccacgggggg     8880
cacaaagagt ccgggcatgg ctgcctccct tgggggtcc tcttcagcta tcttcaggaa      8940
cttgggcttg ttggctggca caggtggggg ctcagatgtg ggtggtcctc ggggggacag     9000
gtggaaggac ttgagtttgt cacagtttct ggaggtgcag tggccatgat ggcagcactg     9060
gaagtggagc aggccccgtg ccagggggtc cagggctccg ggctggggct ggcactctcc     9120
cggaagcaag ggggtttccg gaggccgggt gcggtgggca tggtgctcag aggggggatcg    9180
ctcatccttc ggggggtagc aggtaccctg gggcaaggct cagcccgcct cgggcacagt     9240
gggtccctct tggagtcctc agccgccagg ccaacatctg ggaggccgtg cttaggggc      9300
ggggggtggca gtaggggacc ggggcccttg gaggtaaagg agtgggcccg gggcatgtca    9360
gagaaggctg gcttcctggg cgtgggcact ggggggtggtg ggtaagccgg tgggtgcatc    9420
agggcatctg cagagcaaag agacccgggt tggaccctga cagagactgg gccaacacta    9480
tcctctgctg gcagtggtca gccaggccaa ccaggagtgc aacccatggt aggcccaccc    9540
cacagcctgc ccacccagca gcccagcacc cagcactccc atcctgcctt ccccagggtc    9600
ccagaccacc caccaccccc agccttcccc attcatcctc cctatggcag cctgtggacg     9660
cttcctgaag cctagaggac acctgaggag cccatcaggt tccagaggt ggaaggaaga     9720
gaaaggaaga gaagtcaaga aggatctcag ggctcggctg gagcgagagg gaggacggaa    9780
ttcccaagga caggggaggg gagcagctgg gaggaaggtg aaggcccgtg tttgctcaga    9840
acatatccag aaagctggga gatgccaggg gatgcggggt cagggaatgt gtgcagagtt    9900
caaaaatcca ggctggacat gactcggagc gggcagcctg cagatgaccc aggctgtcac     9960
ccagggaatt cgggagagga gtgaggtctg agtcccgggt atccctcatg gggccagcac    10020
aggagctgag gagaaagagg accctgggag cacggggcgc ctgaggacg ggctggcaag      10080
gaacagggca ggcgccaggc tggtgtggct caggactgag cgctggaact gggaatgggg    10140
aggccacagg cgtcctggac gagaaatgtc tcggggagag gatgaagggg gtacagaggg    10200
agggtgagtg gagcagtagc atgcaggagc actggtggct ccccaggccc atctctagcc    10260
```

-continued

```
tcactgggct gcagctcagg gctgggcaga cggagtctga gttcaccaag gcttggccag    10320
ccaggctaag acggaaggca gtagtgtgtg ggcgaaggga caggcatggt gaacactgtg    10380
agacaagagc tctgcatgga aggaaactga ggcaagcggc ccgcagaccc tggtgggctg    10440
aaggactgtt ggcactggga ccccagaggg aaggagggag ggagcggcag agaagaggg    10500 gctggacccg ggagcctgaa ggtgggaggg gatgggaggc agagaggata cggggtcagg    10560
ggctggggtc agcagaggcc aagtcagtga aacaggagg ctggaaaaca aggaggcagg    10620
gcggacgcag ggaaaatgga aggatcaagg atcagcccca gacatgagga aattgacaag    10680 atgaggggc tggagagaca atagggaggg aggaaggag ggaggggaca gaggaggaca    10740
gagacacgtc ctccccaccc agctcgtgct tccgtcatcc acgtgtgacc acctgtatca    10800
gcctgtctct ttgactaggc catgtgctgc aggaggtagg tggacactgg gatgggatgg    10860
ggtggggtgg gacaacgacc tggcctgcag cagtgtccac acaagctggc agccatgggg    10920
acatggacct gccctgagcc tgcgcgctcc tcagcgtcct tccttcccca tgcttaaccc    10980
ccagggccac cccggctcca cctgccactt atcgccatgt gcctgtccct cctcctggga    11040
ggtgggagga ggaaatgagc agaggtggca gcagctacac ctcttctgct ccaatcctca    11100
taatacttgg gacacagcag ggaagcggaa gccacccaga gcggtacctg gccagcatc    11160 cccagcctgg gagggctct gctcccggtc ccagcccctg cttcctacac acccagagct    11220
ccccgggccc acccgcccca cctaccctca agccttccgg gctccgggga gtcaggctcc    11280
aggtaggagt catcctcatc gtcgtgctca tagtctgcat ggggagaggg gggtggtgag    11340
agccaaaccg gcccaggccc agtctccgag caatgctcca tgcatggggc tgagtccagg    11400
aggcaagggg caagcacctg ctgggaggac tgtgagtcca gaccctgccg ctgaaggcca    11460
gagcccaggg atgctactgc gcactgccaa agggccagag caaggagcac agccgaacac    11520
acctccctct cctccacagc ggccaagagg aggccaggtg gggagaggcg aacgggcagt    11580
ggatgcggag aaagacctca ccttcattgt ccgtggggta cggggaaagg ctgatatcca    11640
caggccgctc aactgcgccg tagaagctgt ctgtgtccga gctggagtcg ctgcaatgca    11700
gggtgcgttg gggcggacgg tgagcaccag gcctgggagg tcccttgatg ctcacacaaa    11760
ggtacacaca ggcacacgcg gatacatgga cagatacaca gatgcacaca cggatacact    11820
gacaaacaca tgcacacatg gttaagctga cagacacaca catgcacaca cggatccgct    11880
gacagacaca cacatgcaca catggatacg ctgacagaca cacacatgca cacatactct    11940
gacaaacaca caaatgcaca cgtgcacaca caagcacacg caggaacaca ggcacacagg    12000
catggatata tatacacaaa gacacaggga cacgcgcaga catgtagaca cacagacaca    12060
aggactctgt cacacagaca tggaagtata cagataaaca cagatacagg acaagcacac    12120
atgttcacac acagacgagc gacacacgga cacgcacaca caaacacaag caacacgcgg    12180
acatgcacac acacagagca acatgcggac atgcacacac acagagcaca catgaggac    12240 atgcacacac acagagcaac acgtggacat gcacacacac agagcaacac gcagacat    12300 gcacacacaa acacagagca acacacagac atgcacacac acagagcaca catgcagac    12360 atgcacacac acacacag agcaacacgc ggacatgcac acacacag agcaacacgc    12420 agacatgcac acacaaacag caacacgcgg acatgcacac acacagagca cacgcggac    12480 atgcacacac aaacacagag caacacgtgg acatgcacac acacagagca cacgcggac    12540 atgcacacac aaacacagag caacacgcag acatgcacac acaaacacag agcaacacgt    12600
```

```
ggacatgcac acacacacac acagagcaac acgcggacat gcacacacac agagcaacac   12660
gcggacatgc acacacagtt acaaggacag acagaagaac tggaggctgt ggtgcctcca   12720
ctaggtgccc cttctggccc acaaggatgg ccgccctgac tgtgcccacg tctccacctg   12780
ctcctgcctc aagagggctt gggcgactct gggctgggcc cgaggctgaa cagcttggac   12840
caggggacgg gagcccggag tcaggcaggg acctgcaggg cagccttggc tgtgcccagc   12900
cctccctggg cctcctgtcc ccacctgtga aaggacagga aggtttgttc cctccacatc   12960
gtctcgggcc agggagtccc aatccagaga gtatctgctg cacgtcgggc cagctcacgg   13020
gggaggctgc caaggctcag actgcccagt ggcgccccgc caggagaatc attctggtct   13080
cactctgagt gagccagggt gggcgtaggg ggctgggaac ccaaagtgcc cagctgctgc   13140
catgccaggc ctccctggtg gcaggcgtat aaacacacat gatccctaa caggaactac    13200
ccatggcggc aacacagaaa cagatgtgac agatggggct ggaggtagac aggagcagag   13260
agatgcatgc acacctgtgc atgctctgtg tgtgtgtgca tgtctgtgtg ttgctctgtg   13320
tttgtgtgtg catgtctgcg tgttgctgtg tgtgtgtgca tgtccacgtg ttgctgtgtg   13380
tgtgtgcatg tccacgtgtt gctctgtgtg tgtgtgcatg tccacgtgtt gctctgtgtg   13440
tgtgcatgtc cgcgtgttgc ttgtgtttgt gtgtgcgtgt ccgcgtgtcg ctcgtctgtg   13500
tgtgaacatc tgtgccttgtc ctgtatctgt gtttatctgt agacaggagc agagagacgc  13560
agcccagctg gcacctccag gaaaccttta aggacggaat tctatgccaa gcccggggct   13620
gggaggcgga cacccgggtc aggcccaggc gccccaggga ccctcactgc ccggtatgcc   13680
ctgggcccgg gctcacctgg tgtccaaggg caggtcttc tttcgtgga agtggccaat    13740
ctccctgcgc agcaaggcca tccagctctg caggtcagcg gggctgtggt gggcacggtg   13800
ccaccagggt gggcccacc gcacccctcc accttcactg ccctgcctgc tctgctgtga   13860
ctcccaaggt cagaggaggc gacccggctg gatacaacat ggctgtgtgg ctcccctcag   13920
cccacagggg cacctcccag gacagcatgt tccttgtgtg ggcgctggca ccaggctctg   13980
ggcatgggga tggagctggg gcagcaccca cccagctgcc tgtgtcccag ccacaccttc   14040
tctttgcccg gggctgagag gccagcgccc caggaccagc gagcccccaa ggcaggtcca   14100
gcctggtgcc tgcaggccca caccccagt caccttgcac tcgtcctcgg accccagtc    14160
accttgcgct cctcctcgga ggaggccgag aagaaccacg tgcggtgctt cttgctgatg   14220
tggatgatct tgaaggggaa aacgttgttg gacgtggtct cctcagccgc ccgcatcacc   14280
ctgggggcac agcgccaggg gtcacggcct ggttcacagc tatagggatg gccttcccac   14340
agcaccccc tgtgaacacg tctcggcacc agcaccacgc cccaacggaa gagggcagat   14400
ctgggtgggc cctggctgct gatgctccca gtagtgagct tcatgcccag gcaggcgtaa   14460
gggggcatgg aggggcatgg aagagggtg ctgggtgggc ttcgtgggag cagcagtgca    14520
caggagacaa ggacaaacct gcctcgatgc ccgccaatgc cactttacat ggacgccacc   14580
ctcccacctc tggccccatt tgccccaggc ctgcttggcc tccctggggt accccacagg   14640
gctccgtgcc cctgaggccc agcagcagcc ctgagtgcat ttcagggaat gactcgtgcc   14700
tgctctgcgg cccactcaca cagccaggat gtggggtttg cgctgagttt atcacgtggg   14760
gagccctgcc agcaggcac cggggcaggt gcacttatac ggcccataag agcctggcca   14820
aaactcctca ggcccagcat tccctgatgg gctagacaat tccctggggc atgattgcat   14880
ctgccactgg gcccagggtt catggcatgg ctggcacatg ctggaggccg gaaggcgctg   14940
tgtctgtctg cagaaaggga acgaccttcc ccaggggacc ccggagctct gtgccagcat   15000
```

```
gggggcctgg caccaggctg ggtgctctgg caaggctgcc ctaccaggcc tgtggccagg    15060
gtgcaggccg gggcctagag tcactccaaa ggtcccagtt ccactactga taccatgtga    15120
cccttggttc ctcataggca ggaggggctg ggcccttaag gggtggtaag aggcatagat    15180
aaatgctgtg gggtgcaggg ctccgatggg atagcaacca gaaccagagc tgggtgccag    15240
cattaaccct ttgtgtgggc cccaggccat gggctgtgcc agtgcactcc cccacccaca    15300
tgccacctgg ccaccgccca cctgcctgtt agtgcagaag ccctccagg gcagctcatg     15360
gcccatcact ggatagagcc cagcccagga catgcgtgaa gctggaaact gatcccggcc    15420
tgggaggacc ctggagcagg gaatcctagg gcccagcctc tgtttgggac agggcctggg    15480
ctggctgggg tctgggctgc ctggaaagag gtcatggtgg gtgaagggc aaggtgggga     15540
gggaggagag atgcagaagt cactgggtgg tggccgagtg gagactctgg agagcaggct    15600
gtccaggcct ctgggacttg tgcacaaagc cacaggaaga ccctggcacc cccaaggtcc    15660
tgcgcctgag ggcaggacac gcggagaggg cgaggcactg tggaggctgg gcggggagga    15720
caggggatgg gcacgaaggc tgcttcggga aagcactttc cttgggcggg aataaggggc    15780
aggcccagct ggggctctgc tgggagggac ccgctggctg tgggggcccg aggtcagcag    15840
gcaggtcggg cacttaccgg ttatagccac tcagggagaa ggcgccctgc ggggaggcag    15900
aggtgctact cttgaagtag tagacgcagc gtttgtggat gatgacaaag cgcaggggcc    15960
ctgtgggagg tggcaagggc aggaaggtga gcctggaggg gcagctgcca agacccactg    16020
tgaggaccct ccacaggaca acttggggcc aggcctcctg cctctaagcc ttaccaaatg    16080
gaagagcagg gagcaaggct ggcatgctgc cccctcccca ggagcccact ctggggccaa    16140
atacggaaaa aattgtaggc acactggcta gccccagagt gccacccgag ggcaggcctg    16200
gctgccccaca aagaagaggt agatttgggg ggctgtgtgg agccagcatg aggcaaggca    16260
gagccaggac cagaggccca gggaggccac agctgacttg ctgggtgctg cagggctgtt    16320
ggaggctccc actaccccag agctaaaaga gggggactaa ggccgggtgc agtggctcac    16380
gcctgcgatc ccagctactc aggaggctga agcaggagaa ttgcttgaac ccgggagtca    16440
gaggttgcag tgagccaaga tcgtgctact gcactccagc ctgggtgaca agagtgagac    16500
tgtctctaaa aataaaagat ggggtgagcc tgagcaacat gtgaaacccc atctctacaa    16560
aaaatacaaa acttagccgg acacggtggc atacatctgt agttccagct acttgggagg    16620
ctgaggtggg aggatcattt gagcccagga ggtcgaggct gcagtgagct gtgttcgcac    16680
ccactgcact gcagtctggg tgacagagtg agacataaaa ataataaata ggccaggcgc    16740
ggtggctcat gcctgtaatc ccagaacttt aggaggccaa gacaggatca cttgaagtca    16800
ggagttcgag accaggctga ccaacatggt gaaacgctgt ctctactaaa aatacaaaaa    16860
ttagctgggc gtggtggcac actcctgtaa tcccagctac tcaggaggct gaggcaggag    16920
aattgctgga acccaggagg tggacgttac agtgagctga gatcaagtca ctgcactcca    16980
gcctgggcaa cagagcaaga ctccatctca aaaaataaaa taaataaaaa acaaaaataa    17040
ataaaaaata ggctggatgc ggtggctcac acctgtaatc ccagcacttt gggagaccaa    17100
ggcggatgga tcgcttgagc tcaggagctc caggccagcc tggcaacat aatgaaattc      17160
catctctaca agaaatttaa aaaaaatta cagggcata gtggcatgcc tgtagtccca       17220
gctgagggga tcacctgagc ctgggaggtt gaggctgcag tgagccatga tcacgccact    17280
acactccagc ttgggcaaca gagcaagacc ctgtctcgaa aaataaaat aaaagaggga     17340
```

```
gactcaggag cccggagagt tgccagtga gagccactgg tgtggggcca ccctaggtg    17400 gaaagttaca ctgaaaccac cctagctcca ctgcccagc cctgtcccag gctgggggac    17460
aagccagtta cagctcctcc aaggaggctg tctgtgcaaa gaggagaaca gctcaaccag    17520
tgcccgtaca ggaaccaatc agtccagcct ggacatctca accaggcggc ccaggaccag    17580
ggagtccctg gcagagggca ctgctactgc aaaggcatgg agcacctgct gctcaggccc    17640
tgatgctctt ggccttcagt atctcagcat ttgggtatct ctcaagcctg agggctgctt    17700
cttcctccca gccagctgtc ctgggggcca gagcctgggt cttgtgcagc tccagaggtc    17760
cagcacccag ccaggacttg acacataggt tcactgtggg cgaagtgacc aactaactca    17820
ctgaacattc acggattcag tgagggcagc accagaggcc agacctacct ggccacctgt    17880 ggtcccagg tcctggctgc aggctgcagc tccccttgcc agctggccag cactgtgcac    17940
caccccggac cctgctacag tcctgggggc tagggaagtc aacctctgct tctccagggg    18000
tgccagccac cagagaggga atgggaaaat ccagagggca caccatgtga ggaagcagag    18060
gcttggagag gatgcttact tacatggcta gccctgcccc catgccctcc tactgtgcac    18120
cctaccaccc cagggactca catttcagca gctgaagctg gtaccgcccc ttcttgtgca    18180
ggtagccagc cttggccacg cccccaggca tggttagcag gttctgggca ccaatggcct    18240
tcatagggac aggccaatgc atctcttcag ccgccatgaa gctgcaataa aggacaaagg    18300
cacgtggctc agctacggtc aggcaggaga tgtctgagcc agggcgctca gggggacact    18360
gccaagatcc aggacacagc ttggagggta gggccatgac aggcaaggaa accccttttc    18420
tgagggcctt gggcttccag gtgggacccc agggagagac agagccacgg gctccactca    18480
gtcagcccct ggtccactca gccacaaacc caacccagg atcctgagcg ctacgtgcag    18540
ccctttctct ccactggttc attctgcaca cagccactga gcgcaaggcc cacgggggc    18600 tgggtagaga tgaacgaact cagaaaactg ccagcccagg taagtgagac ctcaggccat    18660
aactacttca agtcccagtg ccaggtgaac ctataagggg cctagacagg aagaaggcaa    18720
gtgagcagcc aagagcaccc agctcaaacg acctgggctc ccatcctggt gtgactttct    18780
gggagatccc aagcctcaga tgctggagga cagagtggac acccagccca gcacacagca    18840
cactgttgtc agcagtggtc gtgaccacca tttggtgggt tggctgctat ccaccccacc    18900
agcccaggat atcactcccc ttccctctga gcccaagcga ggaccacaca gtcagtggag    18960
gaccagtgac tgccttgggg ctaacccagg cccacaggac ccaacatcat gccctgcccc    19020
ctactccagc cccccttact catgctccag ctgctctcct tgagatacac catgctgttt    19080
aatgcttcct cctctgcctg aaatgacctc caccccttcc catgcagaga acttctactc    19140
atccatcaag acccaggtta agagcccctc ttctgctagg caccctcatt gcccacttaa    19200
atccagcatc ttcctcatct cttgtcccag tgaacagtac ccccgaccc tgcactgttt    19260 ggtctgtgcc tgccctcact ccatcctggg tagggtccct cctgtggccc cagtggagtt    19320
ggatgggagc aggcctgtgg ccagtgtcct gttaagccct tagtggagca gctaaggtca    19380
gacccagatg cccagtgggg ctgggactgg ttccactaca gctccaaccc caaaaaacat    19440
acataaagaa aactaagcca gggcaacata gcaagaccct atctctaaaa aaaatttt    19500 ttttaattag tcaggcatgg tgggtgcat ctgtagtccc agctgctcta ggaggctgag    19560
gcaggaggat cacttgagcc caggagtttg aggctgcagt ggtctatgat cgtaccactg    19620
cactccagcc tgggcaacaa agtgagacac tgtctctata aataaataaa atagccggac    19680
gcagtggctc acgcctgtaa tcccagcact ttgggaggcc aaggcaggcg gatcacttga    19740
```

```
gctcaggcgt tcaaggcctg cctgggcaac atatagagac aaccatctct aaaaaataat   19800
tagctgagct tggtggtgca cacctatagt acccggagga ggcttatcca ggaggatcga   19860
ttgagccagg agttccagga ggcagtaagc tatgattggc cactgctctc cagtctgggc   19920
aactgagctg gagctaaaat taaaaaatta aaaacaaaat aaataaaaag aaaaatactc   19980
tctgctttta gcaaaccagc accctccaac aaaagtgcaa gaggaagtct tcaaggcatc   20040
aggctgtctt ctgccggcct cggcctgggt cacccggctg gaccccacca gctccttctg   20100
cacccaaaga cagcccctct gggcaggag gggtcagggg cgggtcccag ccgcaggacc   20160
cccaaccaca ggccaaggtt tggaacaaag gcgccgccac accccgccgc ccgcccaacc   20220
gcgcccggcc cgaaggagcc ccgcagtggg gatggaggag ggagccccgt gcccagtccg   20280
cccgcgggga gctgcccgca gatcgacaag ccccgtgccg gcctgagtcc cccatccgcc   20340
cgccgggacg gtccacgccc gcctttgttc ccccaagaag cgcgtgggcg accagcagcg   20400
cccggggctc gcggcctggt ccaggggctc ggggtgcggg gtccagagcc ggaagctcgc   20460
ggcccgggtc ccggggctcg ggggccgggg ctcggtactc acggcgtcca cgcggcgggc   20520
atggccggct tccccggggc gatccacgcc cgcctcccct gcgagcaccg gcacggcccc   20580
gggccgcgtc cccggccgc cgccgcctcg tcccgggcgc ccgcctcccg ccggcccag    20640
ctccgcggcg cggcccggag cccgccatgc ccgccgcc tggcctggca gccgccggct   20700
cctcccctct cggcggggga ctgggcgggc aggtgaggat cccggcgcgc ccctcccggc   20760
cccgccccct gccgcgtcac cgtgcgcggg aggcacgtga gccccctgcg ggcctcagtt   20820
tccccacgct gcaaggaggt tggtgggcgc ttgggacagg aggcccacat ctgttggtgc   20880
agcctggaat caagaagcct tcgatgcaaa cgaggcctcc cgctccactc ccccaacacc   20940
tgccagtcca cacagcttgg ttggaaatcc acggccggcg cgggagcctc ggctctgagg   21000
ccccgcccag gtcccatccc gccgggccct tgcaaccagc tccctcggga aagtggcctc   21060
tgcaaaacgg cacctgcatg gagggcggca acggggcaag ggatcgggca cgtgccccgc   21120
cctcaccttc tccactttcc tgcgggactc catgggcctc cagccccgga ttctccaagg   21180
agccaggggt ctggtccttg gcacctccca cctgcttgcc caaacgcagg cacctcaccc   21240
aggagagtcc cctggggtgg ccaaaggccg gcagaggccc ttgctggcct cccaggcatc   21300
ctgcctcctc catcttccac ctgcaaacaa gctgccacca agatgggcca gatgcaggtg   21360
tggctctaac agcctgggcc tgaccctacc tagctgtcca tcctgggcac ccaccctggt   21420
ttcaaggccc cacctcaggc ccgctatctg gacttcttcc cactgcaccc agccttcgag   21480
gctctgtccc atctctgtgc ctctgttctc agtgccttg tctggcctgc ctcaaggatc   21540
ccacctcctt ccagctgccc tgccaggccc ctctccattg cctcttggca accccctcca   21600
cttcctctcc tcaggcttcc tctgcctcca gccccctcca cccagcacag aatcaacacg   21660
cacaccattc ccatcactgc tcagtgctaa acctctaggg cctcctcatg ccaacctggc   21720
ccttcctgat tcagccactc ctgccctcta ccttctgtgc tcttacgcca gccagaccct   21780
atggctccag ttacctgaat cgagcaagca cccacttgca ggcctcagcc cctgctgttg   21840
ccacagccta aagttgaaac tgaactaacc cagccatcaa gagttggctc aaaagaacat   21900
ggatccttca caaacttcca gaaaatagaa gaggagggaa ctcattctat gagagcagca   21960
ttatcccaat accaaaacca gacaaagaca tcacaataaa actacaaacc aatatccctt   22020
atgggtatag acataaacat cctcaacaaa atactggcca actgaatcct gcaacatata   22080
```

```
aaagggattc tacaccaaga ccatgtggga tttatcccag gaatacaagg atggcttaat    22140
attcaaaaca attaatgtaa tacaccatat caatagaata aaggacaacc acatgatttt    22200
gatagacgaa gaacaagtgt ttgacaaaat tcaacactcc tccatgataa gaacagtcaa    22260
caaaccagga atagaaggga agttcctcaa tctgataaag ggttctatga aaacccaca     22320 gctaacatac ctagtggtaa aagactgaaa gttttccccc caagaacagg aacaaggaaa    22380
ggatgtctgc tctacttcta ttcagcatag tactggagat tctcaccaga gtaattaggc    22440
aataaaaaga aataaaaggt atccagaatg gaaagaaaga acaattattc actgattaga    22500
ttattttaca tacagaaaat cccaaggaat ccacttaaaa attattagaa tagccatgcg    22560
cagtggctca cgcctgtaat cccagcactt tgggaggctg aggcgggcag atcacctgag    22620
gtcaggagtt cgagaccagc gtggccaaca tggtgaaacc cccatttcta ctaaaaatac    22680
caggtggcag gcacctgtaa tcccagctat ttgggaggct gaggcaggag aatcgcttga    22740
acccgggagg tggaggtagc agtgagccga gattgcgcca ttgcactcca gcctgggaa     22800 caagaatgag acttcatctc aaaaaaaaaa aattattaga ataaatgagc agcaaggtgg    22860
caggatataa gatcaacata caaaaatcaa ttctatttct atatactagc aacaatccaa    22920
aaatgaaagg aagagttagt tcaagcgttc ccttttccag gcagtctccc                22970

<210> SEQ ID NO 27
<211> LENGTH: 109
<212> TYPE: DNA
<213> ORGANISM: homo sapiens
<220> FEATURE:
<221> NAME/KEY: misc_feature
<222> LOCATION: (2)..(4)
<223> OTHER INFORMATION: n = C, T, G or A
      provided that the mutant domain is not wild type
<220> FEATURE:
<221> NAME/KEY: misc_feature
<222> LOCATION: (11)..(13)
<223> OTHER INFORMATION: n = C, T, G or A
      provided that the mutant domain is not wild type
<220> FEATURE:
<221> NAME/KEY: misc_feature
<222> LOCATION: (17)..(19)
<223> OTHER INFORMATION: n = C, T, G or A
      provided that the mutant domain is not wild type

<400> SEQUENCE: 27
gnnntcaccc nnngatnnnc agagtttcag gagcttctcc tttgaaaagc cccggcaacc     60
ctcacaggct gacactggcg gggacgactc ggacgaggac tatgagaag                109

<210> SEQ ID NO 28
<211> LENGTH: 109
<212> TYPE: DNA
<213> ORGANISM: homo sapiens
<220> FEATURE:
<221> NAME/KEY: misc_feature
<222> LOCATION: (2)..(4)
<223> OTHER INFORMATION: n = C, T, G or A
      provided that the mutant domain is not wild type

<400> SEQUENCE: 28
gnnntcaccc cccgatgggc agagtttcag gagcttctcc tttgaaaagc cccggcaacc     60
ctcacaggct gacactggcg gggacgactc ggacgaggac tatgagaag                109

<210> SEQ ID NO 29
<211> LENGTH: 109
<212> TYPE: DNA
<213> ORGANISM: homo sapiens
```

```
<220> FEATURE:
<221> NAME/KEY: misc_feature
<222> LOCATION: (5)..(7)
<223> OTHER INFORMATION: n = C, T, G or A
      provided that the mutant domain is not wild type

<400> SEQUENCE: 29
gcgannnccc cccgatgggc agagtttcag gagcttctcc tttgaaaagc cccggcaacc      60
ctcacaggct gacactggcg gggacgactc ggacgaggac tatgagaag               109

<210> SEQ ID NO 30
<211> LENGTH: 109
<212> TYPE: DNA
<213> ORGANISM: homo sapiens
<220> FEATURE:
<221> NAME/KEY: misc_feature
<222> LOCATION: (8)..(10)
<223> OTHER INFORMATION: n = C, T, G or A
      provided that the mutant domain is not wild type

<400> SEQUENCE: 30
gcgatcannn cccgatgggc agagtttcag gagcttctcc tttgaaaagc cccggcaacc      60
ctcacaggct gacactggcg gggacgactc ggacgaggac tatgagaag               109

<210> SEQ ID NO 31
<211> LENGTH: 109
<212> TYPE: DNA
<213> ORGANISM: homo sapiens
<220> FEATURE:
<221> NAME/KEY: misc_feature
<222> LOCATION: (11)..(13)
<223> OTHER INFORMATION: n = C, T, G or A
      provided that the mutant domain is not wild type

<400> SEQUENCE: 31
gcgatcaccc nnngatgggc agagtttcag gagcttctcc tttgaaaagc cccggcaacc      60
ctcacaggct gacactggcg gggacgactc ggacgaggac tatgagaag               109

<210> SEQ ID NO 32
<211> LENGTH: 109
<212> TYPE: DNA
<213> ORGANISM: homo sapiens
<220> FEATURE:
<221> NAME/KEY: misc_feature
<222> LOCATION: (14)..(16)
<223> OTHER INFORMATION: n = C, T, G or A
      provided that the mutant domain is not wild type

<400> SEQUENCE: 32
gcgatcaccc cccnnngggc agagtttcag gagcttctcc tttgaaaagc cccggcaacc      60
ctcacaggct gacactggcg gggacgactc ggacgaggac tatgagaag               109

<210> SEQ ID NO 33
<211> LENGTH: 109
<212> TYPE: DNA
<213> ORGANISM: homo sapiens
<220> FEATURE:
<221> NAME/KEY: misc_feature
<222> LOCATION: (17)..(19)
<223> OTHER INFORMATION: n = C, T, G or A
      provided that the mutant domain is not wild type

<400> SEQUENCE: 33
gcgatcaccc cccgatnnnc agagtttcag gagcttctcc tttgaaaagc cccggcaacc      60
ctcacaggct gacactggcg gggacgactc ggacgaggac tatgagaag               109
```

<210> SEQ ID NO 34
<211> LENGTH: 109
<212> TYPE: DNA
<213> ORGANISM: homo sapiens
<220> FEATURE:
<221> NAME/KEY: misc_feature
<222> LOCATION: (20)..(22)
<223> OTHER INFORMATION: n = C, T, G or A
      provided that the mutant domain is not wild type

<400> SEQUENCE: 34
gcgatcaccc cccgatgggn nnagtttcag gagcttctcc tttgaaaagc cccggcaacc    60
ctcacaggct gacactggcg gggacgactc ggacgaggac tatgagaag             109

<210> SEQ ID NO 35
<211> LENGTH: 109
<212> TYPE: DNA
<213> ORGANISM: homo sapiens
<220> FEATURE:
<221> NAME/KEY: misc_feature
<222> LOCATION: (23)..(25)
<223> OTHER INFORMATION: n = C, T, G or A
      provided that the mutant domain is not wild type

<400> SEQUENCE: 35
gcgatcaccc cccgatgggc agnnnttcag gagcttctcc tttgaaaagc cccggcaacc    60
ctcacaggct gacactggcg gggacgactc ggacgaggac tatgagaag             109

<210> SEQ ID NO 36
<211> LENGTH: 109
<212> TYPE: DNA
<213> ORGANISM: homo sapiens
<220> FEATURE:
<221> NAME/KEY: misc_feature
<222> LOCATION: (26)..(28)
<223> OTHER INFORMATION: n = C, T, G or A
      provided that the mutant domain is not wild type

<400> SEQUENCE: 36
gcgatcaccc cccgatgggc agagtnnnag gagcttctcc tttgaaaagc cccggcaacc    60
ctcacaggct gacactggcg gggacgactc ggacgaggac tatgagaag             109

<210> SEQ ID NO 37
<211> LENGTH: 109
<212> TYPE: DNA
<213> ORGANISM: homo sapiens
<220> FEATURE:
<221> NAME/KEY: misc_feature
<222> LOCATION: (29)..(31)
<223> OTHER INFORMATION: n = C, T, G or A
      provided that the mutant domain is not wild type

<400> SEQUENCE: 37
gcgatcaccc cccgatgggc agagtttcnn nagcttctcc tttgaaaagc cccggcaacc    60
ctcacaggct gacactggcg gggacgactc ggacgaggac tatgagaag             109

<210> SEQ ID NO 38
<211> LENGTH: 109
<212> TYPE: DNA
<213> ORGANISM: homo sapiens
<220> FEATURE:
<221> NAME/KEY: misc_feature
<222> LOCATION: (32)..(34)
<223> OTHER INFORMATION: n = C, T, G or A
      provided that the mutant domain is not wild type

<400> SEQUENCE: 38
gcgatcaccc cccgatgggc agagtttcag gnnnttctcc tttgaaaagc cccggcaacc    60
ctcacaggct gacactggcg gggacgactc ggacgaggac tatgagaag               109

<210> SEQ ID NO 39
<211> LENGTH: 109
<212> TYPE: DNA
<213> ORGANISM: homo sapiens
<220> FEATURE:
<221> NAME/KEY: misc_feature
<222> LOCATION: (35)..(37)
<223> OTHER INFORMATION: n = C, T, G or A
      provided that the mutant domain is not wild type

<400> SEQUENCE: 39
gcgatcaccc cccgatgggc agagtttcag gagcnnntcc tttgaaaagc cccggcaacc    60
ctcacaggct gacactggcg gggacgactc ggacgaggac tatgagaag               109

<210> SEQ ID NO 40
<211> LENGTH: 109
<212> TYPE: DNA
<213> ORGANISM: homo sapiens
<220> FEATURE:
<221> NAME/KEY: misc_feature
<222> LOCATION: (38)..(40)
<223> OTHER INFORMATION: n = C, T, G or A
      provided that the mutant domain is not wild type

<400> SEQUENCE: 40
gcgatcaccc cccgatgggc agagtttcag gagcttcnnn tttgaaaagc cccggcaacc    60
ctcacaggct gacactggcg gggacgactc ggacgaggac tatgagaag               109

<210> SEQ ID NO 41
<211> LENGTH: 109
<212> TYPE: DNA
<213> ORGANISM: homo sapiens
<220> FEATURE:
<221> NAME/KEY: misc_feature
<222> LOCATION: (41)..(43)
<223> OTHER INFORMATION: n = C, T, G or A
      provided that the mutant domain is not wild type

<400> SEQUENCE: 41
gcgatcaccc cccgatgggc agagtttcag gagcttctcc nnngaaaagc cccggcaacc    60
ctcacaggct gacactggcg gggacgactc ggacgaggac tatgagaag               109

<210> SEQ ID NO 42
<211> LENGTH: 109
<212> TYPE: DNA
<213> ORGANISM: homo sapiens
<220> FEATURE:
<221> NAME/KEY: misc_feature
<222> LOCATION: (44)..(46)
<223> OTHER INFORMATION: n = C, T, G or A
      provided that the mutant domain is not wild type

<400> SEQUENCE: 42
gcgatcaccc cccgatgggc agagtttcag gagcttctcc tttnnnaagc cccggcaacc    60
ctcacaggct gacactggcg gggacgactc ggacgaggac tatgagaag               109

<210> SEQ ID NO 43
<211> LENGTH: 109
<212> TYPE: DNA

```
<213> ORGANISM: homo sapiens
<220> FEATURE:
<221> NAME/KEY: misc_feature
<222> LOCATION: (47)..(49)
<223> OTHER INFORMATION: n = C, T, G or A
      provided that the mutant domain is not wild type

<400> SEQUENCE: 43
gcgatcaccc cccgatgggc agagtttcag gagcttctcc tttgaannnc cccggcaacc    60
ctcacaggct gacactggcg gggacgactc ggacgaggac tatgagaag              109

<210> SEQ ID NO 44
<211> LENGTH: 109
<212> TYPE: DNA
<213> ORGANISM: homo sapiens
<220> FEATURE:
<221> NAME/KEY: misc_feature
<222> LOCATION: (50)..(52)
<223> OTHER INFORMATION: n = C, T, G or A
      provided that the mutant domain is not wild type

<400> SEQUENCE: 44
gcgatcaccc cccgatgggc agagtttcag gagcttctcc tttgaaaagn nncggcaacc    60
ctcacaggct gacactggcg gggacgactc ggacgaggac tatgagaag              109

<210> SEQ ID NO 45
<211> LENGTH: 109
<212> TYPE: DNA
<213> ORGANISM: homo sapiens
<220> FEATURE:
<221> NAME/KEY: misc_feature
<222> LOCATION: (53)..(55)
<223> OTHER INFORMATION: n = C, T, G or A
      provided that the mutant domain is not wild type

<400> SEQUENCE: 45
gcgatcaccc cccgatgggc agagtttcag gagcttctcc tttgaaaagc ccnnncaacc    60
ctcacaggct gacactggcg gggacgactc ggacgaggac tatgagaag              109

<210> SEQ ID NO 46
<211> LENGTH: 109
<212> TYPE: DNA
<213> ORGANISM: homo sapiens
<220> FEATURE:
<221> NAME/KEY: misc_feature
<222> LOCATION: (56)..(58)
<223> OTHER INFORMATION: n = C, T, G or A
      provided that the mutant domain is not wild type

<400> SEQUENCE: 46
gcgatcaccc cccgatgggc agagtttcag gagcttctcc tttgaaaagc cccggnnncc    60
ctcacaggct gacactggcg gggacgactc ggacgaggac tatgagaag              109

<210> SEQ ID NO 47
<211> LENGTH: 109
<212> TYPE: DNA
<213> ORGANISM: homo sapiens
<220> FEATURE:
<221> NAME/KEY: misc_feature
<222> LOCATION: (59)..(61)
<223> OTHER INFORMATION: n = C, T, G or A
      provided that the mutant domain is not wild type

<400> SEQUENCE: 47
gcgatcaccc cccgatgggc agagtttcag gagcttctcc tttgaaaagc cccggcaann    60
```
ntcacaggct gacactggcg gggacgactc ggacgaggac tatgagaag        109

<210> SEQ ID NO 48
<211> LENGTH: 109
<212> TYPE: DNA
<213> ORGANISM: homo sapiens
<220> FEATURE:
<221> NAME/KEY: misc_feature
<222> LOCATION: (62)..(64)
<223> OTHER INFORMATION: n = C, T, G or A
      provided that the mutant domain is not wild type

<400> SEQUENCE: 48
gcgatcaccc cccgatgggc agagtttcag gagcttctcc tttgaaaagc cccggcaacc        60
cnnncaggct gacactggcg gggacgactc ggacgaggac tatgagaag        109

<210> SEQ ID NO 49
<211> LENGTH: 109
<212> TYPE: DNA
<213> ORGANISM: homo sapiens
<220> FEATURE:
<221> NAME/KEY: misc_feature
<222> LOCATION: (65)..(67)
<223> OTHER INFORMATION: n = C, T, G or A
      provided that the mutant domain is not wild type

<400> SEQUENCE: 49
gcgatcaccc cccgatgggc agagtttcag gagcttctcc tttgaaaagc cccggcaacc        60
ctcannngct gacactggcg gggacgactc ggacgaggac tatgagaag        109

<210> SEQ ID NO 50
<211> LENGTH: 109
<212> TYPE: DNA
<213> ORGANISM: homo sapiens
<220> FEATURE:
<221> NAME/KEY: misc_feature
<222> LOCATION: (68)..(70)
<223> OTHER INFORMATION: n = C, T, G or A
      provided that the mutant domain is not wild type

<400> SEQUENCE: 50
gcgatcaccc cccgatgggc agagtttcag gagcttctcc tttgaaaagc cccggcaacc        60
ctcacagnnn gacactggcg gggacgactc ggacgaggac tatgagaag        109

<210> SEQ ID NO 51
<211> LENGTH: 109
<212> TYPE: DNA
<213> ORGANISM: homo sapiens
<220> FEATURE:
<221> NAME/KEY: misc_feature
<222> LOCATION: (71)..(73)
<223> OTHER INFORMATION: n = C, T, G or A
      provided that the mutant domain is not wild type

<400> SEQUENCE: 51
gcgatcaccc cccgatgggc agagtttcag gagcttctcc tttgaaaagc cccggcaacc        60
ctcacaggct nnnactggcg gggacgactc ggacgaggac tatgagaag        109

<210> SEQ ID NO 52
<211> LENGTH: 109
<212> TYPE: DNA
<213> ORGANISM: homo sapiens
<220> FEATURE:
<221> NAME/KEY: misc_feature
<222> LOCATION: (74)..(76)
<223> OTHER INFORMATION: n = C, T, G or A provided that the mutant domain is not wild type

<400> SEQUENCE: 52
gcgatcaccc cccgatgggc agagtttcag gagcttctcc tttgaaaagc cccggcaacc    60
ctcacaggct gacnnnggcg gggacgactc ggacgaggac tatgagaag               109

<210> SEQ ID NO 53
<211> LENGTH: 109
<212> TYPE: DNA
<213> ORGANISM: homo sapiens
<220> FEATURE:
<221> NAME/KEY: misc_feature
<222> LOCATION: (77)..(79)
<223> OTHER INFORMATION: n = C, T, G or A
      provided that the mutant domain is not wild type

<400> SEQUENCE: 53
gcgatcaccc cccgatgggc agagtttcag gagcttctcc tttgaaaagc cccggcaacc    60
ctcacaggct gacactnnng gggacgactc ggacgaggac tatgagaag               109

<210> SEQ ID NO 54
<211> LENGTH: 109
<212> TYPE: DNA
<213> ORGANISM: homo sapiens
<220> FEATURE:
<221> NAME/KEY: misc_feature
<222> LOCATION: (80)..(82)
<223> OTHER INFORMATION: n = C, T, G or A
      provided that the mutant domain is not wild type

<400> SEQUENCE: 54
gcgatcaccc cccgatgggc agagtttcag gagcttctcc tttgaaaagc cccggcaacc    60
ctcacaggct gacactggcn nngacgactc ggacgaggac tatgagaag               109

<210> SEQ ID NO 55
<211> LENGTH: 109
<212> TYPE: DNA
<213> ORGANISM: homo sapiens
<220> FEATURE:
<221> NAME/KEY: misc_feature
<222> LOCATION: (83)..(85)
<223> OTHER INFORMATION: n = C, T, G or A
      provided that the mutant domain is not wild type

<400> SEQUENCE: 55
gcgatcaccc cccgatgggc agagtttcag gagcttctcc tttgaaaagc cccggcaacc    60
ctcacaggct gacactggcg ggnnngactc ggacgaggac tatgagaag               109

<210> SEQ ID NO 56
<211> LENGTH: 109
<212> TYPE: DNA
<213> ORGANISM: homo sapiens
<220> FEATURE:
<221> NAME/KEY: misc_feature
<222> LOCATION: (86)..(88)
<223> OTHER INFORMATION: n = C, T, G or A
      provided that the mutant domain is not wild type

<400> SEQUENCE: 56
gcgatcaccc cccgatgggc agagtttcag gagcttctcc tttgaaaagc cccggcaacc    60
ctcacaggct gacactggcg gggacnnntc ggacgaggac tatgagaag               109

<210> SEQ ID NO 57
<211> LENGTH: 109

```
<212> TYPE: DNA
<213> ORGANISM: homo sapiens
<220> FEATURE:
<221> NAME/KEY: misc_feature
<222> LOCATION: (89)..(91)
<223> OTHER INFORMATION: n = C, T, G or A
      provided that the mutant domain is not wild type

<400> SEQUENCE: 57
gcgatcaccc cccgatgggc agagtttcag gagcttctcc tttgaaaagc cccggcaacc      60
ctcacaggct gacactggcg gggacgacnn ngacgaggac tatgagaag                 109

<210> SEQ ID NO 58
<211> LENGTH: 109
<212> TYPE: DNA
<213> ORGANISM: homo sapiens
<220> FEATURE:
<221> NAME/KEY: misc_feature
<222> LOCATION: (92)..(94)
<223> OTHER INFORMATION: n = C, T, G or A
      provided that the mutant domain is not wild type

<400> SEQUENCE: 58
gcgatcaccc cccgatgggc agagtttcag gagcttctcc tttgaaaagc cccggcaacc      60
ctcacaggct gacactggcg gggacgactc gnnngaggac tatgagaag                 109

<210> SEQ ID NO 59
<211> LENGTH: 109
<212> TYPE: DNA
<213> ORGANISM: homo sapiens
<220> FEATURE:
<221> NAME/KEY: misc_feature
<222> LOCATION: (95)..(97)
<223> OTHER INFORMATION: n = C, T, G or A
      provided that the mutant domain is not wild type

<400> SEQUENCE: 59
gcgatcaccc cccgatgggc agagtttcag gagcttctcc tttgaaaagc cccggcaacc      60
ctcacaggct gacactggcg gggacgactc ggacnnngac tatgagaag                 109

<210> SEQ ID NO 60
<211> LENGTH: 109
<212> TYPE: DNA
<213> ORGANISM: homo sapiens
<220> FEATURE:
<221> NAME/KEY: misc_feature
<222> LOCATION: (98)..(100)
<223> OTHER INFORMATION: n = C, T, G or A
      provided that the mutant domain is not wild type

<400> SEQUENCE: 60
gcgatcaccc cccgatgggc agagtttcag gagcttctcc tttgaaaagc cccggcaacc      60
ctcacaggct gacactggcg gggacgactc ggacgagnnn tatgagaag                 109

<210> SEQ ID NO 61
<211> LENGTH: 109
<212> TYPE: DNA
<213> ORGANISM: homo sapiens
<220> FEATURE:
<221> NAME/KEY: misc_feature
<222> LOCATION: (101)..(103)
<223> OTHER INFORMATION: n = C, T, G or A
      provided that the mutant domain is not wild type

<400> SEQUENCE: 61
gcgatcaccc cccgatgggc agagtttcag gagcttctcc tttgaaaagc cccggcaacc      60
```

```
ctcacaggct gacactggcg gggacgactc ggacgaggac nnngagaag        109
```

<210> SEQ ID NO 62
<211> LENGTH: 109
<212> TYPE: DNA
<213> ORGANISM: homo sapiens
<220> FEATURE:
<221> NAME/KEY: misc_feature
<222> LOCATION: (104)..(106)
<223> OTHER INFORMATION: n = C, T, G or A
      provided that the mutant domain is not wild type

<400> SEQUENCE: 62

```
gcgatcaccc cccgatgggc agagtttcag gagcttctcc tttgaaaagc cccggcaacc    60
ctcacaggct gacactggcg gggacgactc ggacgaggac tatnnnaag             109
```

<210> SEQ ID NO 63
<211> LENGTH: 109
<212> TYPE: DNA
<213> ORGANISM: homo sapiens
<220> FEATURE:
<221> NAME/KEY: misc_feature
<222> LOCATION: (107)..(109)
<223> OTHER INFORMATION: n = C, T, G or A
      provided that the mutant domain is not wild type

<400> SEQUENCE: 63

```
gcgatcaccc cccgatgggc agagtttcag gagcttctcc tttgaaaagc cccggcaacc    60
ctcacaggct gacactggcg gggacgactc ggacgaggac tatgagnnn             109
```

<210> SEQ ID NO 64
<211> LENGTH: 36
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: Xaa = any amino acid
      provided that the mutant domain is not wild type
<220> FEATURE:
<221> NAME/KEY: MISC_FEATURE
<222> LOCATION: (4)..(4)
<223> OTHER INFORMATION: Xaa = any amino acid
      provided that the mutant domain is not wild type
<220> FEATURE:
<221> NAME/KEY: MISC_FEATURE
<222> LOCATION: (6)..(6)
<223> OTHER INFORMATION: Xaa = any amino acid
      provided that the mutant domain is not wild type

<400> SEQUENCE: 64

```
Xaa Ser Pro Xaa Asp Xaa Gln Ser Phe Arg Ser Phe Ser Phe Glu Lys
1               5                   10                  15

Pro Arg Gln Pro Ser Gln Ala Asp Thr Gly Gly Asp Asp Ser Asp Glu
            20                  25                  30

Asp Tyr Glu Lys
            35
```

<210> SEQ ID NO 65
<211> LENGTH: 36
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: Xaa = any amino acid
      provided that the mutant domain is not wild type

<400> SEQUENCE: 65

Xaa Ser Pro Pro Asp Gly Gln Ser Phe Arg Ser Phe Ser Phe Glu Lys
1               5                   10                  15

Pro Arg Gln Pro Ser Gln Ala Asp Thr Gly Gly Asp Asp Ser Asp Glu
            20                  25                  30

Asp Tyr Glu Lys
        35

<210> SEQ ID NO 66
<211> LENGTH: 36
<212> TYPE: PRT
<213> ORGANISM: homo sapiens
<220> FEATURE:
<221> NAME/KEY: MISC_FEATURE
<222> LOCATION: (2)..(2)
<223> OTHER INFORMATION: Xaa = any amino acid
      provided that the mutant domain is not wild type

<400> SEQUENCE: 66

Arg Xaa Pro Pro Asp Gly Gln Ser Phe Arg Ser Phe Ser Phe Glu Lys
1               5                   10                  15

Pro Arg Gln Pro Ser Gln Ala Asp Thr Gly Gly Asp Asp Ser Asp Glu
            20                  25                  30

Asp Tyr Glu Lys
        35

<210> SEQ ID NO 67
<211> LENGTH: 36
<212> TYPE: PRT
<213> ORGANISM: homo sapiens
<220> FEATURE:
<221> NAME/KEY: MISC_FEATURE
<222> LOCATION: (3)..(3)
<223> OTHER INFORMATION: Xaa = any amino acid
      provided that the mutant domain is not wild type

<400> SEQUENCE: 67

Arg Ser Xaa Pro Asp Gly Gln Ser Phe Arg Ser Phe Ser Phe Glu Lys
1               5                   10                  15

Pro Arg Gln Pro Ser Gln Ala Asp Thr Gly Gly Asp Asp Ser Asp Glu
            20                  25                  30

Asp Tyr Glu Lys
        35

<210> SEQ ID NO 68
<211> LENGTH: 36
<212> TYPE: PRT
<213> ORGANISM: homo sapiens
<220> FEATURE:
<221> NAME/KEY: MISC_FEATURE
<222> LOCATION: (4)..(4)
<223> OTHER INFORMATION: Xaa = any amino acid
      provided that the mutant domain is not wild type

<400> SEQUENCE: 68

Arg Ser Pro Xaa Asp Gly Gln Ser Phe Arg Ser Phe Ser Phe Glu Lys
1               5                   10                  15

Pro Arg Gln Pro Ser Gln Ala Asp Thr Gly Gly Asp Asp Ser Asp Glu
            20                  25                  30

Asp Tyr Glu Lys
        35

```
<210> SEQ ID NO 69
<211> LENGTH: 36
<212> TYPE: PRT
<213> ORGANISM: homo sapiens
<220> FEATURE:
<221> NAME/KEY: MISC_FEATURE
<222> LOCATION: (5)..(5)
<223> OTHER INFORMATION: Xaa = any amino acid
      provided that the mutant domain is not wild type

<400> SEQUENCE: 69

Arg Ser Pro Pro Xaa Gly Gln Ser Phe Arg Ser Phe Ser Phe Glu Lys
1               5                   10                  15

Pro Arg Gln Pro Ser Gln Ala Asp Thr Gly Gly Asp Asp Ser Asp Glu
            20                  25                  30

Asp Tyr Glu Lys
            35

<210> SEQ ID NO 70
<211> LENGTH: 36
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: Xaa = any amino acid
      provided that the mutant domain is not wild type

<400> SEQUENCE: 70

Arg Ser Pro Pro Asp Xaa Gln Ser Phe Arg Ser Phe Ser Phe Glu Lys
1               5                   10                  15

Pro Arg Gln Pro Ser Gln Ala Asp Thr Gly Gly Asp Asp Ser Asp Glu
            20                  25                  30

Asp Tyr Glu Lys
            35

<210> SEQ ID NO 71
<211> LENGTH: 36
<212> TYPE: PRT
<213> ORGANISM: homo sapiens
<220> FEATURE:
<221> NAME/KEY: MISC_FEATURE
<222> LOCATION: (7)..(7)
<223> OTHER INFORMATION: Xaa = any amino acid
      provided that the mutant domain is not wild type

<400> SEQUENCE: 71

Arg Ser Pro Pro Asp Gly Xaa Ser Phe Arg Ser Phe Ser Phe Glu Lys
1               5                   10                  15

Pro Arg Gln Pro Ser Gln Ala Asp Thr Gly Gly Asp Asp Ser Asp Glu
            20                  25                  30

Asp Tyr Glu Lys
            35

<210> SEQ ID NO 72
<211> LENGTH: 36
<212> TYPE: PRT
<213> ORGANISM: homo sapiens
<220> FEATURE:
<221> NAME/KEY: MISC_FEATURE
<222> LOCATION: (8)..(8)
<223> OTHER INFORMATION: Xaa = any amino acid
      provided that the mutant domain is not wild type

<400> SEQUENCE: 72

Arg Ser Pro Pro Asp Gly Gln Xaa Phe Arg Ser Phe Ser Phe Glu Lys
```

-continued

```
                1               5                  10                 15
Pro Arg Gln Pro Ser Gln Ala Asp Thr Gly Gly Asp Asp Ser Asp Glu
            20                  25                 30

Asp Tyr Glu Lys
        35

<210> SEQ ID NO 73
<211> LENGTH: 36
<212> TYPE: PRT
<213> ORGANISM: homo sapiens
<220> FEATURE:
<221> NAME/KEY: MISC_FEATURE
<222> LOCATION: (9)..(9)
<223> OTHER INFORMATION: Xaa = any amino acid
      provided that the mutant domain is not wild type

<400> SEQUENCE: 73

Arg Ser Pro Pro Asp Gly Gln Ser Xaa Arg Ser Phe Ser Phe Glu Lys
1               5                  10                 15

Pro Arg Gln Pro Ser Gln Ala Asp Thr Gly Gly Asp Asp Ser Asp Glu
            20                  25                 30

Asp Tyr Glu Lys
        35

<210> SEQ ID NO 74
<211> LENGTH: 36
<212> TYPE: PRT
<213> ORGANISM: homo sapiens
<220> FEATURE:
<221> NAME/KEY: MISC_FEATURE
<222> LOCATION: (10)..(10)
<223> OTHER INFORMATION: Xaa = any amino acid
      provided that the mutant domain is not wild type

<400> SEQUENCE: 74

Arg Ser Pro Pro Asp Gly Gln Ser Phe Xaa Ser Phe Ser Phe Glu Lys
1               5                  10                 15

Pro Arg Gln Pro Ser Gln Ala Asp Thr Gly Gly Asp Asp Ser Asp Glu
            20                  25                 30

Asp Tyr Glu Lys
        35

<210> SEQ ID NO 75
<211> LENGTH: 36
<212> TYPE: PRT
<213> ORGANISM: homo sapiens
<220> FEATURE:
<221> NAME/KEY: MISC_FEATURE
<222> LOCATION: (11)..(11)
<223> OTHER INFORMATION: Xaa = any amino acid
      provided that the mutant domain is not wild type

<400> SEQUENCE: 75

Arg Ser Pro Pro Asp Gly Gln Ser Phe Arg Xaa Phe Ser Phe Glu Lys
1               5                  10                 15

Pro Arg Gln Pro Ser Gln Ala Asp Thr Gly Gly Asp Asp Ser Asp Glu
            20                  25                 30

Asp Tyr Glu Lys
        35

<210> SEQ ID NO 76
<211> LENGTH: 36
<212> TYPE: PRT
<213> ORGANISM: homo sapiens
```

```
<220> FEATURE:
<221> NAME/KEY: MISC_FEATURE
<222> LOCATION: (12)..(12)
<223> OTHER INFORMATION: Xaa = any amino acid
      provided that the mutant domain is not wild type

<400> SEQUENCE: 76

Arg Ser Pro Pro Asp Gly Gln Ser Phe Arg Ser Xaa Ser Phe Glu Lys
1               5                   10                  15

Pro Arg Gln Pro Ser Gln Ala Asp Thr Gly Gly Asp Asp Ser Asp Glu
            20                  25                  30

Asp Tyr Glu Lys
        35

<210> SEQ ID NO 77
<211> LENGTH: 36
<212> TYPE: PRT
<213> ORGANISM: homo sapiens
<220> FEATURE:
<221> NAME/KEY: MISC_FEATURE
<222> LOCATION: (13)..(13)
<223> OTHER INFORMATION: Xaa = any amino acid
      provided that the mutant domain is not wild type

<400> SEQUENCE: 77

Arg Ser Pro Pro Asp Gly Gln Ser Phe Arg Ser Phe Xaa Phe Glu Lys
1               5                   10                  15

Pro Arg Gln Pro Ser Gln Ala Asp Thr Gly Gly Asp Asp Ser Asp Glu
            20                  25                  30

Asp Tyr Glu Lys
        35

<210> SEQ ID NO 78
<211> LENGTH: 36
<212> TYPE: PRT
<213> ORGANISM: homo sapiens
<220> FEATURE:
<221> NAME/KEY: MISC_FEATURE
<222> LOCATION: (14)..(14)
<223> OTHER INFORMATION: Xaa = any amino acid
      provided that the mutant domain is not wild type

<400> SEQUENCE: 78

Arg Ser Pro Pro Asp Gly Gln Ser Phe Arg Ser Phe Ser Xaa Glu Lys
1               5                   10                  15

Pro Arg Gln Pro Ser Gln Ala Asp Thr Gly Gly Asp Asp Ser Asp Glu
            20                  25                  30

Asp Tyr Glu Lys
        35

<210> SEQ ID NO 79
<211> LENGTH: 36
<212> TYPE: PRT
<213> ORGANISM: homo sapiens
<220> FEATURE:
<221> NAME/KEY: MISC_FEATURE
<222> LOCATION: (15)..(15)
<223> OTHER INFORMATION: Xaa = any amino acid
      provided that the mutant domain is not wild type

<400> SEQUENCE: 79

Arg Ser Pro Pro Asp Gly Gln Ser Phe Arg Ser Phe Ser Phe Xaa Lys
1               5                   10                  15

Pro Arg Gln Pro Ser Gln Ala Asp Thr Gly Gly Asp Asp Ser Asp Glu
            20                  25                  30
```

Asp Tyr Glu Lys
        35

<210> SEQ ID NO 80
<211> LENGTH: 36
<212> TYPE: PRT
<213> ORGANISM: homo sapiens
<220> FEATURE:
<221> NAME/KEY: MISC_FEATURE
<222> LOCATION: (16)..(16)
<223> OTHER INFORMATION: Xaa = any amino acid
      provided that the mutant domain is not wild type

<400> SEQUENCE: 80

Arg Ser Pro Pro Asp Gly Gln Ser Phe Arg Ser Phe Ser Phe Glu Xaa
1               5                   10                  15

Pro Arg Gln Pro Ser Gln Ala Asp Thr Gly Gly Asp Asp Ser Asp Glu
            20                  25                  30

Asp Tyr Glu Lys
        35

<210> SEQ ID NO 81
<211> LENGTH: 36
<212> TYPE: PRT
<213> ORGANISM: homo sapiens
<220> FEATURE:
<221> NAME/KEY: MISC_FEATURE
<222> LOCATION: (17)..(17)
<223> OTHER INFORMATION: Xaa = any amino acid
      provided that the mutant domain is not wild type

<400> SEQUENCE: 81

Arg Ser Pro Pro Asp Gly Gln Ser Phe Arg Ser Phe Ser Phe Glu Lys
1               5                   10                  15

Xaa Arg Gln Pro Ser Gln Ala Asp Thr Gly Gly Asp Asp Ser Asp Glu
            20                  25                  30

Asp Tyr Glu Lys
        35

<210> SEQ ID NO 82
<211> LENGTH: 36
<212> TYPE: PRT
<213> ORGANISM: homo sapiens
<220> FEATURE:
<221> NAME/KEY: MISC_FEATURE
<222> LOCATION: (18)..(18)
<223> OTHER INFORMATION: Xaa = any amino acid
      provided that the mutant domain is not wild type

<400> SEQUENCE: 82

Arg Ser Pro Pro Asp Gly Gln Ser Phe Arg Ser Phe Ser Phe Glu Lys
1               5                   10                  15

Pro Xaa Gln Pro Ser Gln Ala Asp Thr Gly Gly Asp Asp Ser Asp Glu
            20                  25                  30

Asp Tyr Glu Lys
        35

<210> SEQ ID NO 83
<211> LENGTH: 36
<212> TYPE: PRT
<213> ORGANISM: homo sapiens
<220> FEATURE:
<221> NAME/KEY: MISC_FEATURE
<222> LOCATION: (19)..(19)
<223> OTHER INFORMATION: Xaa = any amino acid provided that the mutant domain is not wild type

<400> SEQUENCE: 83

Arg Ser Pro Pro Asp Gly Gln Ser Phe Arg Ser Phe Ser Phe Glu Lys
1               5                   10                  15

Pro Arg Xaa Pro Ser Gln Ala Asp Thr Gly Gly Asp Asp Ser Asp Glu
            20                  25                  30

Asp Tyr Glu Lys
            35

<210> SEQ ID NO 84
<211> LENGTH: 36
<212> TYPE: PRT
<213> ORGANISM: homo sapiens
<220> FEATURE:
<221> NAME/KEY: MISC_FEATURE
<222> LOCATION: (20)..(20)
<223> OTHER INFORMATION: Xaa = any amino acid
      provided that the mutant domain is not wild type

<400> SEQUENCE: 84

Arg Ser Pro Pro Asp Gly Gln Ser Phe Arg Ser Phe Ser Phe Glu Lys
1               5                   10                  15

Pro Arg Gln Xaa Ser Gln Ala Asp Thr Gly Gly Asp Asp Ser Asp Glu
            20                  25                  30

Asp Tyr Glu Lys
            35

<210> SEQ ID NO 85
<211> LENGTH: 36
<212> TYPE: PRT
<213> ORGANISM: homo sapiens
<220> FEATURE:
<221> NAME/KEY: MISC_FEATURE
<222> LOCATION: (21)..(21)
<223> OTHER INFORMATION: Xaa = any amino acid
      provided that the mutant domain is not wild type

<400> SEQUENCE: 85

Arg Ser Pro Pro Asp Gly Gln Ser Phe Arg Ser Phe Ser Phe Glu Lys
1               5                   10                  15

Pro Arg Gln Pro Xaa Gln Ala Asp Thr Gly Gly Asp Asp Ser Asp Glu
            20                  25                  30

Asp Tyr Glu Lys
            35

<210> SEQ ID NO 86
<211> LENGTH: 36
<212> TYPE: PRT
<213> ORGANISM: homo sapiens
<220> FEATURE:
<221> NAME/KEY: MISC_FEATURE
<222> LOCATION: (22)..(22)
<223> OTHER INFORMATION: Xaa = any amino acid
      provided that the mutant domain is not wild type

<400> SEQUENCE: 86

Arg Ser Pro Pro Asp Gly Gln Ser Phe Arg Ser Phe Ser Phe Glu Lys
1               5                   10                  15

Pro Arg Gln Pro Ser Xaa Ala Asp Thr Gly Gly Asp Asp Ser Asp Glu
            20                  25                  30

Asp Tyr Glu Lys
            35

<210> SEQ ID NO 87
<211> LENGTH: 36
<212> TYPE: PRT
<213> ORGANISM: homo sapiens
<220> FEATURE:
<221> NAME/KEY: MISC_FEATURE
<222> LOCATION: (23)..(23)
<223> OTHER INFORMATION: Xaa = any amino acid
      provided that the mutant domain is not wild type

<400> SEQUENCE: 87

Arg Ser Pro Pro Asp Gly Gln Ser Phe Arg Ser Phe Ser Phe Glu Lys
1               5                   10                  15

Pro Arg Gln Pro Ser Gln Xaa Asp Thr Gly Gly Asp Asp Ser Asp Glu
            20                  25                  30

Asp Tyr Glu Lys
        35

<210> SEQ ID NO 88
<211> LENGTH: 36
<212> TYPE: PRT
<213> ORGANISM: homo sapiens
<220> FEATURE:
<221> NAME/KEY: MISC_FEATURE
<222> LOCATION: (24)..(24)
<223> OTHER INFORMATION: Xaa = any amino acid
      provided that the mutant domain is not wild type

<400> SEQUENCE: 88

Arg Ser Pro Pro Asp Gly Gln Ser Phe Arg Ser Phe Ser Phe Glu Lys
1               5                   10                  15

Pro Arg Gln Pro Ser Gln Ala Xaa Thr Gly Gly Asp Asp Ser Asp Glu
            20                  25                  30

Asp Tyr Glu Lys
        35

<210> SEQ ID NO 89
<211> LENGTH: 36
<212> TYPE: PRT
<213> ORGANISM: homo sapiens
<220> FEATURE:
<221> NAME/KEY: MISC_FEATURE
<222> LOCATION: (25)..(25)
<223> OTHER INFORMATION: Xaa = any amino acid
      provided that the mutant domain is not wild type

<400> SEQUENCE: 89

Arg Ser Pro Pro Asp Gly Gln Ser Phe Arg Ser Phe Ser Phe Glu Lys
1               5                   10                  15

Pro Arg Gln Pro Ser Gln Ala Asp Xaa Gly Gly Asp Asp Ser Asp Glu
            20                  25                  30

Asp Tyr Glu Lys
        35

<210> SEQ ID NO 90
<211> LENGTH: 36
<212> TYPE: PRT
<213> ORGANISM: homo sapiens
<220> FEATURE:
<221> NAME/KEY: MISC_FEATURE
<222> LOCATION: (26)..(26)
<223> OTHER INFORMATION: Xaa = any amino acid
      provided that the mutant domain is not wild type

<400> SEQUENCE: 90

```
Arg Ser Pro Pro Asp Gly Gln Ser Phe Arg Ser Phe Ser Phe Glu Lys
1               5                   10                  15

Pro Arg Gln Pro Ser Gln Ala Asp Thr Xaa Gly Asp Asp Ser Asp Glu
            20                  25                  30

Asp Tyr Glu Lys
        35

<210> SEQ ID NO 91
<211> LENGTH: 36
<212> TYPE: PRT
<213> ORGANISM: homo sapiens
<220> FEATURE:
<221> NAME/KEY: MISC_FEATURE
<222> LOCATION: (27)..(27)
<223> OTHER INFORMATION: Xaa = any amino acid
      provided that the mutant domain is not wild type

<400> SEQUENCE: 91

Arg Ser Pro Pro Asp Gly Gln Ser Phe Arg Ser Phe Ser Phe Glu Lys
1               5                   10                  15

Pro Arg Gln Pro Ser Gln Ala Asp Thr Gly Xaa Asp Asp Ser Asp Glu
            20                  25                  30

Asp Tyr Glu Lys
        35

<210> SEQ ID NO 92
<211> LENGTH: 36
<212> TYPE: PRT
<213> ORGANISM: homo sapiens
<220> FEATURE:
<221> NAME/KEY: MISC_FEATURE
<222> LOCATION: (28)..(28)
<223> OTHER INFORMATION: Xaa = any amino acid
      provided that the mutant domain is not wild type

<400> SEQUENCE: 92

Arg Ser Pro Pro Asp Gly Gln Ser Phe Arg Ser Phe Ser Phe Glu Lys
1               5                   10                  15

Pro Arg Gln Pro Ser Gln Ala Asp Thr Gly Gly Xaa Asp Ser Asp Glu
            20                  25                  30

Asp Tyr Glu Lys
        35

<210> SEQ ID NO 93
<211> LENGTH: 36
<212> TYPE: PRT
<213> ORGANISM: homo sapiens
<220> FEATURE:
<221> NAME/KEY: MISC_FEATURE
<222> LOCATION: (29)..(29)
<223> OTHER INFORMATION: Xaa = any amino acid
      provided that the mutant domain is not wild type

<400> SEQUENCE: 93

Arg Ser Pro Pro Asp Gly Gln Ser Phe Arg Ser Phe Ser Phe Glu Lys
1               5                   10                  15

Pro Arg Gln Pro Ser Gln Ala Asp Thr Gly Gly Asp Xaa Ser Asp Glu
            20                  25                  30

Asp Tyr Glu Lys
        35

<210> SEQ ID NO 94
<211> LENGTH: 36
<212> TYPE: PRT
```

```
<213> ORGANISM: homo sapiens
<220> FEATURE:
<221> NAME/KEY: MISC_FEATURE
<222> LOCATION: (30)..(30)
<223> OTHER INFORMATION: Xaa = any amino acid
      provided that the mutant domain is not wild type

<400> SEQUENCE: 94

Arg Ser Pro Pro Asp Gly Gln Ser Phe Arg Ser Phe Ser Phe Glu Lys
1               5                   10                  15

Pro Arg Gln Pro Ser Gln Ala Asp Thr Gly Gly Asp Asp Xaa Asp Glu
            20                  25                  30

Asp Tyr Glu Lys
        35

<210> SEQ ID NO 95
<211> LENGTH: 36
<212> TYPE: PRT
<213> ORGANISM: homo sapiens
<220> FEATURE:
<221> NAME/KEY: MISC_FEATURE
<222> LOCATION: (31)..(31)
<223> OTHER INFORMATION: Xaa = any amino acid
      provided that the mutant domain is not wild type

<400> SEQUENCE: 95

Arg Ser Pro Pro Asp Gly Gln Ser Phe Arg Ser Phe Ser Phe Glu Lys
1               5                   10                  15

Pro Arg Gln Pro Ser Gln Ala Asp Thr Gly Gly Asp Asp Ser Xaa Glu
            20                  25                  30

Asp Tyr Glu Lys
        35

<210> SEQ ID NO 96
<211> LENGTH: 36
<212> TYPE: PRT
<213> ORGANISM: homo sapiens
<220> FEATURE:
<221> NAME/KEY: MISC_FEATURE
<222> LOCATION: (32)..(32)
<223> OTHER INFORMATION: Xaa = any amino acid
      provided that the mutant domain is not wild type

<400> SEQUENCE: 96

Arg Ser Pro Pro Asp Gly Gln Ser Phe Arg Ser Phe Ser Phe Glu Lys
1               5                   10                  15

Pro Arg Gln Pro Ser Gln Ala Asp Thr Gly Gly Asp Asp Ser Asp Xaa
            20                  25                  30

Asp Tyr Glu Lys
        35

<210> SEQ ID NO 97
<211> LENGTH: 36
<212> TYPE: PRT
<213> ORGANISM: homo sapiens
<220> FEATURE:
<221> NAME/KEY: MISC_FEATURE
<222> LOCATION: (33)..(33)
<223> OTHER INFORMATION: Xaa = any amino acid
      provided that the mutant domain is not wild type

<400> SEQUENCE: 97

Arg Ser Pro Pro Asp Gly Gln Ser Phe Arg Ser Phe Ser Phe Glu Lys
1               5                   10                  15

Pro Arg Gln Pro Ser Gln Ala Asp Thr Gly Gly Asp Asp Ser Asp Glu
```

```
                  20                  25                  30

Xaa Tyr Glu Lys
        35

<210> SEQ ID NO 98
<211> LENGTH: 36
<212> TYPE: PRT
<213> ORGANISM: homo sapiens
<220> FEATURE:
<221> NAME/KEY: MISC_FEATURE
<222> LOCATION: (34)..(34)
<223> OTHER INFORMATION: Xaa = any amino acid
      provided that the mutant domain is not wild type

<400> SEQUENCE: 98

Arg Ser Pro Pro Asp Gly Gln Ser Phe Arg Ser Phe Ser Phe Glu Lys
1               5                   10                  15

Pro Arg Gln Pro Ser Gln Ala Asp Thr Gly Gly Asp Asp Ser Asp Glu
            20                  25                  30

Asp Xaa Glu Lys
        35

<210> SEQ ID NO 99
<211> LENGTH: 36
<212> TYPE: PRT
<213> ORGANISM: homo sapiens
<220> FEATURE:
<221> NAME/KEY: MISC_FEATURE
<222> LOCATION: (35)..(35)
<223> OTHER INFORMATION: Xaa = any amino acid
      provided that the mutant domain is not wild type

<400> SEQUENCE: 99

Arg Ser Pro Pro Asp Gly Gln Ser Phe Arg Ser Phe Ser Phe Glu Lys
1               5                   10                  15

Pro Arg Gln Pro Ser Gln Ala Asp Thr Gly Gly Asp Asp Ser Asp Glu
            20                  25                  30

Asp Tyr Xaa Lys
        35

<210> SEQ ID NO 100
<211> LENGTH: 36
<212> TYPE: PRT
<213> ORGANISM: homo sapiens
<220> FEATURE:
<221> NAME/KEY: MISC_FEATURE
<222> LOCATION: (36)..(36)
<223> OTHER INFORMATION: Xaa = any amino acid
      provided that the mutant domain is not wild type

<400> SEQUENCE: 100

Arg Ser Pro Pro Asp Gly Gln Ser Phe Arg Ser Phe Ser Phe Glu Lys
1               5                   10                  15

Pro Arg Gln Pro Ser Gln Ala Asp Thr Gly Gly Asp Asp Ser Asp Glu
            20                  25                  30

Asp Tyr Glu Xaa
        35

<210> SEQ ID NO 101
<211> LENGTH: 109
<212> TYPE: DNA
<213> ORGANISM: homo sapiens

<400> SEQUENCE: 101
```

```
gcgatcaccc cccgatgggc agagtttcag gagcttctcc tttgaaaagc cccggcaacc    60
ctcacaggct gacactggcg gggacgactc ggacgaggac tatgagaag              109
```

<210> SEQ ID NO 102
<211> LENGTH: 36
<212> TYPE: PRT
<213> ORGANISM: homo sapiens

<400> SEQUENCE: 102

Arg Ser Pro Pro Asp Gly Gln Ser Phe Arg Ser Phe Ser Phe Glu Lys
1               5                   10                  15

Pro Arg Gln Pro Ser Gln Ala Asp Thr Gly Gly Asp Asp Ser Asp Glu
            20                  25                  30

Asp Tyr Glu Lys
        35

<210> SEQ ID NO 103
<211> LENGTH: 10
<212> TYPE: PRT
<213> ORGANISM: homo sapiens

<400> SEQUENCE: 103

Pro Pro Ala Tyr Pro Pro Pro Val Pro
1               5                   10

<210> SEQ ID NO 104
<211> LENGTH: 6
<212> TYPE: PRT
<213> ORGANISM: homo sapiens

<400> SEQUENCE: 104

Arg Ser Pro Pro Asp Gly
1               5

<210> SEQ ID NO 105
<211> LENGTH: 12
<212> TYPE: PRT
<213> ORGANISM: homo sapiens

<400> SEQUENCE: 105

His Leu Gln Arg Ser Pro Pro Asp Gly Gln Ser Phe
1               5                   10

<210> SEQ ID NO 106
<211> LENGTH: 23
<212> TYPE: DNA
<213> ORGANISM: homo sapiens

<400> SEQUENCE: 106

```
gcgatcaccc cccgatgggc aga                                          23
```

<210> SEQ ID NO 107
<211> LENGTH: 23
<212> TYPE: DNA
<213> ORGANISM: homo sapiens

<400> SEQUENCE: 107

```
gcsatcaccc cccgatgggc aga                                          23
```

<210> SEQ ID NO 108
<211> LENGTH: 23
<212> TYPE: DNA
<213> ORGANISM: homo sapiens

```
<400> SEQUENCE: 108
gcratcaccc cccgatgggc aga                                              23

<210> SEQ ID NO 109
<211> LENGTH: 23
<212> TYPE: DNA
<213> ORGANISM: homo sapiens

<400> SEQUENCE: 109
gcgatcaccc cycgatgggc aga                                              23

<210> SEQ ID NO 110
<211> LENGTH: 23
<212> TYPE: DNA
<213> ORGANISM: homo sapiens

<400> SEQUENCE: 110
gcgatcaccc cscgatgggc aga                                              23

<210> SEQ ID NO 111
<211> LENGTH: 23
<212> TYPE: DNA
<213> ORGANISM: homo sapiens

<400> SEQUENCE: 111
gcgatcaccc cmcgatgggc aga                                              23

<210> SEQ ID NO 112
<211> LENGTH: 23
<212> TYPE: DNA
<213> ORGANISM: homo sapiens

<400> SEQUENCE: 112
gcgatcaccc cccgatgrgc aga                                              23

<210> SEQ ID NO 113
<211> LENGTH: 23
<212> TYPE: DNA
<213> ORGANISM: homo sapiens

<400> SEQUENCE: 113
gcgatcaccc cccgatsggc aga                                              23
```

METHODS FOR EVALUATING SUSCEPTIBILITY TO A BONE HOMEOSTASIS DISORDER

GOVERNMENT SUPPORT

This application was made with government support under grant numbers AR36819 and AR36820 awarded by the National Institutes of Health. The United States Government has certain rights in the invention.

RELATED APPLICATIONS

This application is a national stage filing under U.S.C. § 371 of PCT International application PCT/US2002/19164, filed Feb. 1, 2002, which was published under PCT Article 21(2) in English, and which claims the benefit under 35 U.S.C. § 119 of U.S. provisional application Ser. No. 60/266,129, filed Feb. 2, 2001.

FIELD OF THE INVENTION

This invention relates to nucleic acids and polypeptides derived from a mutant SH3-binding protein (SH3BP2) gene. The mutant gene differs from the wild type SH3BP2 gene in containing one or more point mutations. The nucleic acid molecules and encoded polypeptides are useful in, inter alia, research, diagnostic and therapeutic contexts, particularly for the development of antibodies and anti-sense molecules for treating disorders of bone homeostasis.

BACKGROUND OF THE INVENTION

The remodeling of bone is a dynamic process. Cells continuously lay down and resorb bone material. Bone homeostasis refers to the balance between bone formation and bone degradation. An imbalance in the activity of cells that lay down new bone (osteoblasts) and cells that resorb bone (osteoclasts) can result in serious, and sometimes fatal, disorders. Thus, imbalances in bone homeostasis are associated with a variety of adverse medical conditions.

Osteoporosis is a term used for a number of diseases of diverse etiology, all involving a reduction in the mass of bone per unit volume. Osteoporosis is the most common of the metabolic bone diseases. Twenty-five million people in the United States and more than two hundred million people worldwide are affected by osteoporosis. Osteoporosis is frequent among post-menopausal women and is an important cause of morbidity in the elderly. It commonly results in bone fractures, and death can be a frequent occurrence in the months following fractures, particularly those of the hip in elderly individuals.

Osteopetrosis is a disorder involving an increase in the mass of bone per unit volume. Its incidence is rare compared to osteoporosis, but it typically is life threatening. Despite having multiple causes, a defect in bone resorption is always the underlying mechanism. In many instances, the disorder is inherited as an autosomal recessive trait and involves abnormal osteoclast function. Bone marrow transplants from normal donors have been attempted to restore normal osteoclast precursor cells, but this therapy has shown only limited success. Present treatments for disorders of bone homeostasis are inadequate.

In view of the foregoing, a need exists to develop new and improved methods and compositions for treating disorders of bone homeostasis. Preferably such methods and compositions are based upon inhibiting the particular interactions between cell components which mediate the abnormal physiological effect, thereby minimizing harmful side effects that may be due to non-specific therapeutic approaches.

SUMMARY OF THE INVENTION

The invention is based, in part, on our discovery of point mutations that cause amino acid substitutions in the SH3-binding protein SH3BP2. We have collected samples from 15 families, consisting of 66 individuals clinically diagnosed with cherubism (an exemplary bone homeostasis disorder), 4 obligate carriers, and 79 unaffected subjects. In 12 families, where mutations were found, the mutations co-segregate with the disease phenotype. We also cloned SH3BP2 cDNA from EBV-transformed patient lymphoblasts into TA-vectors and sequenced them. Half of the sequenced clones from each patient carried the mutation. We sequenced genomic DNAs from 100 unrelated and unaffected African-Brazilians and 100 Caucasian controls without detecting any of the sequence variants found in affected cherubism patients. The accumulation of co-segregating sequence variants in families with cherubism and their absence in unaffected controls provide compelling evidence that the mutations in SH3BP2 cause cherubism. In view of the foregoing discoveries, the mutant SH3BP2 molecules disclosed herein have a variety of uses including, for example, diagnostic applications (e.g., genetic testing including amniocentesis); screening methods to identify agents that are useful for treating bone homeostasis disorders such as cherubism, osteoporosis, osteopetrosis, and bone tumors (malignant or benign); and therapeutic applications that utilize the compositions of the invention (e.g., antibodies selective for mutant SH3BP2 epitope, antisense) for treating bone homeostasis disorders. These and other aspects of the invention are summarized below.

According to a first aspect of the invention, an isolated nucleic acid molecule is provided. The isolated nucleic acid molecule includes:

(a) nucleic acid molecules which hybridize under stringent conditions to a nucleic acid molecule comprising a sequence selected from the group consisting of SEQ ID NO:5 (generic mutant—full length); SEQ ID NO:7 (generic mutant domain); SEQ ID NO:9 ("H" family mutation), SEQ ID NO:11 ("K" family mutation), SEQ ID NO:13 ("A,B" family mutation), SEQ ID NO:15 ("C,F,J,M,O" family mutation), SEQ ID NO:17 ("L" family mutation), SEQ ID NO: 19 ("G" family mutation), SEQ ID NO:21 ("N" family mutation), SEQ ID NO:26 (genomic mutant SH3BP2), SEQ ID NOs: 27-63 (mutant SH3BP2 exon 9) and a genomic mutant SH3BP2 nucleic acid molecule having a sequence identical to SEQ ID NO: 25 with the exception that a mutant exon 9 selected from the group consisting of SEQ ID NOs: 27-63 is used in place of the wild type exon 9, (b) nucleic acid molecules that differ from the nucleic acid molecules of (a) in codon sequence due to the degeneracy of the genetic code, and (c) complements of (a) or (b) (e.g., antisense to the mutant SH3BP2 domain SEQ ID NO:7), provided that the nucleic acid molecule is not SEQ ID NO:1 (human "WT" SH3BP2 full length sequence) or SEQ ID NO: 25 (human WT genomic). In certain preferred embodiments, the nucleic acid molecule also is not SEQ ID NO:3 (human WT domain) or SEQ ID NO:102 (human WT exon 9). In these and/or other preferred embodiments, the isolated nucleic acid molecules of the invention do not hybridize under stringent conditions to a sequence selected from the group consisting of SEQ ID NO:1 (human "WT" SH3BP2 full length sequence), SEQ ID NO:3 (human WT domain), SEQ ID NO: 25 (human WT genomic), and SEQ ID NO:101 (human WT exon 9). An abbreviated Sequence Listing which identifies the sequence and/or GenBank accession number information for the sequences relating to the invention is provided herewith as Table 1.

In preferred embodiments, the isolated nucleic acid molecule of the invention has a sequence selected from the group consisting of SEQ ID NO:5 (generic mutant—full length); SEQ ID NO:7 (generic mutant domain); SEQ ID NO:9 ("H" family mutation), SEQ ID NO:11 ("K" family mutation), SEQ ID NO:13 ("A,B" family mutation), SEQ ID NO:15 ("C,F,J,M,O" family mutation), SEQ ID NO:17 ("L" family mutation), SEQ ID NO:19 ("G" family mutation), SEQ ID NO:21 ("N" family mutation), SEQ ID NO:26 (genomic mutant SH3BP2), SEQ ID NOs:27-63 (mutant SH3BP2 exon 9) and a genomic mutant SH3BP2 nucleic acid molecule having a sequence identical to SEQ ID NO: 25 with the exception that a mutant exon 9 selected from the group consisting of SEQ ID NOs: 27-63 is used in place of the wild type exon 9. In these and other embodiments, the preferred isolated nucleic acid molecules of the invention code for a polypeptide having a sequence selected from the group consisting of SEQ ID NO:6, SEQ ID NO:8, SEQ ID NO:10, SEQ ID NO: 12, SEQ ID NO:14, SEQ ID NO:16, SEQ ID NO:18, SEQ ID NO:20, SEQ ID NO:22, and SEQ ID NOs:64-100.

According to yet another aspect of the invention, primers for amplifying the above-identified nucleic acid sequences are provided. In this aspect, the preferred isolated nucleic acid molecules are selected from the group consisting of (a) a nucleic acid molecule having a sequence selected from the group consisting of SEQ ID NO:23, 24 and other sequences which are capable of Is hybridizing to an SH3BP2 mutant molecule and, thereby, are useful in amplifying exon 9 in a mutant SH3BP3 nucleic acid molecule, and (b) complements of (a).

The invention also embraces expression vectors containing the isolated nucleic acid molecules of the invention, operably linked to a promoter, as well as host cells transformed or transfected with such expression vectors.

Pharmaceutical compositions comprising the compositions of the invention, as well as methods for making such medicaments also are provided.

Transgenic non-human animals having somatic and germ line cells that contain any of the isolated SH3BP2 mutant nucleic acid molecules of the invention also are provided. Preferably, the expression of the SH3BP2 mutant nucleic acid molecule results in the animal having a bone homeostasis disorder. Suck animals are useful as models of human bone homeostasis disorders.

According to another aspect of the invention, isolated polypeptides encoded by any of the isolated nucleic acid molecules of the invention are provided. Preferably, the isolated polypeptides of the invention include a sequence selected from the group consisting of SEQ ID NO:6, SEQ ID NO:8, SEQ ID NO:10, SEQ ID NO: 12, SEQ ID NO:14, SEQ ID NO:16, SEQ ID NO:18, SEQ ID NO:20, SEQ ID NO:22, and SEQ ID Nos:64-100.

According to still another aspect of the invention, compositions containing an isolated binding agent that binds selectively to a nucleic acid molecule or to a polypeptide molecule of the invention also are provided. In certain embodiments, the isolated binding agent is a nucleic acid (e.g., an antisense, a ribozyme); in yet other embodiments, the isolated binding agent is a peptide (e.g., an antibody, or a fragment thereof).

According to another aspect of the invention, a method of identifying the presence of an SH3BP2 mutant molecule in a sample is provided. In general, the method involves analyzing the sample for the presence of a SH3BP2 mutant nucleic acid molecule or a SH3BP2 mutant polypeptide.

In certain embodiments, the method further involves the steps of contacting the sample with at least two nucleic acid amplification primers and amplifying DNA in the sample prior to analyzing the sample for the presence of a SH3BP2 mutant nucleic acid molecule. The method employs a first nucleic acid amplification primer and a second nucleic acid amplification primer that are capable of hybridizing to a SH3BP2 mutant nucleic acid molecule and, thereby, are useful in amplifying a nucleic acid comprising a sequence selected from the group consisting of SEQ ID NO:5 (generic mutant—full length); SEQ ID NO:7 (generic mutant domain); SEQ ID NO:9 ("H" family mutation), SEQ ID NO:11 ("K" family mutation), SEQ ID NO:13 ("A,B" family mutation), SEQ ID NO:15 ("C,F,J,M,O" family mutation), SEQ ID NO:17 ("L" family mutation), SEQ ID NO:19 ("G" family mutation), SEQ ID NO:21 ("N" family mutation), SEQ ID NO:26 (genomic mutant SH3BP2), SEQ ID NOs: 27-63 (mutant SH3BP2 exon 9) and a genomic mutant SH3BP2 nucleic acid molecule having a sequence identical to SEQ ID NO:25 with the exception that a mutant exon 9 selected from the group consisting of SEQ ID NOs: 27-63 is used in place of the wild type exon 9. Following hybridization, the method involves amplifying a primed nucleic acid molecule which hybridizes to the first and the second nucleic acid amplification primers; and detecting the presence of an amplified nucleic acid molecule in the sample.

In yet other embodiments, the method involves contacting the sample with one or more nucleic acid probes, wherein the nucleic acid probe is capable of hybridizing to a nucleic acid sequence selected from the group consisting of: nucleic acid sequences which hybridize to a sequence selected from one or more of the following sequences under stringent conditions: SEQ ID NO:5 (generic mutant—full length); SEQ ID NO:7 (generic mutant domain); SEQ ID NO:9 ("H" family mutation), SEQ ID NO:11 ("K" family mutation), SEQ ID NO:13 ("A,B" family mutation), SEQ ID NO:15 ("C,F,J,M,O" family mutation), SEQ ID NO:17 ("L" family mutation), SEQ ID NO:19 ("G" family mutation), SEQ ID NO:21 ("N" family mutation), SEQ ID NO:26 (genomic mutant SH3BP2), SEQ ID NOs:27-63 (mutant SH3BP2 exon 9) and a genomic mutant SH3BP2 nucleic acid molecule having a sequence identical to SEQ ID NO: 25 with the exception that a mutant exon 9 selected from the group consisting of SEQ ID NOs: 27-63 is used in place of the wild type exon 9 and, preferably, which does not hybridize to SEQ ID NO:1 (human "WT" SH3BP2 full length sequence), SEQ ID NO:3 (human WT domain), SEQ ID NO:25 (human WT genomic) or SEQ ID NO:101 (human WT exon 9), under stringent conditions, and detecting the presence of a SH3BP2 mutant nucleic acid in the sample which hybridizes to the nucleic acid probe.

In yet other embodiments, the method involves contacting the sample with one or more binding agents, wherein the binding agent is capable of selectively binding to a polypeptide having an amino acid sequence selected from the group consisting of: SEQ ID NO:6, SEQ ID NO:8, SEQ ID NO:10, SEQ ID NO: 12, SEQ ID NO:14, SEQ ID NO:16, SEQ ID NO:18, SEQ ID NO:20, SEQ ID NO:22, and SEQ ID Nos: 64-100; and detecting the presence of a SH3BP2 mutant polypeptide in the sample which binds the binding agent. Preferably, the binding agent is an antibody or a fragment thereof that selectively binds to the SH3BP2 mutant polypeptide in the sample and does not bind to a non-mutant SH3BP2 polypeptide that may be present in the sample.

The diagnostic methods of the invention are particularly useful for: evaluating the susceptibility of a human subject to a disorder of bone homeostasis, evaluating causation of a bone homeostasis disorder in a human subject, or for evaluating the genetic predisposition of a human subject to have offspring with a bone homeostasis disorder. Such methods differ primarily in the selection of the human subject (e.g., the human subject exhibits a bone homeostasis disorder or is suspected of having a predisposition to developing the disorder or having offspring susceptible of developing the disorder). In general, such methods involve obtaining a sample of DNA from the subject; and evaluating the sample of DNA for the presence of nucleotides encoding a "mutant residue" at any one or more amino acid positions encoded by exon 9 of the SH3BP2 gene product. In certain preferred embodiments, the sample of DNA is evaluated for the presence of nucleotides encoding a "mutant residue" at any one or more amino acids encoded by exon 9, particularly at positions 415-420, inclusive, and, more particularly, at positions 415, 418, and 420, of the SH3BP2 gene product. The presence of a mutant residue is indicative of the condition for which the subject is being tested. Functional activity of a mutant SH3BP2 molecule can be determined, for example, by observing a detectable phenotype indicative of a bone homeostasis disorder as disclosed herein. Exemplary mutant residues that are diagnostic of cherubism are described in more detail in the Examples.

According to yet another aspect of the invention, a method of screening for an agent that inhibits the production of a SH3BP2 mutant polypeptide is provided. The method involves: (a) determining the level of a SH3BP2 mutant molecule (e.g., nucleic acid, polypeptide) in the absence of a putative inhibitor, (b) determining the level of a SH3BP2 mutant molecule in the presence of the putative inhibitor, and (c) comparing the level of the SH3BP2 mutant molecule in the presence and absence of the putative inhibitor. A decrease in the level of the SH3BP2 mutant molecule in the presence of the putative inhibitor indicates that the putative inhibitor is an agent that inhibits the production of a SH3BP2 mutant polypeptide. In certain embodiments, the agent inhibits transcription of a SH3BP2 mutant nucleic acid molecule. In yet other embodiments, the agent inhibits translation of a SH3BP2 mutant nucleic acid molecule.

According to a further aspect of the invention, a method for treating a subject having a bone homestasis disorder that is further characterized by the presence of a SH3BP2 mutant nucleic acid molecule is provided. The method involves administering a mutant binding molecule (such as an SH3BP2 mutant nucleic acid antisense molecule, or a ribozyme that selectively binds to and cleaves an SH3BP2 mutant nucleic acid) to a subject in need of such treatment in an amount effective to treat the subject, provided the subject is not otherwise in need of mutant SH3BP2 binding molecule treatment. In certain embodiments, the bone homeostasis disorder is selected from the group consisting of osteoporosis, osteopetrosis; bone tumors (malignant or benign); and cherubism. The agent may be administered in accordance with standard clinical practice (e.g., systemic); however, in certain embodiments, the agent is locally administered (e.g., to a periodontal pocket).

The invention also embraces a method of reducing expression of an SH3BP2 mutant nucleic acid molecule in a cell or cell-free system containing a SH3BP2 mutant nucleic acid molecule. The method may be practiced in vivo or in vitro. In general, the method involves introducing a SH3BP2 mutant binding molecule (e.g., an antisense nucleic acid molecule, a ribozyme that selectively binds to and cleaves a SH3BP2 nucleic acid) into the system (e.g., a cell), and allowing the SH3BP2 mutant binding molecule to hybridize to a sense SH3BP2 mutant nucleic acid molecule, thereby inhibiting expression of the sense SH3BP2 mutant nucleic acid molecule.

These and other objects of the invention will be described in further detail in connection with the detailed description of the invention.

BRIEF DESCRIPTION OF THE FIGURES

The figures, if present or referenced in this application, are illustrative only and are not required for enablement of the inventions disclosed herein.

Example 1, FIG. 1—Cherubism patient at age 12 (Family F). The facial swelling in this severe case affects the tipper and lower jaws. The computed tomography 3D image (right) shows excessive bone degradation and replacement by soft tissue masses. Excessive growth of the fibro-osseous tissue results in widening of the mandible; it pushes the orbital floors upward and exposes the sclera. Several teeth are exfoliated due to the bone loss.

Figure 2:
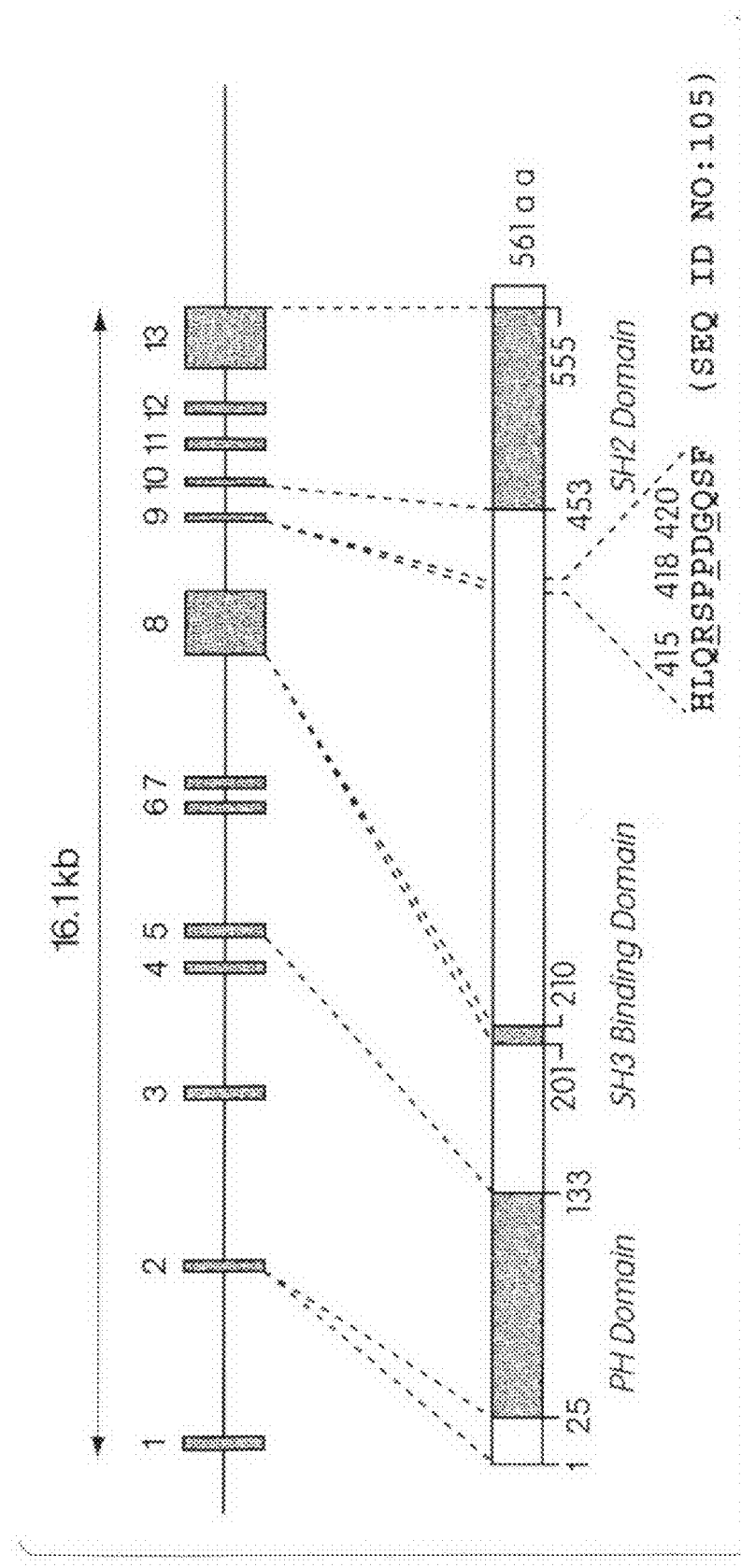

Example 1, FIG. 2—Gene structure and functional domains of SH3BP2. The gene consists of 13 exons extending over a 16.1 kb interval. The 561 amino acid (aa) residue-long protein consists of 3 modular domains (pleckstrin homology (PH) domain, SH3-binding domain, and SH2 domain). All the mutations found in the 12 families are located within a 6 residue-long sequence positioned 31 to 36 residues upstream of the SH2 domain. SEQ ID NO: 105 contains a portion of the amino acid sequence of exon 9.

Example 1, FIG. 3—Electropherograms of partial sequences of exon 9 of the SH3BP2 gene showing the different heterozygous point mutations found in the cherubism families. Arrows (↓) indicate the different heterozygous point mutations. Capital letters next to the sequences indicate wild type sequence (WT) and list the families for which the respective mutation was detected.

FIG. 3A: Wild-type partial sequence of exon 9, SEQ ID NO: 106.

FIG. 3B: Family H partial sequence of exon 9, SEQ ID NO: 107.

FIG. 3C: Family K partial sequence of exon 9, SEQ ID NO: 108.

FIG. 3D: Family A, B partial sequence of exon 9, SEQ ID NO: 109.

FIG. 3E: Family C, F, J, M, O partial sequence of exon 9, SEQ ID NO: 110.

FIG. 3F: Family L partial sequence of exon 9, SEQ ID NO: 111.

FIG. 3G: Family G partial sequence of exon 9, SEQ ID NO: 112.

FIG. 3H: Family N partial sequence of exon 9, SEQ ID NO: 113.

TABLE 1

ABBREVIATED SEQUENCE LISTING

| SEQ ID NO: | DESCRIPTION OF NUCLEOTIDE OR AMINO ACID SEQUENCE |
|---|---|
| 1 (full length wt nucleic acid) | Wild type SH3BP2 cDNA having GenBank Accession No. U56386. |
| 2 (full length wt polypeptide) | Wild type SH3BP2 polypeptide having GenBank Accession No. AAB72034 (encoded by SEQ ID NO: 1). |
| 3 (wt domain) | "Wild type nucleic acid domain" (CGATCACCCCCCGATGGGCAG) at nucleotide positions 1451-1471, inclusive, of SEQ ID NO: 1. |
| 4 (wt domain) | "Wild type polypeptide domain" (RSPPDGQ) at amino acid positions 415-420, inclusive, of SEQ ID NO: 2, encoded by SEQ ID NO: 3. |
| 5 (full length "generic mutant" nucleic acid; generic identifies all possible point mutations) | Generic mutant SH3BP2 cDNA: Sequence is identical to SEQ ID NO: 1 but with "mutant domain" (CXATCACCCCXCGATXXGCAG, SEQ ID NO: 7) in place of wild type domain (CGATCACCCCCCGATGGGCAG, SEQ ID NO: 3) at nucleotide positions 1451-1471, inclusive. |
| 6 (full length "generic mutant" polypeptide) | Generic mutant SH3BP2 polypeptide: encoded by SEQ ID NO: 5. |
| 7 (generic mutant domain) | Generic mutant SH3BP2 nucleic acid "mutant domain": CXATCACCCCXCGATXXGCAG, wherein X is independently selected from the group consisting of S, R, Y, and M (i.e., X can be C, T, G, or A, provided that the mutant domain is not wild type). |
| 8 (generic mutant domain) | Generic mutant SH3BP2 polypeptide "mutant domain": encoded by SEQ ID NO: 7. |
| 9 (Family H) | Family H mutant SH3BP2 cDNA mutant domain: CSATCACCCCCCGATGGGCAG. |
| 10 | Family H mutant SH3BP2 polypeptide mutant domain: encoded by SEQ ID NO: 9. |
| 11 (Family K) | Family K mutant SH3BP2 cDNA mutant domain: CRATCACCCCCCGATGGGCAG. |
| 12 | Family K mutant SH3BP2 polypeptide mutant domain: encoded by SEQ ID NO: 11. |
| 13 (Families A, B) | Family A, B mutant SH3BP2 cDNA mutant domain: CGATCACCCCYCGATGGGCAG. |
| 14 | Family A, B mutant SH3BP2 polypeptide mutant domain: encoded by SEQ ID NO: 13 |
| 15 (Families C, F, J, M, and O) | Family C, F, J, M, O mutant SH3BP2 cDNA mutant domain: CGATCACCCCSCGATGGGCAG. |
| 16 | Family C, F, J, M, O mutant SH3BP2 polypeptide mutant domain: encoded by SEQ ID NO: 15. |
| 17 (Family L) | Family L mutant SH3BP2 cDNA mutant domain: CGATCACCCCMCGATGGGCAG. |
| 18 | Family L mutant SH3BP2 polypeptide mutant domain: encoded by SEQ ID NO: 17 |
| 19 (Family G) | Family G mutant SH3BP2 cDNA mutant domain: CGATCACCCCCCGATGRGCAG. |
| 20 | Family G mutant SH3BP2 polypeptide mutant domain: encoded by SEQ ID NO: 19. |
| 21 (Family N) | Family N mutant SH3BP2 cDNA mutant domain: CGATCACCCCCCGATSGGCAG. |
| 22 | Family N mutant SH3BP2 polypeptide mutant domain: encoded by SEQ ID NO: 21. |
| 23 Primer #1 | SH3BP29F: CTTGCCGTCCTCACACAGAG |
| 24 Primer #2 | SH3BP211R: TTAGGAACTGTGGAGTCCTG |
| 25 Genomic WT | GenBank Z68279 |
| 26 Genomic mutant | Genomic mutant SH3BP2 is identical to SEQ ID NO: 25 with the exception that mutant exon 9 (SEQ ID NO: 27) is used in place of the wild type exon 9. |
| 27-63 | Mutant SH3BP2 exon 9 nucleotide sequences. |
| 64-100 | Mutant SH3BP2 exon 9 amino acid sequences. |
| 101 | Human wild type exon 9 nucleotide sequence. |
| 102 | Human wild type exon 9 amino acid sequence. |
| 103 | PPAYPPPPVP |
| 104 | RSPPDG |
| 105 | HLQRSPPDGQSF |
| 106 | Wild-type partial sequence of exon 9. |
| 107 | Family H partial sequence of exon 9. |
| 108 | Family K partial sequence of exon 9. |
| 109 | Family A, B partial sequence of exon 9. |
| 110 | Family C, F, J, M, O partial sequence of exon 9. |
| 111 | Family L partial sequence of exon 9. |
| 112 | Family G partial sequence of exon 9. |
| 113 | Family N partial sequence of exon 9. |

DETAILED DESCRIPTION OF THE INVENTION

The invention is based, in part, on our discovery of point mutations that cause amino acid substitutions in the SH3-binding protein SH3BP2. We have collected samples from 15 families, consisting of 66 individuals clinically diagnosed with cherubism (an exemplary bone homeostasis disorder), 4 obligate carriers, and 79 unaffected subjects. In 12 families, where mutations were found, the mutations co-segregate with the disease phenotype. We also cloned SH3BP2 cDNA from EBV-transformed patient lymphoblasts into TA-vectors and sequenced them. Half of the sequenced clones from each patient carried the mutation. We sequenced genomic DNAs from 100 unrelated and unaffected African-Brazilians and 100 Caucasian controls without detecting any of the sequence variants found in affected cherubism patients. The accumulation of co-segregating sequence variants in families with cherubism and their absence in unaffected controls provide compelling evidence that the mutations in SH3BP2 cause cherubism. In view of the foregoing discoveries, the mutant SH3BP2 molecules disclosed herein have a variety of uses including, for example, diagnostic applications (e.g., genetic testing); screening methods to identify agents that are useful for treating bone homeostasis disorders such as cherubism, osteoporosis, osteopetrosis, and bone tumors; and therapeutic applications that utilize the compositions of the invention (e.g., antibodies selective for mutant SH3BP2 epitope, antisense, ribozymes) for treating bone homeostasis disorders. These and other aspects of the invention are summarized below.

According to a first aspect of the invention, an isolated nucleic acid molecule is provided. The isolated nucleic acid molecule includes:

(a) nucleic acid molecules which hybridize under stringent conditions to a nucleic acid molecule comprising a sequence selected from the group consisting of SEQ ID NO:5 (generic mutant—full length); SEQ ID NO:7 (generic mutant domain); SEQ ID NO:9 ("H" family mutation), SEQ ID NO:11 ("K" family mutation), SEQ ID NO:13 ("A,B" family mutation), SEQ ID NO:15 ("C,F,J,M,O" family mutation), SEQ ID NO:17 ("L" family mutation), SEQ ID NO: 19 ("G" family mutation), SEQ ID NO:21 ("N" family mutation), SEQ ID NO:26 (genomic mutant SH3BP2), SEQ ID NOs: 27-63 (mutant SH3BP2 exon 9) and a genomic mutant SH3BP2 nucleic acid molecule having a sequence identical to SEQ ID NO: 25 with the exception that a mutant exon 9 selected from the group consisting of SEQ ID NOs: 27-63 is used in place of the wild type exon 9, (b) nucleic acid molecules that differ from the nucleic acid molecules of (a) in codon sequence due to the degeneracy of the genetic code, and (c) complements of (a) or (b) (e.g., antisense to the mutant SH3BP2 domain SEQ ID NO:7), provided that the nucleic acid molecule is not SEQ ID NO:1 (human "WT" SH3BP2 full length sequence) or SEQ ID NO: 25 (human WT genomic). In certain preferred embodiments, the nucleic acid molecule also is not SEQ ID NO:3 (human WT domain) or SEQ ID NO:101 (human WT exon 9). In these and/or other preferred embodiments, the isolated nucleic acid molecules of the invention do not hybridize under stringent conditions to a sequence selected from the group consisting of SEQ ID NO:1 (human "WT" SH3BP2 full length sequence), SEQ ID NO:3 (human WT domain), SEQ ID NO:25 (human WT genomic), and SEQ ID NO:101 (human WT exon 9). An abbreviated Sequence Listing which identifies the sequence and/or GenBank accession number information for the sequences relating to the invention is provided herewith as Table 1.

In preferred embodiments, the isolated nucleic acid molecule of the invention has a sequence selected from the group consisting of SEQ ID NO:5 (generic mutant—full length); SEQ ID NO:7 (generic mutant domain); SEQ ID NO:9 ("H" family mutation), SEQ ID NO:11 ("K" family mutation), SEQ ID NO:13 ("A,B" family mutation), SEQ ID NO:15 ("C,F,J,M,O" family mutation), SEQ ID NO:17 ("L" family mutation), SEQ ID NO: 19 ("G" family mutation), SEQ ID NO:21 ("N" family mutation), SEQ ID NO:26 (genomic mutant SH3BP2), SEQ ID NOs:27-63 (mutant SH3BP2 exon 9) and a genomic mutant SH3BP2 nucleic acid molecule having a sequence identical to SEQ ID NO: 25 with the exception that a mutant exon 9 selected from the group consisting of SEQ ID NOs: 27-63 is used in place of the wild type exon 9. In these and other embodiments, the preferred isolated nucleic acid molecules of the invention code for a polypeptide having a sequence selected from the group consisting of SEQ ID NO:6, SEQ ID NO:8, SEQ ID NO:10, SEQ ID NO: 12, SEQ ID NO:14, SEQ ID NO:16, SEQ ID NO:18, SEQ ID NO:20, SEQ ID NO:22, and SEQ ID Nos:64-100.

As used herein, a mutant SH3BP2 nucleic acid molecule refers to a nucleic acid molecule which contains an SH3BP2-derived nucleotide sequence containing one or more point mutations in exon 9 (e.g., one or more point mutations in a "mutation domain") and which results in a mutant SH3BP2 functional activity (e.g., an activity which can be measured in vitro or which can be determined by detecting a phenotype indicative of a bone homeostasis disorder, such as those disorders disclosed herein). As used herein, a "mutation domain" or a "mutant domain" refers to the nucleotide sequence between nucleotide positions 1451 to 1471, inclusive of the wild type SH3BP2 cDNA sequence (SEQ ID NO:1). The exact number of nucleotide changes in the mutant SH3BP2 compared to the wild type SH3BP2 nucleic acid can vary. In general, the nucleotide changes (one or more point mutations) in the mutant SH3BP2 nucleic acids of the invention are present in exon 9 (including nucleic acid positions 1451 to 1471, inclusive); however, the most common point mutations are those which occur at nucleotide positions 1452, 1461, 1466 and 1467. Table 2 illustrates the mutations in SH3BP2 causing cherubism in the families from which the mutant SH3BP2 sequence was identified. (See, also, FIG. 3.)

TABLE 2

| MUTATIONS IN SH3BP2 CAUSING CHERUBISM | |
|---|---|
| Arg415 (CGA) to Gln (CAA) | Family K |
| Arg415 (CGA) to Pro (CCA) | Family H |
| Pro418 (CCC) to Leu (CTC) | Family A, B |
| Pro418 (CCC) to Arg (CGC) | Family C, J, M, O, F |
| Pro418 (CCC) to His (CAC) | Family L |
| Gly420 (GGG) to Glu (GAG) | Family G |
| Gly420 (GGG) to Arg (CGG) | Family N |

The term "genomic mutant SH3BP2 nucleic acid molecule", as used herein, refers to a mutant SH3BP2 nucleic acid molecule with a nucleic acid sequence identical to the genomic wild-type sequence of SEQ ID NO: 25 with the exception that a mutant exon 9 with a sequence selected from the group consisting of SEQ ID NOs: 27-63 is used in place of the wild-type exon 9 sequence, SEQ ID 101.

The nucleotide changes in the mutant SH3BP2 exon 9 can occur at any nucleotide position within exon 9, provided that the change results in an amino acid change in the polypeptide encoded by exon 9 (1) which is distinct from the human wild type SH3BP2 exon 9 and (2) which exhibits a mutant SH3BP2 functional activity (e.g., a detectable phenotype indicative of a bone homeostasis disorder). Exemplary mutant SH3BP2 exon 9 nucleotide sequences (SEQ ID Nos: 27-63) are provided in Table 3. Exemplary mutant SH3BP2 exon 9 amino acid sequences (SEQ ID Nos:64-100) are provided in Table 4. For reference, Tables 5 and 6 show the wild type SH3BP2 exon positions (SH3BP2 is on the complementary strand of the published GenBank clone Z68279), and the wild type SH3BP2 exon 9 nucleotide and amino acid sequences, respectively.

TABLE 3

MUTANT SH3BP2 EXON 9 NUCLEOTIDE SEQUENCES

| SEQ ID NO. | SEQUENCE |
|---|---|
| 27 | 5'-G 123 TCA CCC 123 CAT 123 GAG AGT TTC AGG AGC TTC TCC TTT GAA AAG CCC CGG CAA CCC TCA CAG GCT GAC ACT GGC GGG GAC GAC TCG GAC GAG GAC TAT GAG AAG-3' |
| 28 | 5'-G 123 TCA CCC CCC GAT GGG CAG AGT TTC AGG AGC TTC TCC TTT GAA AAG CCC CGG CAA CCC TCA CAG GCT GAC ACT GGC GGG GAC GAC TCG GAG GAC TAT GAG AAG-3' |
| 29 | 5'-G CGA 123 CCC CCC GAT GGG CAG AGT TTC AGG AGC TTC TCC TTT GAA AAG CCC CGG CAA CCC TCA CAG GCT GAC ACT GGC GGG GAC GAC TCG GAC GAG GAC TAT GAG AAG-3' |
| 30 | 5'-G CGA TCA 123 CCC GAT GGG CAG AGT TTC AGG AGC TTC TCC TTT GAA AAG CCC CGG CAA CCC TCA CAG GCT GAC ACT GGC GGG GAC GAC TCG GAC GAG GAC TAT GAG AAG-3' |
| 31 | 5'-G CGA TCA CCC 123 GAT GGG CAG AGT TTC AGG AGC TTC TCC TTT GAA AAG CCC CGG CAA CCC TCA CAG GCT GAC ACT GGC GGG GAC GAC TCG GAC GAG GAC TAT GAG AAG-3' |
| 32 | 5'-G CGA TCA CCC CCC 123 GGG CAG AGT TTC AGG AGC TTC TCC TTT GAA AAG CCC CGG CAA CCC TCA CAG GCT GAC ACT GGC GGG GAC GAC TCG GAC GAG GAC TAT GAG AAG-3' |
| 33 | 5'-G CGA TCA CCC CCC GAT 123 CAG AGT TTC AGG AGC TTC TCC TTT GAA AAG CCC CGG CAA CCC TCA CAG GCT GAC ACT GGC GGG GAC GAC TCG GAC GAG GAC TAT GAG AAG-3' |
| 34 | 5'-G CGA TCA CCC CCC GAT GGG 123 AGT TTC AGG AGC TTC TCC TTT GAA AAG CCC CGG CAA CCC TCA CAG GCT GAC ACT GGC GGG GAC GAC TCG GAC GAG GAC TAT GAG AAG-3' |
| 35 | 5'-G CGA TCA CCC CCC GAT GGG CAG 123 TTC AGG AGC TTC TCC TTT GAA AAG CCC CGG CAA CCC TCA CAG GCT GAC ACT GGC GGG GAC GAC TCG GAC GAG GAC TAT GAG AAG-3' |
| 36 | 5'-G CGA TCA CCC CCC GAT GGG CAG AGT 123 AGG AGC TTC TCC TTT GAA AAG CCC CGG CAA CCC TCA CAG GCT GAC ACT GGC GGG GAC GAC TCG GAC GAG GAC TAT GAG AAG-3' |
| 37 | 5'-G CGA TCA CCC CCC GAT GGG CAG AGT TTC 123 AGC TTC TCC TTT GAA AAG CCC CGG CAA CCC TCA CAG GCT GAC ACT GGC GGG GAC GAC TCG GAC GAG GAC TAT GAG AAG-3' |
| 38 | 5'-G CGA TCA CCC CCC GAT GGG CAG AGT TTC AGG 123 TTC TCC TTT GAA AAG CCC CGG CAA CCC TCA CAG GCT GAC ACT GGC GGG GAC GAC TCG GAC GAG GAC TAT GAG AAG-3' |
| 39 | 5'-G CGA TCA CCC CCC GAT GGG CAG AGT TTC AGG AGC 123 TCC TTT GAA AAG CCC CGG CAA CCC TCA CAG GCT GAC ACT GGC GGG GAC GAC TCG GAC GAG GAC TAT GAG AAG-3' |
| 40 | 5'-G CGA TCA CCC CCC GAT GGG CAG AGT TTC AGG AGC TTC 123 TTT GAA AAG CCC CGG CAA CCC TCA CAG GCT GAC ACT GGC GGG GAC GAC TCG GAC GAG GAC TAT GAG AAG-3' |
| 41 | 5'-G CGA TCA CCC CCC GAT GGG CAG AGT TTC AGG AGC TTC TCC 123 GAA AAG CCC CGG CAA CCC TCA CAG GCT GAC ACT GGC GGG GAC GAC TCG GAC GAG GAC TAT GAG AAG-3' |
| 42 | 5'-G CGA TCA CCC CCC GAT GGG CAG AGT TTC AGG AGC TTC TCC TTT 123 AAG CCC CGG CAA CCC TCA CAG GCT GAC ACT GGC GGG GAC GAC TCG GAC GAG GAC TAT GAG AAG-3' |
| 43 | 5'-G CGA TCA CCC CCC GAT GGG CAG AGT TTC AGG AGC TTC TCC TTT GAA 123 CCC CGG CAA CCC TGA CAG GCT GAC GAC GGG GAC G0AC TCG GAC GAG GAC TAT GAG AAG-3' |
| 44 | 5'-G CGA TCA CCC CCC GAT GGG CAG AGT TTC AGG AGC TTC TCC TTT GAA AAG 123 CGG CAA CCC TCA CAG GCT GAC ACT GGC GGG GAC GAC TCG GAC GAG GAC TAT GAG AAG-3' |
| 45 | 5'-G CGA TCA CCC CCC GAT GGG CAG AGT TTC AGG AGC TTC TCC TTT GAA AAG CCC 123 CAA CCC TCA CAG GCT GAC ACT GGC GGG GAC GAC TCG GAC GAG GAC TAT GAG AAG-3' |
| 46 | 5'-G CCA TCA CCC CCC GAT GGG CAG AGT TTC AGG AGC TTC TCC TTT GAA AAG CCC CGG 123 CCC TCA CAG GCT GAC ACT GGC GGG GAC GAC TCG GAC GAG GAC TAT GAG AAG-3' |
| 47 | 5'-G CGA TCA CCC CCC GAT GGG CAG AGT TTC AGG AGC TTC TCC TTT GAA AAG CCC CGG CAA 123 TCA CAG GCT GAC ACT GGC GGG GAC GAC TCG GAC GAG GAC TAT GAG AAG-3' |
| 48 | 5'-G CGA TCA CCC CCC GAT GGG CAG AGT TTC AGG AGC TTC TCC TTT GAA AAG CCC CGG CAA CCC 123 CAG GCT GAC ACT GGC GGG GAC GAC TCG GAC GAG GAC TAT GAG AAC-3' |
| 49 | 5'-G CGA TCA CCC CCC GAT GGG CAG AGT TTC AGG AGC TTC TCC TTT GAA AAG CCC CGG CAA CCC TCA 123 GCT GAC ACT GGC GGG GAC GAC TCG GAC GAG GAC TAT GAG AAC-3' |
| 50 | 5'-C CGA TCA CCC CCC GAT GGG CAG AGT TTC AGG AGC TTC TCC TTT GAA AAG CCC CGG CAA CCC TCA CAG 123 GAC ACT GGC GGG GAC GAC TCG GAC GAG GAC TAT GAG AAG-3' |
| 51 | 5'-G CGA TCA CCC CCC GAT GGG CAG AGT TTC AGG AGC TTC TCC TTT GAA AAG CCC CGG CAA CCC TCA CAG GCT 123 ACT GGC GGG GAC GAC TCG GAC GAG GAC TAT GAG AAC-3' |
| 52 | 5'-C CGA TCA CCC CCC GAT GGG CAG AGT TTC AGG AGC TTC TCC TTT GAA AAG CCC CGG CAA CCC TCA CAG GCT GAC 123 GGC GGG GAC GAC TCG GAC GAG GAC TAT GAG AAG-3' |
| 53 | 5'-G CGA TCA CCC CCC GAT GGG CAG AGT TTC AGG AGC TTC TCC TTT GAA AAG CCC CGG CAA CCC TCA CAG GCT GAC ACT 123 GGG GAC GAC TCG GAC GAG GAC TAT GAG AAG-3' |
| 54 | 5'-G CGA TCA CCC CCC GAT GGG CAG AGT TTC AGG AGC TTC TCC TTT GAA AAG CCC CGG CAA CCC TCA CAG GCT GAC ACT GGC 123 GAC GAC TCG GAC GAG GAC TAT GAG AAG-3' |
| 55 | 5'-C CGA TCA CCC CCC GAT GGG CAG AGT TTC AGG AGC TTC TCC TTT GAA AAG CCC CGG CAA CCC TCA CAG GCT GAC ACT GGC GGG 123 GAC TCG GAC GAG GAC TAT GAG AAG-3' |
| 56 | 5'-G CGA TCA CCC CCC GAT GGG CAG AGT TTC AGG |

TABLE 3-continued

MUTANT SH3BP2 EXON 9 NUCLEOTIDE SEQUENCES

| SEQ ID NO. | SEQUENCE |
|---|---|
| | AGC TTC TCC TTT GAA AAG CCC CGG CAA CCC TCA CAG GCT GAC ACT GGC GGG GAC 123 TCG GAC GAG GAC TAT GAG AAG-3' |
| 57 | 5'-G CGA TGA CCC CCC GAT GGG CAG AGT TTC AGG AGC TTC TCC TTT GAA AAG CCC CGG CAA CCC TCA CAG GCT GAC ACT GGC GGG GAC 123 GAC GAG GAC TAT GAG AAG-3' |
| 58 | 5'-G CGA TCA CCC CCC GAT GGG CAG AGT TTC AGG AGC TTC TCC TTT GAA AAG CCC CGG CAA CCC TCA CAG GCT GAC ACT GGC GGG GAC GAC TCG 123 GAG GAC TAT GAG AAG-3' |
| 59 | 5'-G CGA TCA CCC CCC GAT GGG CAG AGT TTC AGG AGC TTC TCC TTT GAA AAG CCC CGG CAA CCC TCA CAG GCT GAC ACT GGC GGG GAC GAC TCG GAC 123 GAC TAT GAG AAG-3' |
| 60 | 5'-G CGA TCA CCC CCC GAT GGG CAG AGT TTC AGG AGC TTC TCC TTT GAA AAG CCC CGG CAA CCC TCA CAG GCT GAC ACT GGC GGG GAC GAC TCG GAC GAG 123 TAT GAG AAG-3' |
| 61 | 5'-G CGA TCA CCC CCC GAT GGG CAG AGT TTC AGG AGC TTC TCC TTT GAA AAG CCC CGG CAA CCC TGA CAG GCT GAC ACT GGC GGG GAC GAC TCG GAC GAG GAC 123 GAG AAG-3' |
| 62 | 5'-G CGA TCA CCC CCC GAT GGG CAG AGT TTC AGG AGC TTC TCC TTT GAA AAG CCC CGG CAA CCC TCA CAG GCT GAC ACT GGC GGG GAC GAC TCG GAC GAG GAC TAT 123 AAG-3' |
| 63 | 5'-G CGA TCA CCC CCC GAT GGG CAG AGT TTC AGG AGC TTC TCC TTT GAA AAG CCC CGG CAA CCC TCA CAG GCT GAC ACT GGC GGG GAC GAC TCG GAC GAG GAC TAT GAG 123-3' |

KEY: "123" refers to a coding triplet such that 1, 2, and 3 are independently selected from the group consisting of C, G, A, and T provided that the coding triplet does not encode the same amino acid as that located at the corresponding amino acid position in the wild type SH3BP2 exon 9 polypeptide (SEQ ID NO:102), and provided that encoded polypeptide has a mutant SH3BP2 functional activity.

TABLE 4

MUTANT SH3BP2 EXON 9 AMINO ACID SEQUENCES

| SEQ ID NO. | SEQUENCE |
|---|---|
| 64 | 4 S P 5 D 6 Q S F R S F S F E K P R Q P S Q A D T G G D D S D E D Y E K |
| 65 | 4 S P P D G Q S F R S F S F E K P R Q P S Q A D T G G D D S D E D Y E K |
| 66 | R 4 P P D G Q S F R S F S F E K P R Q P S Q A D T G G D D S D E D Y E K |
| 67 | R S 4 P D G Q S F R S F S F E K P R Q P S Q A D T G G D D S D E D Y E K |
| 68 | R S P 4 D G Q S F R S F S F E K P R Q P S Q A D T G G D D S D E D Y E K |
| 69 | R S P P 4 G Q S F R S F S F E K P R Q P S Q A D T G G D D S D E D Y E K |
| 70 | R S P P D 4 Q S F R S F S F E K P R Q P S Q A D T G G D D S D E D Y E K |
| 71 | R S P P D G 4 S F R S F S F E K P R Q P S Q A D T G G D D S D E D Y E K |
| 72 | R S P P D G Q 4 F R S F S F E K P R Q P S Q A D T G G D D S D E D Y E K |
| 73 | R S P P D G Q S 4 R S F S F E K P R Q P S Q A D T G G D D S D E D Y E K |
| 74 | R S P P D G Q S F 4 S F S F E K P R Q P S Q A D T G G D D S D E D Y E K |
| 75 | R S P P D G Q S F R 4 F S F E K P R Q P S Q A D T G G D D S D E D Y E K |
| 76 | R S P P D G Q S F R S 4 S F E K P R Q P S Q A D T G G D D S D E D Y E K |
| 77 | R S P P D G Q S F R S F 4 F E K P R Q P S Q A D T G G D D S D E D Y E K |
| 78 | R S P P D G Q S F R S F S 4 E K P R Q P S Q A D T G G D D S D E D Y E K |
| 79 | R S P P D G Q S F R S F S F 4 K P R Q P S Q A D T G G D D S D E D Y E K |
| 80 | R S P P D G Q S F R S F S F E 4 P R Q P S Q A D T G G D D S D E D Y E K |
| 81 | R S P P D G Q S F R S F S F E K 4 R Q P S Q A D T G G D D S D E D Y E K |
| 82 | R S P P D G Q S F R S F S F E K P 4 Q P S Q A D T G G D D S D E D Y E K |

TABLE 4-continued

MUTANT SH3BP2 EXON 9 AMINO ACID SEQUENCES

| SEQ ID NO. | SEQUENCE |
|---|---|
| 83 | R S P P D G Q S F R S F S F E K P R 4 P S Q A D T G G D D S D E D Y E K |
| 84 | R S P P D G Q S F R S F S F E K P R Q 4 S Q A D T G G D D S D E D Y E K |
| 85 | R S P P D G Q S F R S F S F E K P R Q P 4 Q A D T G G D D S D E D Y E K |
| 86 | R S P P D G Q S F R S F S F E K P R Q P S 4 A D T G G D D S D E D Y E K |
| 87 | R S P P D G Q S F R S F S F E K P R Q P S Q 4 D T G G D D S D E D Y E K |
| 88 | R S P P D G Q S F R S F S F E K P R Q P S Q A 4 T G G D D S D E D Y E K |
| 89 | R S P P D G Q S F R S F S F E K P R Q P S Q A D 4 G G D D S D E D Y E K |
| 90 | R S P P D G Q S F R S F S F E K P R Q P S Q A D T 4 G D D S D E D Y E K |
| 91 | R S P P D G Q S F R S F S F E K P R Q P S Q A D T G 4 D D S D E D Y E K |
| 92 | R S P P D G Q S F R S F S F E K P R Q P S Q A D T G G 4 D S D E D Y E K |
| 93 | R S P P D G Q S F R S F S F E K P R Q P S Q A D T G G D 4 S D E D Y E K |
| 94 | R S P P D G Q S F R S F S F E K P R Q P S Q A D T G G D D 4 D E D Y E K |
| 95 | R S P P D G Q S F R S F S F E K P R Q P S Q A D T G G D D S 4 E D Y E K |
| 96 | R S P P D G Q S F R S F S F E K P R Q P S Q A D T G G D D S D 4 D Y E K |
| 97 | R S P P D G Q S F R S F S F E K P R Q P S Q A D T G G D D S D E 4 Y E K |
| 98 | R S P P D G Q S F R S F S F E K P R Q P S Q A D T G G D D S D E D 4 E K |
| 99 | R S P P D G Q S F R S F S F E K P R Q P S Q A D T G G D D S D E D Y 4 K |
| 100 | R S P P D G Q S F R S F S F E K P R Q P S Q A D T G G D D S D E D Y E 4 |

KEY: "4," "5," and "6"" each refers to an amino acid, such that each 4, 5, and 6 is independently selected, provided that at least one 4, 5, 6 in each sequence is selected such that amino acid is not the same amino acid as that located at the corresponding amino acid position in the wild type SH3BP2 exon 9 polypeptide (SEQ ID:102), and provided that the encoded polypeptide has a mutant SH3BP2 functional activity.

TABLE 5

SH3BPS EXONS IN GENBANK Z68279

| | 3'-5' |
|---|---|
| EXON1 | 20503~20707 |
| EXON2 | 18142~18281 |
| EXON3 | 15858~15960 |
| EXON4 | 14163~14280 |
| EXON5 | 13697~13767 |
| EXON6 | 11602~11690 |
| EXON7 | 11246~11314 |
| EXON8 | 8774~9427 |
| EXON9 | 7242~7350 |
| EXON10 | 6943~6998 |
| EXON11 | 6509~6590 |
| EXON12 | 5872~5931 |
| EXON13 | 4631~5224 |

TABLE 6

SH3BP2 EXON 9 NUCLEOTIDE AND AMINO ACID SEQUENCE

```
5'-G CGA TCA CCC CCC GAT GGG CAG AGT TTC AGG
     R   S   P   P   D   G   Q   S   F   R

AGC TTC TCC TTT GAA AAG CCC CGG CAA CCC TCA
    S   F   S   F   E   K   P   R   Q   P   S

CAG GCT GAC ACT GGC GGG GAC GAC TCG GAC GAG
    Q   A   D   T   G   G   D   D   S   D   E

GAC TAT GAG AAG-3'
    D   Y   E   K
```

The presence of the mutant domain in the SH2BP2 sequence, identifies the mutant SH3BP2 nucleic acid molecule as a unique nucleic acid molecule derived as a point mutation(s) of the wild type SH3BP2 gene. The number of nucleotides contributed by the wild type SH3BP2 source gene on either side of the point mutation may differ and may be 1, 2, 3, 4 or more nucleotides, provided the mutant domain containing the point mutation is capable of uniquely identifying a mutant SH3BP2 nucleic acid molecule.

Homologs and alleles of the mutant SH3BP2 nucleic acid molecules of the invention can be identified by conventional techniques. Thus, an aspect of the invention is those nucleotide sequences which code for mutant SH3BP2 polypeptides and which hybridize under stringent conditions to a nucleic acid molecule comprising a nucleotide sequence selected from the group consisting of SEQ ID NO:5 (generic mutant—full length); SEQ ID NO:7 (generic mutant domain); SEQ ID NO:9 ("H" family mutation), SEQ ID NO:11 ("K" family mutation), SEQ ID NO:13 ("A,B" family mutation), SEQ ID NO:15 ("C,F,J,M,O" family mutation), SEQ ID NO:17 ("L" family mutation), SEQ ID NO: 19 ("G" family mutation), and SEQ ID NO:21 ("N" family mutation), SEQ ID NO:26 (genomic mutant SH3BP2), SEQ ID NOs:27-63 (mutant SH3BP2 exon 9) and a genomic mutant SH3BP2 nucleic acid molecule having a sequence identical to SEQ ID NO:25 with the exception that a mutant exon 9 selected from the group consisting of SEQ ID NOs: 27-63 is used in place of the wild type exon 9, and which do not code for a wild type SH3BP2, such as that encoded by SEQ ID NO:1 (human "WT" SH3BP2 full length sequence). The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrolidone, 0.02% bovine serum albumin, 2.5 mM $NaH_2PO_4$, pH 7, 0.5% SDS, 2 mM EDTA). SSC is 0.15M sodium chloride/0.15M sodium citrate, pH 7; SDS is sodium dodecyl sulphate; and EDTA is ethylenediaminetetraacetic acid. After hybridization, the membrane upon which the DNA is transferred is washed at 2×SSC at room temperature and then at 0.1×SSC/0.1% SDS at temperatures up to 68° C.

There are other conditions, reagents, and so forth which can be used, and would result in a similar degree of stringency. The skilled artisan will be familiar with such conditions, and thus they are not given here. It will be understood, however, that the skilled artisan will be able to manipulate the conditions in a manner to permit the clear identification of homologs and alleles of the mutant SH3BP2 nucleic acid molecules of the invention. The skilled artisan also is familiar with the methodology for screening cells and libraries for expression of such molecules which then are routinely isolated, followed by isolation of the pertinent nucleic acid molecule and sequencing.

In general, homologs and alleles typically will share at least 75% nucleotide identity to SEQ ID NO:5 (generic mutant—full length nucleic acid) and will include a sequence that shares at least 95% and, preferably, at least 96%, 97%, 98%, or 99% nucleotide sequence identity to a sequence selected from the group consisting of SEQ ID NO:7 (generic mutant domain); SEQ ID NO:9 ("H" family mutation), SEQ ID NO:11 ("K" family mutation), SEQ ID NO:13 ("A,B" family mutation), SEQ ID NO:15 ("C,F,J,M,O" family mutation), SEQ ID NO:17 ("L" family mutation), SEQ ID NO: 19 ("G" family mutation), and SEQ ID NO:21 ("N" family mutation). Similarly, the homologs and alleles typically will share at least 75% amino acid sequence identity to SEQ ID NO:6 (generic mutant—full length polypeptide) and will include a sequence that shares at least 85% and, preferably, at least 86% through 99% (and every integer therebetween) amino acid sequence identity with a sequence selected from the group consisting of SEQ ID NO:8, SEQ ID NO:10, SEQ ID NO: 12, SEQ ID NO:14, SEQ ID NO:16, SEQ. ID NO:18, SEQ ID NO:20 and SEQ ID NO:22. In some instances sequences will share at least 95% nucleotide identity and/or at least 90% amino acid identity and in still other instances sequences will share at least 95% nuclcotide identity and/or at least 95% or 99% amino acid identity. In certain embodiments, the homologs and alleles include an exon 9 encoded amino acid sequence that will share at least 98% and, preferably, at least 99% amino acid sequence identity with a sequence selected from the group consisting of SEQ ID Nos: 64-100. Likewise, in certain embodiments, the homologs and alleles include an exon 9 nucleotide sequence that will share at least 85% and, more preferably, at least 90%- 95% nucleotide sequence identity with a sequence selected from the group consisting of SEQ ID Nos:27-63.

The homology can be calculated using various, publicly available software tools developed by NCBI (Bethesda, Md.) that can be obtained through the internet at the NCBI/NIG website. Exemplary tools include the BLAST system available on the internet at the NCBI/NIH website. Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acid molecules also are embraced by the invention.

In screening for mutant SH3BP2 related genes, such as homologs and alleles, a Southern blot may be performed using the foregoing conditions, together with a radioactive probe. After washing the membrane to which the DNA is finally transferred, the membrane can be placed against X-ray film or a phosphoimager plate to detect the radioactive signal.

The invention also includes degenerate nucleic acid molecules which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into, for example, an elongating mutant SH3BP2 polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acid molecules that differ from the biologically isolated nucleic acid molecules in codon sequence due to the degeneracy of the genetic code.

The invention also provides isolated unique fragments of a mutant SH3BP2 nucleic acid molecule comprising a sequence selected from the group consisting of SEQ ID NO: 5 (generic mutant full length nucleic acid); SEQ ID NO:7 (generic mutant domain); SEQ ID NO:9 ("H" family mutation), SEQ ID NO:11 ("K" family mutation), SEQ ID NO:13 ("A,B" family mutation), SEQ ID NO:15 ("C,F,J,M,O" family mutation), SEQ ID NO:17 ("L" family mutation), SEQ ID NO: 19 ("G" family mutation), SEQ ID NO:21 ("N" family mutation), SEQ ID NO:26 (genomic mutant SH3BP2), SEQ ID NOs:27-63 (mutant SH3BP2 exon 9) and a genomic mutant SH3BP2 nucleic acid molecule having a sequence identical to SEQ ID NO: 25 with the exception that a mutant exon 9 selected from the group consisting of SEQ ID NOs: 27-63 is used in place of the wild type exon 9. A unique fragment is one that is a 'signature' for the larger nucleic acid. For example, the unique fragment is long enough to assure that its precise sequence is not found in molecules within the human genome outside of the mutant SH3BP2 nucleic acid molecules defined above (and human alleles). Those of ordinary skill in the art may apply no more than routine procedures to determine if a fragment is unique within the human genome. The preferred unique fragments contain the mutant SH3BP2 exon 9 (SEQ ID Nos:27-63). Exemplary unique fragments are represented by SEQ ID NO:7 (generic mutant domain); SEQ ID NO:9 ("H" family mutation), SEQ ID NO:11 ("K" family mutation), SEQ ID NO:13 ("A,B" family mutation), SEQ ID NO:15 ("C,F,J,M,O" family mutation), SEQ ID NO:17 ("L" family mutation), SEQ ID NO: 19 ("G" family mutation), SEQ ID NO:21 ("N" family mutation), SEQ ID NO:26 (genomic mutant SH3BP2), SEQ ID NOs: 27-63 (mutant SH3BP2 exon 9) and a genomic mutant SH3BP2 nucleic acid molecule having a sequence identical to SEQ ID NO:25 with the exception that a mutant exon 9 selected from the group consisting of SEQ ID NOs: 27-63 is used in place of the wild type exon 9 and smaller fragments of the foregoing nucleic acids which contain 4, 5, 6, 7, 8, 9, or 10 nucleotides, including the point mutation identified in each as distinctive of a mutant SH3BP2 mutant domain.

Thus, according to one aspect of the invention, an isolated mutant SH3BP2 unique nucleic acid fragment is provided which is selected from the group consisting of: (a) a unique fragment of a nucleic acid molecule having a sequence selected from the group consisting of SEQ ID NO:5 (generic mutant full length nucleic acid); SEQ ID NO:7 (generic mutant domain); SEQ ID NO:9 ("H" family mutation), SEQ ID NO:11 ("K" family mutation), SEQ ID NO:13 ("A,B" family mutation), SEQ ID NO:15 ("C,F,J,M,O" family mutation), SEQ ID NO:17 ("L" family mutation), SEQ ID NO: 19 ("G" family mutation), SEQ ID NO:21 ("N" family mutation SEQ ID NO:26 (genomic mutant SH3BP2), SEQ ID NOs: 27-63 (mutant SH3BP2 exon 9) and, a genomic mutant SH3BP2 nucleic acid molecule having a sequence identical to SEQ ID NO: 25 with the exception that a mutant exon 9 selected from the group consisting of SEQ ID NOs: 27-63 is used in place of the wild type exon 9 (of sufficient length to represent a sequence unique within the human genome); and (b) complements of (a). The unique fragments of the invention include a sequence of contiguous nucleotides which excludes previously published sequences as of the date of invention or the filing date of this application or a priority document, (2) complements of (1), and optionally, (3) unique fragments of (1) and (2).

In certain embodiments, the sequence of contiguous nucleotides is selected from the group consisting of (1) at least two contiguous nucleotides nonidentical to the sequence group (e.g., SEQ ID Nos: 1 or 25), (2) at least three contiguous nucleotides nonidentical to the sequence group, (3) at least four contiguous nucleotides nonidentical to the sequence group, (4) at least five contiguous nucleotides nonidentical to the sequence group, (5) at least six contiguous nucleotides nonidentical to the sequence group, (6) at least seven contiguous nucleotides nonidentical to the sequence group.

In other embodiments, the unique fragment has a size selected from the group consisting of at least: 6 nucleotides, 8 nucleotides, 10 nucleotides, 12 nucleotides, 14 nucleotides, 16 nucleotides, 18 nucleotides, 20, nucleotides, 22 nucleotides, 24 nucleotides, 26 nucleotides, 28 nucleotides, 30 nucleotides, 40 nucleotides, 50 nucleotides, 75 nucleotides, 100 nucleotides, 200 nucleotides, the number of nucleotides comprising the SH3BP2 gene, and every integer length therebetween.

Unique fragments of mutant SH3BP2 nucleic acid molecules, however, exclude fragments completely composed of sequences of a wild type SH3BP2 nucleic acid (SEQ ID NO:1), wild type SH3BP2 fragment (SEQ ID NO:3), or wild type genomic SH3BP2 (SEQ ID NO:25) which do not contain a mutant domain.

Unique fragments can be used as probes in Southern and Northern blot assays to identify such nucleic acid molecules, or can be used in amplification assays such as those employing PCR. As known to those skilled in the art, large probes such as 200, 250, 300 or more nucleotides are preferred for certain uses such as Southern and Northern blots, while smaller fragments will be preferred for use as PCR primers. Unique fragments also can be used to generate antibodies or to determine binding of a polypeptide fragment, or to generate immunoassay components. Likewise, unique fragments can be employed to produce nonfused fragments of the mutant SH3BP2, again useful, for example, in the preparation of antibodies, immunoassays or therapeutic applications. Unique fragments can be further used as antisense molecules to inhibit the expression of mutant SH3BP2 nucleic acid molecules and polypeptides, respectively.

As will be recognized by those skilled in the art, the size of the unique fragment will depend upon its conservancy in the genetic code. Thus, some regions of SEQ ID NO:5 (generic mutant full length nucleic acid); SEQ ID NO:7 (generic mutant domain); SEQ ID NO:9 ("H" family mutation), SEQ ID NO:11 ("K" family mutation), SEQ ID NO:13 ("A,B" family mutation), SEQ ID NO:15 ("C,F,J,M,O" family mutation), SEQ ID NO:17 ("L" family mutation), SEQ ID NO: 19 ("G" family mutation), SEQ ID NO:21 ("N" family mutation), SEQ ID NO:26 (genomic mutant SH3BP2), SEQ ID NOs:27-63 (mutant SH3BP2 exon 9) and a genomic mutant SH3BP2 nucleic acid molecule having a sequence identical to SEQ ID NO: 25 with the exception that a mutant exon 9 selected from the group consisting of SEQ ID NOs: 27-63 is used in place of the wild type exon 9, and complements thereof will require longer segments to be unique while others will require only short segments, typically between 6 and 32 nucleotides long (e.g. 6, 7, 8, 9, 10, 11, 12, 13, 14, 15, 16, 17, 18, 19, 20, 21, 22, 23, 24, 25, 26, 27, 28, 29, 30, 31 and 32 bases) or more, up to the entire length of the disclosed sequences. This disclosure intends to embrace each and every fragment of each mutant SH3BP2 nucleic acid molecule, including unique cDNA, mRNA, and genomic sequences. Those skilled in the art are well versed in methods for selecting such sequences, typically on the basis of the ability of the unique fragment to selectively distinguish the sequence of interest from other sequences in the human genome of the fragment to those on known databases typically is all that is necessary, although in vitro confirmatory hybridization and sequencing analysis may be performed.

According to yet another aspect of the invention, expression vectors containing the isolated nucleic acid molecules of the invention, operably linked to a promoter, as well as host cells transformed or transfected with such expression vectors, are provided. In certain preferred embodiments, the host cells are eukaryotic cells. As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frameshift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Insertion of any of the nucleotide sequences described herein into an appropriate vector allows production of large quantities of such sequences. Indeed, vectors, methods for inserting nucleic acid-molecules into vectors, and use of such vectors for production of desired nucleic acid molecules, peptides and proteins are well known to those with skill in the art. Thus, the nucleotide sequences disclosed herein can also be inserted into cloning and/or expression vectors to produce peptides and proteins according to the present invention.

Procedures and materials for preparation of replicable vectors, transformation of host cells with vectors, and host cell expression of polypeptides are described in Maniatis et al., *Molecular Cloning: A Laboratory Manual*, Cold Spring Harbor (1982) incorporated herein by reference. A replicable vector as used herein is a vector capable of being replicated and is thus useful for producing large quantities of a nucleic acid molecule of choice. Any replicable vector known to those with skill in the art may be used to clone or amplify mutant SH3BP2 nucleic acid molecules and/or to produce polypeptides encoded thereby. For example, suitable vectors include plasmids, phages, cosmids and artificial chromosomes. For example, bacteriophage lambda may be a useful cloning vector. This phage can accept pieces of foreign DNA up to about 20,000 base pairs in length. The lambda phage genome is a linear double stranded DNA molecule with single stranded complementary (cohesive) ends which can hybridize with each other when inside an infected host cell. The lambda DNA is cut with a restriction endonuclease and the foreign DNA, e.g., the DNA to be cloned, is ligated to the phage DNA fragments. The resulting recombinant molecule is then packaged into infective phage particles. Host cells are infected with the phage particles containing the recombinant DNA. The phage DNA replicates in the host cell to produce many copies of the desired DNA sequence.

Cosmids are hybrid plasmid/bacteriophage vectors which can be used to clone DNA fragments of about 40,000 base pairs. Cosmids have one or more DNA sequences called "cos" sites derived from bacteriophage lambda for packaging lambda DNA into infective phage particles. Two cosmids are ligated to the DNA to be cloned. The resulting molecule is packaged into infective lambda phage particles and transfected into bacteria host cells. When the cosmids are inside the host cell they behave like plasmids and multiply under the control of a plasmid origin of replication. The origin of replication is a sequence of DNA which allows a plasmid to multiply within a host cell.

Yeast artificial chromosome vectors (YAC) are similar to plasmids but allow for the incorporation of much larger DNA sequences of about 300 kb (kilobases) to 2 Mb (megabases), with an average of approximately 700 kb. The yeast artificial chromosomes contain sequences for replication in yeast. The yeast artificial chromosome containing the DNA to be cloned is transformed into yeast cells where it replicates thereby producing many copies of the desired DNA sequence. Where phage, cosmids or yeast artificial chromosomes are employed as cloning vectors, expression of the mutant SH3BP2 polypeptide may be obtained by culturing host cells that have been transfected or transformed with the cloning vector in a suitable culture medium. The bacterial artificial chromosomes used herein allow for the incorporation of 50-300 kb of DNA sequences.

Suitable host/vector systems are available for propagation of nucleotide sequences and the expression of peptides and proteins. Replicable plasmids, viral vectors, and host cells such as CHO, COS, insect, yeast and bacterial are well-known for use in genetic engineering and can be used herein.

As used herein with respect to nucleic acid molecules, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleotide sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein with respect to polypeptides (discussed below), the term "isolated" means separated from its native environment in sufficiently pure form so that it can be manipulated or used for any one of the purposes of the invention. Thus, isolated means sufficiently pure to be used (i) to raise and/or isolate antibodies, (ii) as a reagent in an assay, or (iii) for sequencing, etc.

According to yet another aspect of the invention, antisense oligonucleotides that selectively bind to a nucleic acid molecule encoding a mutant SH3BP2 polypeptide are provided. The antisense oligonucleotides are useful for decreasing mutant SH3BP2 expression (at a transcriptional and translational level) and functional activity.

As used herein, the term "antisense oligonucleotide" or "anti sense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Antisense oligonucleotides that selectively bind to mutant SH3BP2 nucleic acid molecules are particularly preferred. Those skilled in the art will recognize that the exact length of the antisense oligonucleotide and its degree of complementarity with its target will depend upon the specific target selected, including the sequence of the target and the particular bases which comprise that sequence.

It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:5 (generic mutant full length nucleic acid); SEQ. ID NO:7 (generic mutant domain); SEQ ID NO:9 ("H" family mutation), SEQ ID NO:11 ("K" family mutation), SEQ ID NO:13 ("A,B" family mutation), SEQ ID NO:15 ("C,F,J,M,O" family mutation), SEQ ID NO:17 ("L" family mutation), SEQ ID NO: 19 ("G" family mutation), SEQ ID NO:21 ("N" family mutation), SEQ ID NO:26 (genomic mutant SH3BP2), SEQ ID NOs:27-63 (mutant SH3BP2 exon 9) and a genomic mutant SH3BP2 nucleic acid molecule having a sequence identical to SEQ ID NO: 25 with the exception that a mutant exon 9 selected from the group consisting of SEQ ID NOs: 27-63 is used in place of the wild type exon 9, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least about 10 and, more preferably, at least about 15 consecutive bases which are complementary to the target, although in certain cases modified oligonucleotides as short as 7 bases in length have been used successfully as antisense oligonucleotides. See Wagner et al., *Nat. Med.* 1(11): 1116-1118, 1995. Most preferably, the antisense oligonucleotides comprise a complementary sequence of 20-30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439-457, 1994) and at which proteins are not expected to bind.

Finally, although SEQ ID NO:5 (generic mutant full length nucleic acid); SEQ ID NO:7 (generic mutant domain); SEQ ID NO:9 ("H" family mutation), SEQ ID NO:11 ("K" family mutation), SEQ ID NO:13 ("A,B" family mutation), SEQ ID NO:15 ("C,F,J,M,O" family mutation), SEQ ID NO:17 ("L" family mutation), SEQ ID NO: 19 ("G" family mutation), SEQ ID NO:21 ("N" family mutation), and SEQ ID Nos:27-63, disclose cDNA sequences, one of ordinary skill in the art may easily derive the genomic DNA corresponding to each sequence. Thus, the present invention also provides for antisense oligonucleotides which are complementary to the genomic DNA corresponding to SEQ ID NO: 5 (generic mutant full length nucleic acid); SEQ ID NO:7 (generic mutant domain); SEQ ID NO:9 ("H" family mutation), SEQ ID NO:11 ("K" family mutation), SEQ ID NO:13 ("A,B" family mutation), SEQ ID NO:15 ("C,F,J,M,O" family mutation), SEQ ID NO:17 ("L" family mutation), SEQ ID NO: 19 ("G" family mutation), SEQ ID NO:21 ("N" family mutation), and SEQ ID Nos:27-63. Similarly, antisense to allelic or homologous mutant SH13BP2 and genomic DNAs are enabled without undue experimentation.

In another aspect, ribozymes, which are catalytic RNA sequences that cleave specific RNA molecules, are used to disrupt translation of mutant SH3BP2 nucleic acid molecules. Several studies have demonstrated that ribozymes can be employed to inhibit oncogene expression, cell growth or induce apoptosis in tumor cell lines. U.S. Pat. No. 5,635,385 to Leopold, et al., incorporated herein by reference, describes a therapeutic method for the treatment of a leukemia patient resulting from a chromosomal translocation (BCR/ABL) using a ribozyme that cleaves the oncogene mRNA and inhibits the expression of the polypeptide. A similar approach is employed according to the present invention using a synthetic ribozyme targeted to the mutant SH3BP2 mRNA molecules.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides or ribozymes of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acid molecules has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides. The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose.

Thus, according to yet another aspect of the invention, a method of reducing expression of an SH3BP2 mutant nucleic acid molecule in a cell or cell-free system containing a SH3BP2 mutant nucleic acid molecule, is provided. The method may be practiced in vivo or in vitro. In general, the method involves introducing a SH3BP2 mutant antisense nucleic acid molecule or ribozyme that binds to and selectively cleaves a mutant SH3BP2 mRNA into the system (e.g., a cell), and allowing the SH3BP2 mutant antisense or ribozyme molecule to hybridize (and, if a ribozyme, cleave) to a sense SH3BP2 mutant nucleic acid molecule, thereby inhibiting expression of the sense SH3BP2 mutant nucleic acid molecule.

The present invention also contemplates pharmaceutical preparations containing modified antisense molecules that are complementary to and hybridizable with, under physiological conditions, nucleic acid molecules encoding mutant SH3BP2 polypeptides, together with pharmaceutically acceptable carriers. Antisense oligonucleotides may be administered as part of a pharmaceutical composition. In this latter embodiment, it is preferable that localized or intravenous administration be used. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art. Pharmaceutically acceptable carriers are discussed in more detail below in reference to the therapeutic methods of the invention.

According to yet another aspect of the invention, transgenic non-human animals having somatic and germ line cells that contain any of the isolated SH3BP2 mutant nucleic acid molecules of the invention also are provided. Preferably, the expression of the SH3BP2 mutant nucleic acid molecule results in the animal having a bone homeostasis disorder. Such animals are useful as models of human bone homeostasis disorders and for studying transformation effects of mutant SH3BP2 nucleic acid molecules and polypeptides. Methods of creating transgenic animals are well known in the art. For example, U.S. Pat. No. 4,873,191, incorporated herein by reference, describes genetic transformation of zygotes. Following such procedures, the mutant SH3BP2 nucleic acid molecule is microinjected into the nucleus of a zygote which is then allowed to undergo differentiation and development into a mature organism. Transgenic animals such as mice or pigs will have somatic and germ line cells containing the mutant SH3BP2 nucleic acid molecule. Such animals are useful as in vivo models for certain malignant syndromes and allow for the further development and testing of treatment modalities and screening assays for the identification of therapeutic agents. Other uses will be apparent to one of ordinary skill in the art.

As used herein, "transgenic non-human animals" include non-human animals having one or more exogenous nucleic acid molecules incorporated in germ line cells and/or somatic cells. Thus transgenic animals include "knockout" and "knockin" animals having a homozygous or heterozygous gene disruption by homologous recombination, animals having episomal or chromosomally incorporated expression vectors, etc. Knockout and knockin animals can be prepared by homologous recombination using embryonic stem cells as is well known in the art. The recombination may be facilitated using, for example, the cre/lox system or other recombinase systems known to one of ordinary skill in the art. In certain embodiments, the recombinase system itself is expressed conditionally, for example, in certain tissues or cell types, at certain embryonic or post-embryonic developmental stages, inducibly by the addition of a compound which increases or decreases expression, and the like. In general, the conditional expression vectors used in such systems use a variety of promoters which confer the desired gene expression pattern (e.g., temporal or spatial). Conditional promoters also can be operably linked to, for example, mutant SH3BP2 nucleic acid molecules to increase expression of mutant SH3BP2 in a regulated or conditional manner. Trans-acting negative regulators of, for example, mutant SH3BP2 activity or expression also can be operably linked to a conditional promoter as described above. Such trans-acting regulators include antisense mutant SH3BP2 nucleic acid molecules, and the like.

According to yet another aspect of the invention, primers for amplifying the above-identified nucleic acid sequences, including antisense sequences, are provided. In this aspect, the preferred isolated nucleic acid molecules are selected from the group consisting of a nucleic acid molecule having a sequence selected from the group consisting of SEQ ID NO:23, 24 and other sequences which are capable of hybridizing to a mutant SH3BP2 nucleic acid molecule and, thereby useful in amplifying exon 9 in a mutant SH3BP2 nucleic acid molecule, and complements of the foregoing nucleic acids.

The primers of the invention are useful for performing nucleic acid amplification techniques, such as PCR, and may be used to increase (i.e., amplify) mutant SH3BP2 nucleic acid molecules (either DNA or RNA in nature) or a fragment of such molecules. In some instances, the extent of amplification will depend upon the number of preexisting copies contained in the sample prior to manipulation. Preferably, the mutant SH3BP2 nucleic acid molecules encode all or portions of the mutant SH3BP2 polypeptide. The end result of such a PCR reaction may be a detectable amount of the amplified mutant SH3BP2 product, usually in the form of a nucleic acid molecule of a given length. In a variation of this approach, the PCR product (i.e., the amplified band) is visualized through hybridization with a labeled probe, as described earlier for Southern analysis. PCR techniques are well-known and described, for example, in Alberts et al., *Molecular Biology of the Cell*, 2nd ed., pp. 269-276 (1989), incorporated herein by reference. Briefly, PCR is performed by heating the sample to separate complementary nucleic acid strands which are then annealed to complementary primer oligonucleotides which serve as primers for DNA synthesis catalyzed by polymerase enzymes between the primers. Multiple cycles of PCR provide multiple copies of the target sequence as long as the target sequence was originally present in the sample.

Thus, the present invention provides a method for amplifying and detecting the presence of mutant SH3BP2 nucleic acid molecules in a sample by contacting the sample with at least two nucleic acid amplification primers, amplifying a primed nucleic acid molecule which hybridizes to the first and the second nucleic acid amplification primers; and detecting the presence of an amplified nucleic acid molecule in the sample. The first nucleic acid amplification primer and a second nucleic acid amplification primers are capable of hybridizing to a SH3BP2 mutant nucleic acid molecule and amplifying a nucleic acid comprising a sequence selected from the group consisting of SEQ ID NO:5 (generic mutant—full length); SEQ ID NO:7 (generic mutant domain); SEQ ID NO:9 ("H" family mutation), SEQ ID NO:11 ("K" family mutation), SEQ ID NO:13 ("A,B" family mutation), SEQ ID NO:15 ("C,F,J,M,O" family mutation), SEQ ID NO:17 ("L" family mutation), SEQ ID NO: 19 ("G" family mutation), SEQ ID NO:21 ("N" family mutation), SEQ ID NO:26 (genomic mutant SH3BP2), SEQ ID NOs:27-63 (mutant SH3BP2 exon 9) and a genomic mutant SH3BP2 nucleic acid molecule having a sequence identical to SEQ ID NO: 25 with the exception that a mutant exon 9 selected from the group consisting of SEQ ID NOs: 27-63 is used in place of the wild type exon 9 and, preferably, are not capable of hybridizing to and amplifying SEQ ID NO:1 (human "WT" SH3BP2 full length sequence), SEQ ID NO:3 (human WT domain), SEQ ID NO:15 (genomic WT SH3BP2), or SEQ ID NO:101 (human WT exon 9). Exemplary primers include SEQ ID Nos: 23 and 24.

In theory, any combination of nucleic acid molecules each greater than approximately 10-20 base pairs in length which flank the point mutation(s) disclosed herein can serve as primers for PCR. The primers may be either DNA or RNA in nature although, usually DNA primers are preferred due to an increased stability. If the nucleic acid molecule to which the primers hybridize is RNA in nature, a first step of reverse transcription (RT) of the RNA molecule is required and the procedure is referred to as RT-PCR. RT-PCR methods are well known in the art. It should be understood that amplification primers may be derived from any region of the mutant SH3BP2 nucleic acid sequence which flank the point mutation(s), including intronic portions of genomic DNA. The target sequence for amplification can include genomic DNA or mRNA which encode all or unique fragments of the mutant SH3BP2 nucleotide sequences. It is apparent to those skilled in the art that other unique fragments derived from the mutant SH3BP2 nucleotide sequences or sequences complementary thereto can also be used as primers.

The invention further provides nucleic acid detection techniques based on hybridization of labeled probes, e.g., fluorescent in-situ hybridization (FISH), which are capable of detecting small amounts of mutant SH3BP2 sequences and are extremely useful herein. Thus, in accordance with the present invention, the presence of a mutant SH3BP2 nucleic acid molecule containing a mutant SH3BP2 nucleic acid point mutation(s) in a sample can be detected by contacting the sample one or more nucleic acid probes which hybridize to a mutant SH3BP2 mutant domain, and detecting the presence of a nucleic acid molecule within the sample that hybridizes to the probe(s).

Nucleic acid probes and primers for hybridization which are derived from mutant SH3BP2 can be synthesized on an oligonucleotide synthesizer such as those commercially available from Applied Biosystems (California). DNA or RNA probes can also be derived by PCR using two primers from the mutant SH3BP2 gene.

As is well-known in the art, probes useful in detecting nucleic acid molecules can be labeled directly by attaching a label to the probe or indirectly by causing a labeled binding agent to couple to the probe after hybridization. Examples of labels include fluorochromes such as fluorescein, Texas Red® and green fluorescent protein, enzymes such as horse radish peroxidase and radioactive isotopes. Signal amplification systems may also be utilized herein, e.g., avidin, streptavidin and biotin complexes or antibody hapten complexes. Such methods and systems are well known and are discussed generally, e.g., in Alberts et al., *Molecular Biology of the Cell*, 2nd ed., pp. 174-193, incorporated herein by reference. Exemplary detectable labels include green fluorescent protein and Texas Red®, for use in assays which rely upon detecting fluorescence, microscopy, spectrophotometry, fluorescent plate readers and flow sorters.

Additional compositions and methods for detecting the mutant SH3BP2 nucleic acid molecules and polypeptides utilize antibodies, fragments of antibodies (embraced within the definition of antibodies, herein) and labels, and signal amplification techniques involving antibodies. Antibodies which are immunoreactive to mutant SH3BP2 nucleic acid molecule or to the mutant SH3BP2 polypeptide or to unique fragments of these are generated by known techniques, e.g., by immunization of animals such as mice with mutant SH3BP2 nucleic acid or with mutant SH3BP2 polypeptide or unique fragments thereof which include the point mutation. Polyclonal and monoclonal antibodies may be generated using immortal cell lines for continuous production. Antibodies to mutant SH3BP2 nucleic acid or polypeptide or to unique fragments of each which include the point mutation are conjugated to labels such as those described above. Alternatively, if the so-called primary antibody is not labeled, it can be detected with a second labeled antibody which is immunoreactive with the first antibody. In addition to utilizing antibodies and fragments thereof, the foregoing detection methods can also be performed using other binding agents such as those described herein including peptide and non-peptide compounds produced in libraries.

According to another aspect of the invention, isolated polypeptides encoded by any of the isolated mutant SH3BP2 nucleic acid molecules of the invention are provided. Preferably, the isolated polypeptides of the invention include a sequence selected from the group consisting of SEQ ID NO:6, SEQ ID NO:8, SEQ ID NO:10, SEQ ID NO: 12, SEQ ID NO:14, SEQ ID NO:16, SEQ ID NO:18, SEQ ID NO:20, SEQ ID NO:22, and SEQ ID Nos:64-100. As used herein, a mutant SH3BP2 refers to a polypeptide encoded by mutant SH3BP2 nucleic acid molecule of the invention and which contains a mutant SH3BP2 polypeptide domain. A mutant SH3BP2 polypeptide domain refers to the minimum amino acid sequence which identifies a polypeptide as a mutant SH3BP2 polypeptide. Typically, these mutations are present in the domain encoded by exon 9. (See, e.g., FIG. 2). Mutant SH3BP2 polypeptides may be identified in a similar manner to the identification of unique polypeptide fragments, as described herein. The point mutations which result in the cherubism phenotype frequently result in changes in the amino acids at amino acid positions 415, 418, and 420 of SEQ ID NO:2 (see also Table 2); however, it is to be understood that the invention also embraces mutant SH3BP2 polypeptides having one or more amino acid mutations present in the polypeptide encoded by exon 9, in particular, mutations present at amino acid positions, 415, 416, 417, 418, 419 and/or 420 of SEQ ID NO:2.

In the preferred embodiments, the isolated mutant SH3BP2 polypeptides are immunogenic and can be used to generate binding agents (e.g., antibodies and antibody fragments) for use in diagnostic and therapeutic applications. As diagnostic or prognostic indicators, such binding agents are useful for determining the presence or absence of a mutant SH3BP2 polypeptide, and/or for determining the level of such a polypeptide in a sample. Samples to be analyzed include but are not limited to biological samples such as biopsy samples. The mutant SH3BP2 polypeptides used for generating binding agents are unique polypeptides and, therefore, the binding agents so generated are those which selectively bind to a mutant SH3BP2 polypeptide and not to a wild type SH3BP3 polypeptide.

A unique fragment of an mutant SH3BP2 polypeptide, in general, has the features and characteristics of unique fragments as discussed above in connection with nucleic acid molecules. As will be recognized by those skilled in the art, the size of the unique fragment will depend upon factors such as whether the fragment constitutes a portion of a conserved protein domain. Thus, some regions of SEQ ID NO:6, SEQ ID NO:8, SEQ ID NO:10, SEQ ID NO: 12, SEQ ID NO:14, SEQ ID NO:16, SEQ ID NO:18, SEQ ID NO:20, SEQ ID NO:22, and SEQ ID Nos:64-100 will require longer segments to be unique while others will require only short segments, typically between 4 and 12 amino acids (e.g. 4, 5, 6, 7, 8, 9, 10, 11 and 12 amino acids long or more, including each integer up to the full length, </=561 amino acids long). Virtually any segment of SEQ ID NO:6, SEQ ID NO:8, SEQ ID NO:10, SEQ ID NO: 12, SEQ ID NO:14, SEQ ID NO:16, SEQ ID NO:18, SEQ ID NO:20, SEQ ID NO:22, and SEQ ID Nos: 64-100, excluding the ones that share identity with it (e.g., the wild type SH3BP2 polypeptide, and fragments thereof, or other polypeptides published prior to the invention or application filing date) that is 9 or more amino acids in length will be unique.

One important aspect of a unique fragment is its ability to act as a signature for identifying the polypeptide. Another is its ability to provide an immune response in an animal. Those skilled in the art are well versed in methods for selecting unique amino acid sequences, typically on the basis of the ability of the unique fragment to selectively distinguish the sequence of interest from unrelated proteins. A comparison of the sequence of the fragment to those on known databases typically is all that is necessary.

The invention embraces variants of the mutant SH3BP2 polypeptides described above. As used herein, a "variant" of a mutant SH3BP2 polypeptide is a polypeptide which contains one or more modifications to the primary amino acid sequence of a mutant SH3BP2 polypeptide. Modifications which create a mutant SH3BP2 variant are typically made to the nucleic acid which encodes the mutant SH3BP2 polypeptide and can include deletions, point mutations, truncations, amino acid substitutions and addition of amino acids or non-amino acid moieties to: 1) reduce or eliminate a functional activity of the polypeptide, such as its ability to bind a ligand or to activate transcription of a particular genomic locus; 2) enhance a property of the polypeptide, such as protein stability in an expression system or the stability of protein-protein binding; 3) provide a novel activity or property to the polypeptide, such as addition of an antigenic epitope or addition of a detectable moiety; or 4) to provide equivalent or better binding to the polypeptide by another molecule, or to another molecule by the polypeptide.

Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the mutant SH3BP2 amino acid sequence. One of skill in the art will be familiar with methods for predicting the effect on protein conformation of a change in protein sequence, and can thus "design" a variant mutant SH3BP2 polypeptide according to known methods. One example of such a method is described by Dahiyat and Mayo in *Science* 278:82-87, 1997, whereby proteins can be designed de novo. The method can be applied to a known protein to vary only a portion of the polypeptide sequence. By applying the computational methods of Dahiyat and Mayo, specific variants of a mutant SH3BP2 polypeptide can be proposed and tested to determine whether the variant retains a desired conformation.

Variants can include mutant SH3BP2 polypeptide which are modified specifically to alter a feature of the polypeptide unrelated to its physiological activity. For example, cysteine residues can be substituted or deleted to prevent unwanted disulfide linkages. Similarly, certain amino acids can be changed to enhance expression of a mutant SH3BP2 polypeptide by eliminating proteolysis by proteases in an expression system.

Mutations of a nucleic acid molecule which encode a mutant SH3BP2 polypeptide preferably preserve the amino acid reading frame of the coding sequence and, preferably, do not create regions in the nucleic acid molecule which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and-tested for one or more activities to determine which mutation provides a variant polypeptide with the desired properties. Further mutations can be made to variants (or to non-variant mutant SH3BP2 polypeptides) which are silent as to the amino acid sequence of the polypeptide, but which provide preferred codons for translation in a particular host. Still other mutations can be made to the non-coding sequences of a mutant SH3BP2 gene or cDNA clone to enhance expression of the polypeptide. The skilled artisan will realize that conservative amino acid substitutions may be made in mutant SH3BP2 polypeptides to provide functionally equivalent variants of the foregoing polypeptides, i.e., the variants retain the functional capabilities of the mutant SH3BP2 polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the mutant SH3BP2 polypeptides include conservative amino acid substitutions of SEQ ID NO:6, SEQ ID NO:8, SEQ ID NO:10, SEQ ID NO: 12, SEQ ID NO:14, SEQ ID NO:16, SEQ ID NO:18, SEQ ID NO:20, SEQ ID NO:22, and SEQ ID Nos:64-100. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Thus functionally equivalent variants of mutant SH3BP2 polypeptides, i.e., variants of mutant SH3BP2 polypeptides which retain the function of the natural mutant SH3BP2 polypeptides, are contemplated by the invention. Conservative amino-acid substitutions in the amino acid sequence of mutant SH3BP2 polypeptides to produce functionally equivalent variants of mutant SH3BP2 polypeptides typically are made by alteration of the nucleic acid sequences encoding mutant SH3BP2 polypeptides. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding a mutant SH3BP2 polypeptide. The activity of functionally equivalent fragments of mutant SH3BP2 polypeptides can be tested by cloning the gene encoding the altered mutant SH3BP2 polypeptide into a bacterial or mammalian expression vector, introducing the vector into an appropriate host cell, expressing the altered mutant SH3BP2 polypeptide, and testing for a functional capability of the mutant SH3BP2 polypeptides as disclosed herein.

The mutant SH3BP2 polypeptides may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mutant SH3BP2 mRNA in cell-free extracts such as the reticulocyte lysate system also may be used to produce mutant SH3BP2 polypeptides. Those skilled in the art also can readily follow known methods for isolating mutant SH3BP2 polypeptides. These include, but are not limited to, immunochromatography, HPLC, size-exclusion chromatography, ion-exchange chromatography and immune-affinity chromatography.

According to another aspect of the invention, isolated mutant SH3BP2 binding agents (e.g., binding nucleic acid molecules such as probes or primers or ribozymes, and binding polypeptides such as antibodies) which selectively bind to a mutant SH3BP2 nucleic acid molecule or to a mutant SH3BP2 polypeptide encoded by the isolated nucleic acid molecules of the invention are provided. Preferably, the isolated binding agents selectively bind to a nucleic acid molecule comprising a nucleotide sequence selected from the group consisting of SEQ ID NO:5 (generic mutant—full length); SEQ ID NO:7 (generic mutant domain); SEQ ID NO:9 ("H" family mutation), SEQ ID NO:11 ("K" family mutation), SEQ ID NO:13 ("A,B" family mutation), SEQ ID NO:15 ("C,F,J,M,O" family mutation), SEQ ID NO:17 ("L" family mutation), SEQ ID NO: 19 ("G" family mutation), SEQ ID NO:21 ("N" family mutation), SEQ ID NO:26 (genomic mutant SH3BP2), SEQ ID NOs:27-63 (mutant SH3BP2 exon 9) and a genomic mutant SH3BP2 nucleic acid molecule having a sequence identical to SEQ ID NO: 25 with the exception that a mutant exon 9 selected from the group consisting of SEQ ID NOs: 27-63 is used in place of the lo wild type exon 9. In certain embodiments, the binding molecules do not hybridize to SEQ ID NO:1 (human "WT" SH3BP2 full length sequence) or SEQ ID NO:3 (human WT domain). Alternatively, the binding agents selectively bind to a polypeptide comprising an amino acid sequence selected from the group consisting of SEQ ID NO:6, SEQ ID NO:8, SEQ ID NO:10, SEQ ID NO: 12, SEQ ID NO:14, SEQ ID NO:16, SEQ ID NO:18, SEQ ID NO:20, SEQ ID NO:22, or SEQ ID Nos:64-100, or to unique fragments of the foregoing nucleic acid molecules and polypeptides. In certain embodiments, the binding agents do not bind to SEQ ID NO:2 or to fragments thereof which do not include a mutant domain. In the preferred embodiments, the isolated binding polypeptides include antibodies and fragments of antibodies (e.g., Fab, F(ab)$_2$, Fd and antibody fragments which include a CDR3 region which binds selectively to a mutant SH3BP2 nucleic acid molecule or polypeptide). Preferably, the antibodies for human therapeutic applications are human antibodies.

As is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example; are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves binding agents in the form of binding polypeptides of numerous size and type that bind selectively to mutant SH3BP2 polypeptides, and complexes or fusion proteins containing mutant SH3BP2 polypeptides. These binding polypeptides also may be derived from sources other than antibody technology. For example, such polypeptide binding agents can be provided by degenerate peptide libraries which can be readily prepared in solution, in immobilized form, as bacterial flagella peptide display libraries or as phage display libraries. Combinatorial libraries also can be synthesized of peptides containing one or more amino acids. Libraries further can be synthesized of peptides and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the mutant SH3BP2 polypeptide or a complex containing a mutant SH3BP2 polypeptide, but not to a wild type SH3BP2 polypeptide. This process can be repeated through several cycles of reselection of phage that bind to the mutant SH3BP2 polypeptide or to a complex containing a mutant SH3BP2 polypeptide. Repeated rounds lead to enrichment of phage bearing particular sequences. DNA sequence analysis can be conducted to identify the sequences of the expressed polypeptides. The minimal linear portion of the sequence that binds to the mutant SH3BP2 polypeptide or complex can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the mutant SH3BP2 polypeptides. Thus, the mutant SH3BP2 polypeptides of the invention, or a unique fragment thereof, or complexes of mutant SH3BP2 can be used to screen peptide libraries, including phage display libraries, to identify and select peptide binding polypeptides that selectively bind to the mutant SH3BP2 polypeptides of the invention. Such molecules can be used, as described, for screening assays, for purification protocols, for interfering directly with the functioning of mutant SH3BP2 and for other purposes that will be apparent to those of ordinary skill in the art. In addition, such molecules can also be tested for their ability to inhibit mutant SH3BP2 polypeptide production. Such inhibition can result from interference with transcription and/or translation of mutant SH3BP2 nucleic acid molecules. Compounds and libraries can be so tested for these abilities using screening assays such as those described below.

A mutant SH3BP2 polypeptide, or a unique fragment thereof, also can be used to isolate naturally occurring, polypeptide binding agents which may associate with the mutant SH3BP2 polypeptide in a cell. Isolation of binding agents may be performed according to well-known methods. For example, isolated mutant SH3BP2 polypeptides can be attached to a substrate, and then a solution suspected of containing an mutant SH3BP2 binding agent may be applied to the substrate. If the binding agent for mutant SH3BP2 polypeptides is present in the solution, then it will bind to the substrate-bound mutant SH3BP2 polypeptide. The binding agent then may be isolated. Other proteins which are binding agents for mutant SH3BP2 may be isolated by similar methods without undue experimentation.

The isolated nucleic acid molecules disclosed herein have various utilities, including their use as probes and primers in diagnostic assays for identifying the presence of mutant SH3BP2 nucleic acid molecules in a sample. Additionally they may function as agents for generating mutant SH3BP2 polypeptides and mutant SH3BP2 binding agents that also can be used in diagnostic and therapeutic assays to determine the presence or absence of a mutant SH3BP2 molecule and/or to determine the level of a mutant SH3BP2 molecule in a sample. Thus, the foregoing mutant SH3BP2 nucleic acid molecules, polypeptides and binding agents can be used, inter alia, in the diagnosis or treatment of conditions characterized by the expression or presence of a mutant SH3BP2 nucleic acid molecule or polypeptide (See, for example, Examples).

Since, as demonstrated herein, the mutant SH3BP2 nucleic acid molecule and polypeptide is found in tissue associated with a disorder of bone homeostasis, the role of mutant SH3BP2 molecules in mediating bone homeostasis is clear. Without wishing to be bound by any particular theory, there are several mechanisms by which, for example, the mutant SH3BP2 molecules may mediate a bone homeostasis disorder. SH3BP2 was initially identified by screening a phage expression library for proteins that can bind to the SH3 domain of the proto-oncogene c-Abl, and it was shown to contain a proline-rich 10 amino acid residue-long sequence responsible for SH3 binding (Ren, R. et al., *Science* 259 (1993), 1157-1161). This SH3 ligand motif (PPAYPPPPVP, SEQ ID NO: 103) is located 205 amino acid residues upstream of the mutated region Arg415-Gly420. The N-terminal pleckstrin homology (PH) domain belongs to a class of interaction domains that are found in a number of eukaryotic signaling proteins. They can bind to other proteins as well as to inositol phosphates, but the binding partners for the PH domain in SH3BP2 are still unknown. The C-terminal SH2 domain is likely to bind with high affinity to tyrosine-phosphorylated peptides (Songyang, Z. et al., *Mol. Cell. Biol.* 14 (1994), 2777-2785; Pawson, T. et al., *Cell* 71 (1992), 359-362). The combination of the three protein binding modules in SH3BP2 and its affinity for c-Abl via its SH3 (Ren, R. et al., *Science* 259 (1993), 1157-1161; Sparks, A. B. et al., *Proc. Natl. Acad. Sci. USA* 93 (1996), 1540-1544) binding domain make it a possible adapter protein that could organize the formation of functional complexes involving c-Abl.

SH3BP2 is also likely to interact with cytoplasmic signaling molecules playing a role in transcriptional activation in hematopoietic cells through its SH2 domain (Deckert, M., et al., *Immunity* 9 (1998), 595-605). Thus, it could function primarily as a regulator of c-Abl function in some cells, while controlling transcriptional regulation through interaction with other kinases and signaling complexes in other cells. Such a potential dual function may explain the cellular phenotype of the fibro-osseous lesions in cherubism. Not only are the lesions reminiscent of fibrous dysplasia of bone caused by mutations in GNSA1 resulting in deficient osteoblastic differentiation from mesenchymal percursors. (Weinstein, L S, et al., *N. Engl. J. Med.* 325 (1991), 1688-1695; Bianco P. et al., *J. Bone Miner Res.* 15 (2000), 120-128), but the accumulation of large numbers of osteoblast-like cells in cherubism suggests an abnormal formation of these monocyte-derived, multinucleated cells as well. The clustering of amino acid missense mutations in SH3BP2 suggest that they represent gain of function mutations. SH3BP2 lies within a region that is frequently deleted in Wolf-Hirschhorn Syndrome (WHS) (Hirschhorn, K. et al., *Humangenetik* 1 (1965), 479-482; Zollino, M., et al., *Am. J. Med. Genet.* 18 (2000), 254-261) patients. Haploinsufficiency of SH3BP2 in these patients does not result in cherubism or cherubism-like characteristics, which supports our hypothesis that the mutations in SH3BP2 lead to a gain of function.

Although not wishing to be bound to any particular theory or mechanism, we believe that SH3BP2 may enhance the ability of the protein to engage in complexes that are important for differentiation and activation of osteoblasts while they may affect in a negative manner the function of c-Abl in differentiating osteoblasts. Interestingly, osteoblastic differentiation is impaired in c-Abl null mice, resulting in osteoporosis (Li, B. et al., *Nat. Genet.* 24 (2000), 304-308). The ability to shuttle between focal adhesions and the nucleus makes c-Abl a good candidate for being a mediator of integrin-regulated gene expression (Lewis, J. M. et al., *Proc. Natl. Acad. Sci. USA* 93 (1996), 15174-15179) and cell cycle progression (Welch, P J, et al., *Cell* 75 (1993), 779-790). It is conceivable that at age 3 (frequently the age of onset of the disease) there are signals transmitted through the extracellular matrix of the mandible and maxilla that are unique to these bones and are triggered by the eruption of secondary teeth. Thus, the onset of the abnormalities of cherubism and their organ-restricted characteristics may be related to the dental developmental process. Thus, we believe that administration of agents which inhibit mutant SH3BP2 expression will alleviate the symptoms associated with various bone homeostasis disorders, including cherubism, bone tumors, osteoporosis and osteopetrosis. Similarly, we believe that the detection of the mutant SH3BP2 molecules of the invention will be useful for definitively diagnosing these and other bone homeostasis disorders.

According to another aspect of the invention, a method of identifying the presence of an SH3BP2 mutant molecule in a sample is provided. In general, the method involves analyzing the sample for the presence of a SH3BP2 mutant nucleic acid molecule or a SH3BP2 mutant polypeptide.

In certain embodiments, the method further involves the steps of contacting the sample with at least two nucleic-acid amplification primers and amplifying DNA in the sample prior to analyzing the sample for the presence of a SH3BP2 mutant nucleic acid molecule. The method employs a first nucleic acid amplification primer and a second nucleic acid amplification primer that are capable of hybridizing to a SH3BP2 mutant nucleic acid molecule and, thereby, useful in amplifying a nucleic acid comprising a sequence selected from the group consisting of SEQ ID NO:7 (generic mutant domain); SEQ ID NO:9 ("H" family mutation), SEQ ID NO:11 ("K" family mutation), SEQ ID NO:13 ("A,B" family mutation), SEQ ID NO:15 ("C,F,J,M,O" family mutation), SEQ ID NO:17 ("L" family mutation), SEQ ID NO: 19 ("G" family mutation), SEQ ID NO:21 ("N" family mutation), SEQ ID NO:26 (genomic mutant SH3BP2), SEQ ID NOs: 27-63 (mutant SH3BP2 exon 9) and a genomic mutant SH3BP2 nucleic acid molecule having a sequence identical to SEQ ID NO: 25 with the exception that a mutant exon 9 selected from the group consisting of SEQ ID NOs: 27-63 is used in place of the wild type exon 9. Following hybridization, the method involves amplifying a primed nucleic acid molecule which hybridizes to the first and the second nucleic acid amplification primers; and detecting the presence of an amplified nucleic acid molecule in the sample.

In yet other embodiments, the method involves contacting the sample with one or more nucleic acid probes, wherein the nucleic acid probe is capable of hybridizing to a nucleic acid sequence selected from the group consisting of: nucleic acid sequences which hybridize to a sequence selected from one or more of the following sequences under stringent conditions: SEQ ID NO:7 (generic mutant domain); SEQ ID NO:9 ("H" family mutation), SEQ ID NO:11 ("K" family mutation), SEQ ID NO:13 ("A,B" family mutation), SEQ ID NO:15 ("C,F,J,M,O" family mutation), SEQ ID NO:17 ("L" family mutation), SEQ ID NO: 19 ("G" family mutation), SEQ ID NO:21 ("N" family mutation SEQ ID NO:26 (genomic mutant SH3BP2), SEQ ID NOs:27-63 (mutant SH3BP2 exon 9) and a genomic mutant SH3BP2 nucleic acid molecule having a sequence identical to SEQ ID NO: 25 with the exception that a mutant exon 9 selected from the group consisting of SEQ ID NOs: 27-63 is used in place of the wild type exon 9 and, preferably, which does not hybridize to SEQ ID NO:1 (human "WT" SH3BP2 full length sequence) or SEQ ID NO:3 (human WT domain) or SEQ ID NO:25 (genomic WT SH3BP2) under stringent conditions, and detecting the presence of a SH3BP2 mutant nucleic acid in the sample which hybridizes to the nucleic acid probe.

In yet other embodiments, the method involves contacting the sample with one or more binding agents, wherein the binding agent is capable of selectively binding to a polypeptide having an amino acid sequence selected from the group consisting of: SEQ ID NO:6, SEQ ID NO:8, SEQ ID NO:10, SEQ ID NO: 12, SEQ ID NO:14, SEQ ID NO:16, SEQ ID NO:18, SEQ ID NO:20, SEQ ID NO:22, and SEQ ID Nos: 64-100; and detecting the presence of a SH3BP2 mutant polypeptide in the sample which binds the binding agent. Preferably, the binding agent is an antibody or a fragment thereof that selectively binds to the SH3BP2 mutant polypeptide in the sample and does not bind to a non-mutant SH3BP2 polypeptide that may be present in the sample.

The diagnostic methods of the invention are particularly useful for: evaluating the susceptibility of a human subject to a disorder of bone homeostasis, evaluating causation of a bone homeostasis disorder in a human subject, or for evaluating the genetic predisposition of a human subject to have offspring with a bone homeostasis disorder. Such methods differ primarily in the selection of the human subject (e.g., the human subject exhibits a bone homeostasis disorder or is suspected of having a predisposition to developing the disorder or having offspring susceptible of developing the disorder). In general, such methods involve obtaining a sample of DNA from the subject; and evaluating the sample of DNA for the presence of nucleotides encoding a "mutant residue" at any one or more amino acid positions encoded by exon 9 of the SH3BP2 gene product. In certain preferred embodiments, the sample of DNA is evaluated for the presence of nucleotides encoding a "mutant residue" in the polypeptide encoded by exon 9, particularly at positions 415-420 and, more particularly, at any one or more amino acids at positions 415, 418, and 420, of the SH3BP2 gene product. The presence of a mutant residue is indicative of the condition for which the subject is being tested. Exemplary mutant residues that are diagnostic of cherubism are described in more detail in the Examples.

According to yet another aspect of the invention, a method of screening for an agent that inhibits the production of a SH3BP2 mutant polypeptide is provided. The method involves: (a) determining the level of a SH3BP2 mutant molecule (e.g., nucleic acid, polypeptide) in the absence of a putative inhibitor, (b) determining the level of a SH3BP2 mutant molecule in the presence of the putative inhibitor, and (c) comparing the level of the SH3BP2 mutant molecule in the presence and absence of the putative inhibitor. A decrease in the level of the SH3BP2 mutant molecule in the presence of the putative inhibitor indicates that the putative inhibitor is an agent that inhibits the production of a SH3BP2 mutant polypeptide. In certain embodiments, the agent inhibits transcription of a SH3BP2 mutant nucleic acid molecule. In yet other embodiments, the agent inhibits translation of a SH3BP2 mutant nucleic acid molecule.

According to yet another aspect of the invention, methods for identifying agents which bind or otherwise interact with the SH3BP2 molecules of the invention are provided. The methods are useful for identifying agents which modulate SH3BP2 molecule activity at the level of its expression (defined herein as including replication, transcription or translation), or mutant SH3BP2 dependent cellular function (for example, binding to a nucleic acid or a ligand, mutant SH3BP2-mediated cellular signalling). Generally, the screening methods involve assaying for compounds which have a net result of inhibiting production of mutant SH3BP2 polypeptides or inhibiting the function of mutant SH3BP2 polypeptides. Such methods are adaptable to automated, high throughput screening of compounds.

In a preferred embodiment, a method involves screening for an agent that inhibits the production of a mutant SH3BP2 molecule (nucleic acid or polypeptide). The method involves determining and comparing the level of, for example, a mutant SH3BP2 molecule in the absence and in the presence of a test compound. According to the method, a decrease in the level of a mutant SH3BP2 molecule in the presence of the compound is indicative of an agent that inhibits the production of a mutant SH3BP2 molecule. The compound can be synthesized or harvested from a variety of sources as described herein. The compound can be peptide or non-peptide in nature.

As mentioned above, the agent may be one which inhibits transcription of a mutant SH3BP2 nucleic acid molecule. Alternatively, the agent may be one which inhibits translation of a mutant SH3BP2 nucleic acid molecule. The screening assay can be carried out in a cell, a cell-free system, a tissue or in an animal such as a transgenic, non-human animal.

A wide variety of assays for screening pharmacological agents are provided, including, labeled in vitro protein-protein binding assays, electrophoretic mobility shift assays, immunoassays, cell-based assays such as two- or three-hybrid screens, expression assays, etc. For example, two-hybrid screens are used to rapidly examine the effect of transfected nucleic acid molecules on the intracellular binding of mutant SH3BP2 polypeptide or fragments thereof to intracellular targets. The transfected nucleic acid molecules can encode, for example, combinatorial peptide libraries or cDNA libraries. Convenient reagents for such assays, e.g., GAL4 fusion proteins, are known in the art. An exemplary cell-based assay involves transfecting a cell with a nucleic acid encoding, for example, a mutant SH3BP2 polypeptide fused to a GAL4 DNA binding domain and a nucleic acid encoding a reporter gene operably linked to a gene expression regulatory region, such as one or more GAL4 binding sites. Activation of reporter gene transcription occurs when the mutant SH3BP2 and reporter fusion polypeptides bind to each other such as to enable transcription of the reporter gene. Agents which modulate a mutant SH3BP2 polypeptide mediated cell function are then detected through a change in the expression of reporter gene. Methods for determining changes in the expression of a reporter gene are known in the art. In preferred embodiments, the agents so identified are also further screened to preclude those that also bind to the wild type SH3BP2 polypeptides.

Mutant SH3BP2 polypeptide fragments used in the methods, when not produced by a transfected nucleic acid are added to an assay mixture as an isolated polypeptide. Mutant SH3BP2 polypeptides preferably are produced recombinantly, although such polypeptides may be isolated from biological extracts. Recombinantly produced mutant SH3BP2 polypeptides include chimeric proteins comprising a fusion of a mutant SH3BP2 polypeptide with another polypeptide, e.g., a polypeptide capable of providing or enhancing protein-protein binding, sequence specific nucleic acid binding (such as GAL4), enhancing stability of the mutant SH3BP2 polypeptide under assay conditions, or providing a detectable moiety, such as green fluorescent protein or Flag epitope.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily modified through conventional chemical, physical, and biochemical means. Further, known pharmacological agents may be subjected to directed or random chemical modifications such as acylation, alkylation, esterification, amidification, etc. to produce structural analogs of the agents.

In connection with the screening assays and diagnostic methods, the invention also provides novel kits which are useful for detecting/measuring the levels of the nucleic acid molecules of the invention, expression products of the invention or anti-mutant SH3BP2 antibodies. In the case of nucleic acid detection, pairs of primers for amplifying mutant SH3BP2 nucleic acid molecules can be included. The preferred kits would include controls such as known amounts of nucleic acid probes, mutant SH3BP2 epitopes (such as mutant SH3BP2 expression products) or anti-mutant SH3BP2 antibodies, as well as instructions or other printed material. In certain embodiments the printed material can characterize the risk of developing a disorder that is characterized by mutant SH3BP2 nucleic acid or polypeptide expression based upon the outcome of the assay. The reagents may be packaged in containers and/or coated on wells in predetermined amounts, and the kits may include standard materials such as labeled immunological reagents (such as labeled anti-IgG antibodies) and the like. One kit is a packaged polystyrene microtiter plate coated with a mutant SH3BP2 polypeptide and a container containing labeled anti-human IgG antibodies. A well of the plate is contacted with, for example, a tissue lysate from a subject diagnosed as having a bone homeostasis disorder, washed and then contacted with the anti-IgG antibody. The label is then detected. A kit embodying features of the present invention is comprised of the following major elements: packaging an agent of the invention, a control agent, and instructions. Packaging is a box-like structure for holding a vial (or number of vials) containing an agent of the invention a vial (or number of vials) containing a control agent, and instructions. Individuals skilled in the art can readily modify packaging to suit individual needs.

It should be understood that kits which include reagents that are used to detect mutant SH3BP2 nucleic acid molecules and polypeptides encoded thereby can also be assembled so as to provide convenient access and use in clinical settings. For example, a kit can include a container which holds one or more amplification primers, a container which holds enzymes used for amplification, a container which holds washing solution(s), a container which holds detection reagents, and a sample well. Alternatively, a kit can include a container which holds one or more antibodies directed to a mutant SH3BP2 polypeptide or a fragment thereof, a container which holds washing solution(s), a container which holds detection reagents, and a sample well. It is also contemplated that a kit may include a container having one or more labeled or unlabeled probes capable of hybridizing to the SH3BP2 nucleic acid molecule comprising nucleotides 1451-1471 of SEQ ID NO:5, or corresponding mRNA and, if the probe is unlabeled, a container having a labeled specific binding agent of the probe or to a recognition site on the probe, e.g., biotinylated probe, a container which holds washing solution(s), a container which holds detection reagents, and a sample well.

Examples of detection reagents include radiolabeled probes, enzymatic labeled probes (horse radish peroxidase, alkaline phosphatase), and affinity labeled probes (biotin, avidin, or streptavidin). For antibodies, examples of detecting reagents include, but are not limited to, labeled secondary antibodies, or, if the primary antibody is labeled, the chromophoric, enzymatic, or antibody binding reagents which are capable of reacting with the labeled antibody. The antibodies, primers and nucleic acid probes described herein can readily be incorporated into one of the established kit formats which are well known in the art.

In some instances, the foregoing detection methods and kits may also comprise a control and/or comparison with a control. As used herein, a control can include a known amount of a mutant SH3BP2 nucleic acid molecule or a fragment thereof or a mutant SH3BP2 polypeptide or a fragment thereof (such as an antigenic fragment). In preferred embodiments the control is a similar tissue sample from a subject who does not express a mutant SH3BP2 nucleic acid molecule or polypeptide or similar normal tissue from the same subject.

The methods described herein generally involve detection of a mutant SH3BP2 nucleic acid molecule or a polypeptide in a sample. Such a sample can be, but is not limited to, a tissue or a biological fluid, or any type of sample which typically is assessed to diagnose a disorder of bone homeostasis. SH3BP2 is expressed in blood leukocytes, bone marrow, and bone. Accordingly, exemplary samples that can be tested for the presence of a mutant SH3BP2 molecule include blood, bone marrow, skin biopsies, and iliac crest biopsies. Both invasive and non-invasive techniques can be used to obtain such samples and are well documented in the art.

According to a yet another aspect of the invention, a method for treating a subject having a bone homestasis disorder which, preferably, is further characterized by the presence of a SH3BP2 mutant nucleic acid molecule is provided. The method of treatment involves administering a mutant SH3BP2 molecule binding agent (e.g., a mutant SH3BP2 antisense molecule) to a subject in need of such treatment in an amount effective to treat the subject, wherein the subject is not otherwise in need of mutant SH3BP2 binding molecule administration.

In general, the therapeutic methods of the invention utilize the novel compositions of the invention (particularly antisense) to inhibit a mutant SH3BP2 function. All administration modes are possible, with localized (e.g., periodontal pockets)/systemic delivery preferred. Controlled release is also important. The agents of the invention can be administered alone or in combination with another therapeutic agent for treating the condition. Thus, as used herein, a therapeutic agent is an agent other than the mutant SH3BP2 nucleic acid molecules, polypeptides, binding agents of the invention which has been reported to possess therapeutic effectiveness toward the disorder being treated. A therapeutic agent is also different from those agents described herein which upon administration inhibit or downregulate the production of mutant SH3BP2 polypeptides. In some embodiments, the foregoing agents of the invention may be administered substantially simultaneously with the therapeutic agents. By substantially simultaneously, it is meant that the agent of the invention is administered to a subject close enough in time with the administration of the therapeutic agent so that the two compounds may exert an additive or even synergistic effect, (e.g., reducing a tumor mass).

As used herein, a bone homeostasis disorder refers to a disorder characterized by an abnormal imbalance between bone formation and bone degradation. In certain embodiments, the bone homeostasis disorder is selected from the group consisting of osteoporosis, osteopetrosis; a bone tumor; and cherubism (MIM #118400). Additional disorders that can be tested in accordance with the methods of the invention to definitively diagnose whether the presented bone homeostasis disorder is mediated by a mutant SH3BP2 molecule include: Cassey disease (MIM #114000), Ramon syndrome (MIM #266270), Gingival fibromatosis (MIM #135300), Noonan-like multiple giant cell lesion syndrome (MIM #163955), McCune-albright syndrome (MIM #174800), giant cell granulomas, and giant cell tumors. The agent may be administered in accordance with standard clinical practice (e.g., systemic); however, in certain preferred embodiments relating to the treatment of cherubism, the agent is locally administered (e.g., to a periodontal pocket).

As used herein, treatment of a subject includes the prophylactic treatment of a subject at risk of developing a bone homeostasis disorder (e.g., associated with mutant SH3BP2 expression), as well as treatment of subjects suspected of having a disorder or known to have a bone homeostasis disorder associated with, or characterized by, mutant SH3BP2 expression. In such embodiments, the amount effective to treat the subject is the amount which inhibits either the development or the progression of a disorder or decreases the rate of progression of a disorder associated with mutant SH3BP2 expression. In some instances, the disorder is a proliferative disorder, such as a bone tumor. Thus, alternatively an effective amount is that amount which inhibits the growth and/or proliferation of a cell expressing a mutant SH3BP2 molecule. Agents which are useful in this regard include but are not limited to agents which bind specifically to the mutant SH3BP2 nucleic acid molecule and thereby prevent replication, transcription and/or translation thereof, agents which bind specifically to the mutant SH3BP2 polypeptide and thereby interfere or, in other instances, inhibit the association of the polypeptide with other polypeptides or nucleic acid molecules in the cell.

The prophylactic treatment methods of the invention optionally further comprise the selection of a subject at risk of developing a disorder prior to the administration of the agent. Such a subject may be identified using the diagnostic methods provided herein. A subject at risk may be one who exhibits symptoms of a bone homeostasis disorder, and/or one who expresses a mutant SH3BP2 nucleic acid molecule or a polypeptide. Other subjects at risk of developing such a disorder may be those with a family history of such disorders. Several such families are discussed in the Examples. Subjects with a family history of a bone homeostasis disorder, such as cherubism, may be considered subjects for prophylactic treatment.

The invention further provides a method for treating a subject who has already developed a bone homeostasis disorder which, preferably, is characterized by the presence of a mutant SH3BP2. The method involves administering a mutant SH3BP2 binding agent (e.g., a mutant SH3BP2 antisense molecule) to the subject in need of such treatment in an amount effective to treat the subject. As used herein, an amount effective to treat the subject is that amount effective to cause a medically desirable affect. For example, an effective amount may be that amount necessary to prevent or halt the progression of the disorder.

In the preferred therapeutic methods, a mutant SH3BP2 antisense molecule is administered to the subject to treat a bone homeostasis disorder. In an exemplary embodiment, DNA is introduced into cells producing mutant SH3BP2 polypeptide, the DNA being configured to produce antisense RNA that is complementary to mRNA that encodes mutant SH3BP2 polypeptide. In this latter example, the antisense mRNA hybridizes with the sense mRNA transcribed from the mutant SH3BP2 genomic locus thereby inhibiting synthesis of mutant SH3BP2 polypeptide. Methods of producing antisense mRNA and use thereof for inhibition of polypeptide production are well-known in the art. Expression vectors can be constructed to produce high levels of antisense RNA in transfected cells. This approach has led to reduced expression of oncogenes in exemplary instances whereby antisense oncogene constructs have reverted the growth properties of tumor cells to near normal, slowed their growth or induced apoptosis. See Watson et al., *Recombinant DNA*, 2d ed., 1992. For example, Philadelphia human chronic myelogenous leukemia (CML) cells that contain the BCR/ABL chromosomal translocation have been eradicated using antisense molecules targeted to this oncogene in clinical, pre-clinical, and laboratory settings. *J. Nat'l. Cancer Inst.* Vol. 89, No. 2, Jan. 15, 1997. A similar approach is provided herein directed to the treatment of disorders associated with the mutant SH3BP2 point mutations. For example, tumor cells harboring the mutant SH3BP2 genomic locus are treated in vivo or ex vivo with antisense molecules directed at the oncogene mRNA to induce an inhibition of cell responsiveness to tumor inducing factors, or an inhibition of factor-independent cell growth.

The pharmaceutical preparations, as described above, are administered in effective amounts. The effective amount will depend upon the mode of administration, the particular condition being treated and the desired outcome. It will also depend upon, as discussed above, the stage of the condition, the age and physical condition of the subject, the nature of concurrent therapy, if any, and like factors well known to the medical practitioner. For therapeutic applications, it is that amount sufficient to achieve a medically desirable result. In some cases this is a decrease in cell proliferation, a decrease in the size of a tumor, or an inhibition of tumor growth.

The invention further provides a medicament and a method of making a medicament. The medicament comprises an agent and a pharmaceutically acceptable carrier. The method involves placing an agent in a pharmaceutically acceptable carrier. The agent may be but is not limited to a mutant SH3BP2 nucleic acid molecule or a fragment thereof, a mutant SH3BP2 antisense nucleic acid molecule, a mutant SH3BP2 polypeptide or fragment thereof, and a mutant SH3BP2 binding agent, as described herein. In a further embodiment, the invention provides a medicament and a method of making the same which includes a mutant SH3BP2 binding agent formulated for use in the treatment of a disorder characterized by expression of a mutant SH3BP2 nucleic acid molecule or a polypeptide. In one embodiment, the medicament is formulated in a dose and/or a delivery formulation particularly tailored to the treatment of cherubism and/or delivery to a periodontal pocket.

Generally, doses of active compounds of the present invention would be from about 0.01 mg/kg per day to 1000 mg/kg per day. It is expected that doses ranging from 50-500 mg/kg will be suitable. A variety of administration routes are available. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. In some embodiments of the invention, the mode of administration is direct injection into the tissue surrounding a bone suspected of abnormal homeostasis. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule. When peptides are used therapeutically, in certain embodiments a desirable route of administration is by pulmonary aerosol. Techniques for preparing aerosol delivery systems containing peptides are well known to those of skill in the art. Generally, such systems should utilize components which will not significantly impair the biological properties of the antibodies, such as the paratope binding capacity (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing antibody or peptide aerosols without resorting to undue experimentation.

Compositions suitable for oral administration may be presented as discrete units, such as collagen matrices, floss, slow release capsules, tablets, lozenges, each containing a predetermined amount of the active agent. See, e.g., U.S. Pat. Nos. 5,750,651; 5,171,574; 5,645,591; 6,120,789; 5,023,082; and 6,174,934 for exemplary controlled release matrices that are useful in accordance with practicing the methods of the invention. Other compositions include suspensions in aqueous liquids or non-aqueous liquids such as a syrup, elixir or an emulsion.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

The mutant SH3BP2 nucleic acid molecules, polypeptides or fragments thereof, as well as binding agents (including antisense molecules) may be combined, optionally, with a pharmaceutically-acceptable carrier. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Various techniques may be employed for introducing nucleic acid molecules of the invention into cells, depending on whether the nucleic acid molecules are introduced in vitro or in vivo in a host. Such techniques include transfection of nucleic acid-$CaPO_4$ precipitates, transfection of nucleic acid molecules associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acid molecules of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acid molecules into cells, as is known by those skilled in the art. Such systems even permit oral delivery of nucleic acid molecules.

Other delivery systems can include time-release, delayed release or sustained release delivery systems. Such systems can avoid repeated administrations of the agents of the invention, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The molecular characterization of mutant SH3BP2 nucleic acid molecules and the polypeptides encoded thereby also permits the production of therapeutic agents which selectively locate and/or destroy cells containing the mutant SH3BP2 nucleic acid molecule, or its corresponding polypeptide. For example, radiolabeled antibodies or fragments of antibodies which are formulated to penetrate the cell target and bind to the mutant SH3BP2 nucleic acid molecule, or corresponding polypeptide can be contacted with cells suspected of containing a mutant SH3BP2 nucleic acid molecule or polypeptide. Since the radiolabeled antibodies or antibody fragments collect in the area of cells having the nucleic acid molecule, or corresponding polypeptide, such cells may be detected and localized by observing the locus of radioactivity generated by the antibodies or fragments of antibodies. In one important embodiment, the cells are contacted with the radiolabeled antibodies or fragments thereof in vivo and correspondingly, the term "contacting" in these embodiments also encompasses "injecting into a subject". Thus, in one embodiment, radiolabeled antibodies or fragments of antibodies which bind to the mutant SH3BP2 nucleic acid molecule, or corresponding polypeptide can be injected into a subject known to have or suspected of having a cell or a tumor containing mutant SH3BP2 nucleic acid molecules or corresponding polypeptides. Here, such cells or tumors may be detected and localized within a subject by observing the locus of radioactivity generated by the antibodies or fragments of antibodies. Methods of tumor localization using radiolabeled antibodies or fragments of antibodies (radioimmunodetection) are well-known in the art. See, e.g., U.S. Pat. No. 4,348,376 incorporated herein by reference. In a method similar to that described herein, other binding agents can be used for locating or visualizing cells or tumors containing mutant SH3BP2 nucleic acid molecules or corresponding polypeptides. Also, detection labels other than radioactive labels may be conjugated to a binding agent and used to detect and localize cells or tumors containing mutant SH3BP2 nucleic acid molecules or corresponding polypeptides. The advantage of radiolabeled binding agents is the ability to deliver radioactivity to target cells and tissues, thereby providing toxic doses of radioactivity to such cell and tissues. Preferably, the radiolabeled binding agents are those which specifically bind to the mutant domain nucleic acid molecule or polypeptide but not the nucleic acid molecule or polypeptide of the wild type SH3BP2 molecule.

Cells containing a mutant SH3BP2 nucleic acid molecule or polypeptide encoded thereby may be selectively destroyed by conjugating toxins to binding agents such as antibodies or fragments of antibodies which are capable of penetrating a cell target and binding to the nucleic acid molecule or polypeptide contained therein. Thus, as an example, by injecting a toxin/antibody or toxin/antibody fragment conjugate into a subject having mutant SH3BP2 nucleic acid molecule or polypeptide encoded thereby, wherein the antibody or antibody fragment is directed to a mutant SH3BP2 nucleic acid molecule or polypeptide, cells containing the nucleic acid molecule or polypeptide are preferentially destroyed by the toxin. Preferably, the binding agent in this latter embodiment is one which binds specifically to the mutant SH3BP2 nucleic acid molecule or polypeptide and not to the wild type molecules so as to reduce or prevent non-specific toxicity. In this manner, surgical resection of tumors may be avoided. Use of toxin conjugated antibodies or toxin conjugated antibody fragments is well-known in the art. See, e.g., U.S. Pat. No. 4,671,958, incorporated herein by reference. Examples of suitable toxins include those derived from diphtheria toxin, ricin and the like.

The following examples are included for purposes of illustration and are not intended to limit the scope of the invention.

EXAMPLES

Example 1

Cherubism

Figure 1:

Cherubism is an inherited syndrome characterized by excessive bone degradation of the upper and lower jaws. At around 3 years of age in affected individuals, multilocular cysts appear in mandibula and maxilla. The cysts fill with tumor-like tissue consisting of fibroblasts and osteoblast-like cells, causing a typical facial swelling (FIG. 1). The swelling regresses after puberty, but the osseous defects can be radiologically detected even in old age. We have previously mapped cherubism to chromosome 4p16.3[2]. Combining these published data with independent mapping results of Mangion et al.[3] and haplotype analyses of 11 additional families, we have defined the cherubism locus to a 1.5 Mb interval. About 26 known or predicted genes are contained in this locus between D4S127 and D4S115, allowing systematic analyses of these genes as candidates for cherubism. By sequencing cDNA and/or genomic DNA from affected and unaffected members of several pedigrees, we have excluded 15 previously described genes[4-6] as candidates, including GRK4, α-Adducin, WHSC2, RNF-4, WHSC1, LETM1, FGFR3 and TACC3. Finally, in 12 out of 15 families, we have detected point mutations that cause amino acid substitutions in the SH3-binding protein SH3BP2[7,8] (FIG. 3).

We have collected samples from 15 families, consisting of 66 individuals clinically diagnosed with cherubism, 4 obligate carries, and 79 unaffected subjects. Six of these families are of African-Brazilian, the others of Caucasian background. In 12 families, where mutations were found, the mutations co-segregate with the disease phenotype. We also cloned SH3BP2 cDNA from EBV-transformed patient lymphoblasts into TA-vectors and sequenced them. Half of the sequenced clones from each patient carried the mutation. We sequenced genomic DNAs from 100 unrelated and unaffected African-Brazilians and 100 Caucasian controls without detecting any of the sequence variants found in affected cherubism patients. The accumulation of co-segregating sequence variants in families with cherubism and their absence in unaffected controls provide compelling evidence that the mutations in SH3BP2 cause cherubism. Three families where no mutation in SH3BP2 could be detected were small, and linkage to the cherubism locus was inconclusive. Therefore, it is likely that cherubism in these families is caused by mutations in a gene other than SH3BP2.

SH3BP2 contains three modular peptide recognition domains, an N-terminal pleckstrin homology domain, a 10 amino acid residue-long SH3 binding site, and a C-terminal SH2 domain[7,8]. All mutations identified to date are in exon 9 and affect three amino acid residues within a 6-residue long sequence, RSPPDG, SEQ ID NO: 104, located 31 to 36 residues upstream of the SH2 domain (FIG. 2). As can be seen in Table 2, mutations in Pro418 (to Leu, Arg, or His) are the most common, seen in families A, B, C, F, J, L, M, and O. Other mutations result in Gly420 being replaced by Glu or Arg (in families G and N) and Arg415 being replaced by Pro or Glu (in families H and K).

SH3BP2 was initially identified by screening a phage expression library for proteins that can bind to the SH3 domain of the proto-oncogene c-Abl, and it was shown to contain a proline-rich 10 amino acid residue-long sequence responsible for SH3 binding[7]. This SH3 ligand motif (PPAY-PPPPVP, SEQ ID NO: 103) is located 205 amino acid residues upstream of the mutated region Arg415-Gly420. The N-terminal pleckstrin homology (PH) domain belongs to a class of interaction domains that are found in a number of eukaryotic signaling proteins. They can bind to other proteins as well as to inositol phosphates, but the binding partners for the PH domain in SH3BP2 are still unknown. The C-terminal SH2 domain is likely to bind with high affinity to tyrosine-phosphorylated peptides[9,10]. The combination of the three protein binding modules in SH3BP2 and its affinity for c-Abl via its SH3[7,11] binding domain make it a possible adapter protein that could organize the formation of functional complexes involving c-Abl.

SH3BP2 is also likely to interact with cytoplasmic signaling molecules playing a role in transcriptional activation in hematopoietic cells through its SH2 domain[12]. Thus, it could function primarily as a regulator of c-Abl function in some cells, while controlling transcriptional regulation through interaction with other kinases and signaling complexes in other cells. Such a potential dual function may explain the cellular phenotype of the fibro-osseous lesions in cherubism. Not only are the lesions reminiscent of fibrous dysplasia of bone caused by mutations in GNSA1 resulting in deficient osteoblastic differentiation from mesenchymal percursors[13, 14], but the accumulation of large numbers of osteoblast-like cells in cherubism suggests an abnormal formation of these monocyte-derived, multinucleated cells as well. The clustering of amino acid missense mutations in SH3BP2 suggest that they represent gain of function mutations. SH3BP2 lies within a region that is frequently deleted in Wolf-Hirschhorn Syndrome (WHS)[15,16] patients. Haploinsufficiency of SH3BP2 in these patients does not result in cherubism or cherubism-like characteristics, which supports our hypothesis that the mutations in SH3BP2 lead to a gain of function.

We speculate that they may enhance the ability of the protein to engage in complexes that are important for differentiation and activation of osteoblasts while they may affect in a negative manner the function of c-Abl in differentiating osteoblasts. Interestingly, osteoblastic differentiation is impaired in c-Abl null mice, resulting in osteoporosis[17]. The ability-to shuttle between focal adhesions and the nucleus makes c-Abl a good candidate for being a mediator of integrin-regulated gene expression[18] and cell cycle progressions[19]. It is conceivable that at age 3 (frequently the age of onset of the disease) there are signals transmitted through the extracellular matrix of the mandible and maxilla that are unique to these bones and are triggered by the eruption of secondary teeth. Thus, the onset of the abnormalities of cherubism and their organ-restricted characteristics may be related to the dental developmental process.

Example 1

Methods

Cherubism Families. Probands were identified by clinical collaborators and detailed family histories were taken. The diagnosis of affected and unaffected subjects was radiographically confirmed when necessary and consent from all participating family members had been obtained. The study was approved by the Institutional Review Boards of the sponsoring institutions.

Genetic analysis. Genomic DNA was prepared as previously described[2]. Information about published microsatellite markers for fine-mapping studies was obtained from the Genome Database (gdb). Additional markers were developed from Genbank sequences that were known to be located within the disease gene interval. Information about known genes within the locus were taken from publications. Searches for potential novel genes were performed with Gene Finder (http://searchlauncher.bcm.tmc.edu:9331/gene-finder/gf:html) and Genscan (http://genome.dkfz-heidelberg.de/cgi-bin/GENSCAN/genscan.cgi).

Mutation screening. Exons of candidate genes were amplified with primers in the flanking intron sequences with genomic DNA of affected individuals from 6 families. Intronic sequences were either available in Genbank or were developed by sequencing PAC clone 184023 (BACPAC Resources, Oakland, Calif.) with exon-specific primers. PCR products were purified with a Qiagen PCR purification kit and the PAC clone with Qiagen Midiprep kit (Qiagen, Valencia, Calif.). PCR-generated templates were sequenced from both ends on an ABI 377 slab gel sequencer with ABI Big Dye chemistry. Alternatively, cDNA was reverse transcribed from RNA of EBV-transformed patient lymphoblasts and used for PCR amplification with exonic primers. These products were sequenced (manually or ABI 377) and searched for heterozygosity or splicing variants. PCR-amplified SH3BP2 cDNA was cloned into PCRII-TOPO TA cloning vectors (Invitrogen, Carlsbad, Calif.) and sequenced (ABI 377). Variations in patient sequences and wild type sequences were examined using Blast (NCBI). Electropherograms were visually examined for heterozygosities.

Exhibit 1, References

1. Jones, W. A., *Amer. J. of Cancer* 17 (1933), 946-950.
2. Tiziani, V. et al., *Amer. J. of Human Genetics* 65(1999), 158-166.
3. Mangion, J. et al., *Amer. J. of Human Genetics* 65(1999), 151-157.
4. Pribill, I. et al., *Somatic Cell & Molecular Genetics* 23 (1997), 413-427.
5. Hadano, S. et al., *DNA Research* 5 (1998), 177-186.
6. Baxendale, S. et al., *Nature Genetics* 4 (1993), 181-186.
7. Ren, R. et al., *Science* 259 (1993); 1157-1161.
8. Bell, S. M., et al., *Genomics* 44 (1997), 163-170.
9. Songyang, Z. et al., *Mol. Cell. Biol.* 14 (1994), 2777-2785.
10. Pawson, T. et al., *Cell* 71 (1992), 359-362.
11. Sparks, A. B. et al., *Proc. Natl. Acad. Sci. USA* 93 (1996), 1540-1544.
12. Deckert, M., et al., *Immunity* 9 (1998), 595-605.
13. Weinstein, L S, et al., *N. Engl. J. Med.* 325 (1991), 1688-1695.
14. Bianco P. et al., *J. Bone Miner Res.* 15 (2000); 120-128.
15. Hirschhorn, K. et al., *Humangenetik* 1 (1965), 479-482.
16. Zollino, M., et al., *Am. J. Med. Genet.* 18 (2000), 254-261.
17. Li, B. et al., *Nat. Genet.* 24 (2000), 304-308.
18. Lewis, J. M. et al., *Proc. Natl. Acad. Sci. USA* 93 (1996), 15174-15179.
19. Welch, P J, et al., *Cell* 75 (1993), 779-790.

EQUIVALENTS

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

We claim:

1. A method for evaluating susceptibility of a human subject to a bone homeostasis disorder, comprising:
   obtain a sample of DNA from the subject; and
   evaluating the sample of DNA for the presence of nucleotides encoding a mutant residue at an amino acid position encoded by exon 9 of the SH3BP2 gene product, wherein the presence of a mutant residue is indicative of increased susceptibility to a bone homeostasis disorder.

2. The method of claim 1, further comprising the step of amplifying the DNA prior to evaluating the sample of DNA.

3. The method of claim 1 or 2, wherein evaluating comprises evaluating the sample of DNA for the presence of nucleotide encoding a mutant residue at an amino acid position selected from the group consisting of amino acid positions 415, 418, and 420 of the SH3BP2 gene product.

* * * * *

UNITED STATES PATENT AND TRADEMARK OFFICE
CERTIFICATE OF CORRECTION

| | |
|---|---|
| PATENT NO. | : 7,462,447 B2 |
| APPLICATION NO. | : 10/467033 |
| DATED | : December 9, 2008 |
| INVENTOR(S) | : Valdenize Tiziani et al. |

It is certified that error appears in the above-identified patent and that said Letters Patent is hereby corrected as shown below:

In the Specification:

At item 73 (Assignee): Please add Forsyth Dental Infirmary for Children, Boston, MA (US)

Signed and Sealed this

Fifth Day of January, 2010

David J. Kappos
*Director of the United States Patent and Trademark Office*

UNITED STATES PATENT AND TRADEMARK OFFICE
CERTIFICATE OF CORRECTION

PATENT NO. : 7,462,447 B2  
APPLICATION NO. : 10/467033  
DATED : December 9, 2008  
INVENTOR(S) : Valdenize Tiziani et al.

Page 1 of 1

It is certified that error appears in the above-identified patent and that said Letters Patent is hereby corrected as shown below:

In the Specification

Please replace the paragraph at Column 1, Line 6, with the following paragraph:
--This invention was made with government support under grant AR036819 and AR036820 awarded by the National Institutes of Health (NIH). The government has certain rights to this invention.--

Signed and Sealed this  
Fifth Day of May, 2020

Andrei Iancu  
*Director of the United States Patent and Trademark Office*